United States Patent
Manoukian et al.

(10) Patent No.: US 12,220,399 B2
(45) Date of Patent: Feb. 11, 2025

(54) PHARMACEUTICAL COMPOSITIONS COMPRISING ONE OR MORE PYRONE COMPOUNDS, AND THEIR USE FOR TREATING INFLAMMATORY AND NEURODEGENERATIVE DISEASES

(71) Applicant: NeuroTheryX Canada LTD, Toronto (CA)

(72) Inventors: Armen Manoukian, North York (CA); Fabrizio Mastronardi, Maple (CA); Sam Scanga, Burlington (CA); Frank Mercurio, Rancho Santa Fe, CA (US); Kyle W. H. Chan, San Diego, CA (US)

(73) Assignee: Adiptotec, Inc., San Diego, CA (US)

( * ) Notice: Subject to any disclaimer, the term of this patent is extended or adjusted under 35 U.S.C. 154(b) by 0 days.

(21) Appl. No.: 17/929,285

(22) Filed: Sep. 1, 2022

(65) Prior Publication Data

US 2023/0136999 A1   May 4, 2023

Related U.S. Application Data

(62) Division of application No. 15/288,780, filed on Oct. 7, 2016, now Pat. No. 11,433,047.

(60) Provisional application No. 62/239,783, filed on Oct. 9, 2015.

(51) Int. Cl.
| A61K 31/366 | (2006.01) |
| A61K 31/382 | (2006.01) |
| A61K 31/4433 | (2006.01) |

(52) U.S. Cl.
CPC .......... *A61K 31/366* (2013.01); *A61K 31/382* (2013.01); *A61K 31/4433* (2013.01)

(58) Field of Classification Search
None
See application file for complete search history.

(56) References Cited

U.S. PATENT DOCUMENTS

| 4,916,228 A | 4/1990 | Reuschling et al. |
| 5,808,062 A | 9/1998 | Domagala et al. |
| 5,977,029 A | 11/1999 | Fischer et al. |
| 6,005,103 A | 12/1999 | Domagala et al. |
| 6,423,723 B1 | 7/2002 | Tayer et al. |
| 6,511,942 B1 | 1/2003 | Lieb et al. |
| 6,589,984 B1 | 7/2003 | Naniwa et al. |
| 7,048,940 B1 | 5/2006 | Steiner |
| 7,199,152 B2 * | 4/2007 | Asakawa ................ A61P 31/00 424/734 |
| 7,256,158 B2 | 8/2007 | Lieb et al. |
| 7,674,823 B2 | 3/2010 | Martin et al. |

FOREIGN PATENT DOCUMENTS

| WO | 2003006451 A1 | 1/2003 |
| WO | 2004050624 A1 | 6/2004 |

OTHER PUBLICATIONS

Alonso et al., "Temporal trends in the incidence of multiple sclerosis: a systematic review," Neurology 2008, 71, 129-135.
Ascherio et al., "Environmental risk factors for multiple sclerosis. Part I: the role of infection," Ann. Neurol. 2007, 51, 288-299.
Ascherio et al., "Environmental risk factors for multiple sclerosis. Part II: Noninfectious factors," Ann. Neurol. 2007, 61, 504-513.
Berge et al., "Pharmaceutical salts," J. Pharm. Sci. 1977, 66, 1-19.
Compston et al., "Multiple sclerosis," Lancet 2008, 372, 1502-1517.
Debouverie, "Gender as a prognostic factor and its impact on the incidence of multiple sclerosis in Lorraine, France," J. Neurol. Sci. 2009, 286, 14-17.
Ebers, "Environmental factors and multiple sclerosis," Lancet Neurol. 2008, 7, 268-277.
Gawronski et al., "Treatment options for multiple sclerosis: current and emerging therapies," Pharmacotherapy 2010, 30, 916-927.
Gold et al., "Evolving expectations around early management of multiple sclerosis, " Ther. Adv. Neural. Disord. 2010, 3, 351-367.
Kaliyadan, "HIV and lupus erythematosus: a diagnostic dilemma," Indian J. Dermatol. 2008, 53, 80-82.
Krieger, "Multiple sclerosis therapeutic pipeline: opportunities and challenges," Mt. Sinai J. Med. 2011, 78, 192-206.
Lee, "Recent advances in the synthesis of 2-pyrones," Mar. Drugs 2015, 13, 1581-1620.
Luessi et al., "Neurodegeneration in multiple sclerosis: novel treatment strategies," Expert. Rev. Neurother. 2012, 12, 1061-1076.
Luo et al., "Syntheses of α-pyrones using gold-catalyzed coupling reactions," Org. Lett. 2011, 13, 2834-2836.
Minagar, "Current and future therapies for multiple sclerosis," Scientifica 2013, Article ID 249101, 1-11.
Nakahara et al., "Current concepts in multiple sclerosis: autoimmunity versus oligodendrogliopathy," Clin. Rev. Allergy Immunol. 2012, 42, 26-34.

(Continued)

*Primary Examiner* — Samantha L Shterengarts
(74) *Attorney, Agent, or Firm* — Lin Yu, Esq.; Juniv LLP

(57) ABSTRACT

Provided herein are pharmaceutical compositions, each comprising a pyrone compound, for example, a compound of Formula I, and a pharmaceutically acceptable excipient. Also provided herein are methods of their use for treating, preventing, or ameliorating one or more symptoms of an inflammatory, neurodegenerative, or immune-mediated disease (e.g., multiple sclerosis).

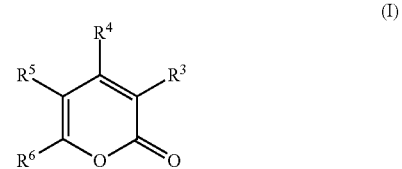

(I)

17 Claims, 3 Drawing Sheets

(56) References Cited

OTHER PUBLICATIONS

Noseworthy et al., "Multiple sclerosis," N. Engl. J. Med. 2000, 343, 938-952.
Orton et al., "Sex ratio of multiple sclerosis in Canada: a longitudinal study," Lancet Neurol. 2006, 5, 932-936.
Pugliatti et al., "The worldwide prevalence of multiple sclerosis," Clin. Neurol. Neurosurg. 2002, 104, 182-191.
Ramagopalan et al., "Parent-of-origin effect in multiple sclerosis: observations from interracial matings," Neurology 2009, 73, 602-605.
Sweeney et al., "Optic neuritis and HIV-1 infection," J. Neurol. Neurosurg. Psychiatry 1993, 56, 705-707.
Zheng et al., "Crystallographic investigation and selective inhibition of mutant isocitrate dehydrogenase," ACS Med. Chem. Lett. 2013, 4, 542-546.
Zhou et al., "First evidence of overlaps between HIV-Associated Dementia (HAD) and non-viral neurodegenerative diseases: proteomic analysis of the frontal cortex from HIV+ patients with and without dementia," Mol. Neurodegener. 2010, 5, 27.

\* cited by examiner

Non-treated

25 µM Cpz

50 µM Cpz

100 µM Cpz

500 µM Cpz

PHARMACEUTICAL COMPOSITIONS COMPRISING ONE OR MORE PYRONE COMPOUNDS, AND THEIR USE FOR TREATING INFLAMMATORY AND NEURODEGENERATIVE DISEASES

CROSS REFERENCE TO RELATED APPLICATION

This application is a divisional of U.S. application Ser. No. 15/288,780, filed Oct. 7, 2016; which claims the benefit of U.S. Provisional Application No. 62/239,783, filed Oct. 9, 2015; the disclosure of each of which is incorporated herein by reference in its entirety.

FIELD

Provided herein are pharmaceutical compositions, each comprising a pyrone compound and a pharmaceutically acceptable excipient. Also provided herein are methods of their use for treating, preventing, or ameliorating one or more symptoms of an inflammatory, neurodegenerative, or immune-mediated disease (e.g., multiple sclerosis).

BACKGROUND

Multiple sclerosis (MS), also known as disseminated sclerosis or encephalomyelitis disseminata, is a chronic, often disabling disease in which the insulating covers of nerve cells in the central nervous system (CNS) are damaged. Noseworthy et al., *N. Engl. J Med.* 2000, 343, 938-952; Ebers, *Lancet Neurol.* 2008, 7, 268-277; Luessi et al., *Expert. Rev. Neurother.* 2012, 12, 1061-1076. This damage disrupts the ability of parts of the nervous system to communicate, resulting in a wide range of signs and symptoms, including physical, mental, and sometimes psychiatric problems. Compston et al., *Lancet* 2008, 372, 1502-1517. The most common clinical signs and symptoms of MS include sensory disturbance of the limbs (~30%), partial or complete visual loss (~15%), acute and subacute motor dysfunction of the limbs (~13%), diplopia (7%), and gait dysfunction (5%). Unfortunately, fifty percent of MS patients will need help to walk within 15 years after the onset of the disease. Noseworthy et al., *N. Engl. J. Med.* 2000, 343, 938-952.

The underlying mechanism of MS is thought to be either destruction by the immune system or failure of the myelin-producing cells. Nakahara et al., *Clin. Rev. Allergy Immunol.* 2012, 42, 26-34. Thus, MS is also considered as an immune-mediated disease. MS is thought to be triggered in genetically susceptible individuals by environmental factors such as infections. Ascherio, et al., *Ann. Neurol.* 2007, 61, 288-299; Ascherio, et al., *Ann. Neurol.* 2007, 61, 504-513; Compston et al., *Lancet* 2008, 372, 1502-1517.

The worldwide prevalence of MS is estimated at between 1.1 and 2.5 million cases of MS. Pugliatti et al., *Clin Neurol. Neurosurg.* 2002, 104, 182-191. Like many other immune-mediated diseases, MS is also more prevalent in women, especially those of childbearing age, than in men. Orton et al., *Lancet Neurol.* 2006, 5, 932-936; Alonso et al., *Neurology*, 2008, 71, 129-135; Debouverie, *J. Neurol. Sci.* 2009, 286, 14-17; Ramagopalan et al., *Neurology* 2009, 73, 602-605.

Four main clinical phenotypes of MS are recognized: relapsing-remitting MS (RR-MS); primary progressive MS (PP-MS); progressive relapsing MS (PR-MS); and secondary progressive MS (SP-MS). Minagar, *Scientifica* 2013, *Article ID* 249101, 1-11. RR-MS is the most prevalent form of the disease and also the type with the greatest gender imbalance, characterized by clearly defined attacks of worsening neurologic function, followed by partial or complete recovery periods (remissions). Id.

Current treatment strategies include modifying the disease course, treating exacerbations (also called attacks, relapses, or flare-ups), managing symptoms, and improving function and safety, and providing emotional support. As of today, MS remains an incurable disease and thus, MS patients often require lifelong treatment. Gawronski et al., *Pharmacotherapy* 2010, 30, 916-927; Krieger, *Mt. Sinai J. Med.* 2011, 78, 192-206; Minagar, *Scientifica* 2013, *Article ID* 249101, 1-11. Therefore, there is a clear and unmet need to develop effective therapeutics for treating an inflammatory, neurodegenerative, or immune-mediated disease, e.g., MS.

SUMMARY OF THE DISCLOSURE

Provided herein is a pharmaceutical composition, comprising a compound of Formula I:

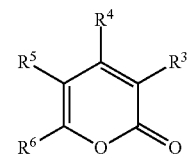

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; and a pharmaceutically acceptable excipient; wherein:

$R^3$, $R^4$, $R^5$, and $R^6$ are each independently (a) hydrogen, deuterium, cyano, halo, or nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(O)S$R^{1a}$, —C(N$R^{1a}$)N$R^{1b}R^{1c}$, —C(S)$R^{1a}$, —C(S)O$R^{1a}$, —C(S)N$R^{1b}R^{1c}$, —O$R^{1a}$, —OC(O)$R^{1a}$, —OC(O)O$R^{1a}$, —OC(O)N$R^{1b}R^{1c}$, —OC(O)S$R^{1a}$, —OC(=N$R^{1a}$)N$R^{1b}R^{1c}$, —OC(S)$R^{1a}$, —OC(S)O$R^{1a}$, —OC(S)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(O)S$R^{1d}$, —N$R^{1a}$C(=N$R^{1d}$)N$R^{1b}R^{1c}$, —N$R^{1a}$C(S)$R^{1d}$, —N$R^{1a}$C(S)O$R^{1d}$, —N$R^{1a}$C(S)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$ or —S(O)$_2$N$R^{1b}R^{1c}$; and each $R^{1a}$, $R^{1b}$, $R^{1c}$, and $R^{1d}$ is independently hydrogen, deuterium, $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or $R^{1a}$ and $R^{1c}$ together with the C and N atoms to which they are attached form heterocyclyl; or Rib and $R^{1c}$ together with the N atom to which they are attached form heterocyclyl;

wherein each alkyl, alkenyl, alkynyl, cycloalkyl, aryl, aralkyl, heteroaryl, and heterocyclyl is optionally substituted with one or more, in one embodiment, one, two, three, or four, substituents Q, where each Q is independently selected from (a) deuterium, cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents $Q^a$; and (c) —C(O)R$^a$, —C(O)OR$^a$, —C(O)NR$^b$R$^c$, —C(O)SR$^a$, —C(NR$^a$)NR$^b$R$^c$, —C(S)R$^a$, —C(S)OR$^a$, —C(S)NR$^b$R$^c$, —OR$^a$, —OC(O)R$^a$, —OC(O)OR$^a$, —OC(O)NR$^b$R$^c$, —OC(O)SR$^a$, —OC(=NR$^a$)NR$^b$R$^c$, —OC(S)R$^a$, —OC(S)OR$^a$, —OC(S)NR$^b$R$^c$, —OS(O)R$^a$, —OS(O)$_2$R$^a$, —OS(O)NR$^b$R$^c$, —OS(O)$_2$NR$^b$R$^c$, —NR$^c$, —NR$^a$C(O)R$^d$, —NR$^a$C(O)OR$^d$, —NR$^a$C(O)NR$^b$R$^c$, —NR$^a$C(O)SR$^d$, —NR$^a$C(=NR$^d$)NR$^b$R$^c$, —NR$^a$C(S)R$^d$, —NR$^a$C(S)OR$^d$, —NR$^a$C(S)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, and R$^d$ is independently (i) hydrogen or deuterium; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each of which is optionally substituted with one or more, in one embodiment, one, two, three, or four, substituents $Q^a$; or (iii) R$^b$ and R$^c$ together with the N atom to which they are attached form heterocyclyl, optionally substituted with one or more, in one embodiment, one, two, three, or four, substituents $Q^a$;

wherein each $Q^a$ is independently selected from the group consisting of (a) deuterium, cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and (c) —C(O)R$^e$, —C(O)OR$^e$, —C(O)NR$^f$R$^g$, —C(O)SR$^e$, —C(NR$^e$)NR$^f$R$^g$, —C(S)R$^e$, —C(S)OR$^e$, —C(S)NR$^f$R$^g$, —OR$^e$, —OC(O)R$^e$, —OC(O)OR$^e$, —OC(O)NR$^f$R$^g$, —OC(O)SR$^e$, —OC(=NR$^e$)NR$^f$R$^g$, —OC(S)R$^e$, —OC(S)OR$^e$, —OC(S)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR, —NR$^e$C(O)NR$^f$R$^g$, —NR$^e$C(O)SR$^f$, —NR$^e$C(=NR$^h$)NR$^f$R$^g$, —NR$^e$C(S)R$^h$, —NR$^e$C(S)OR$^f$, —NR$^e$C(S)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —SR$^e$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen or deuterium; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) R$^f$ and R$^g$ together with the N atom to which they are attached form heterocyclyl.

Furthermore, provided herein is a method for treating one or more symptoms of an inflammatory, neurodegenerative, or immune-mediated disease, in one embodiment, multiple sclerosis, in a subject, comprising administering to the subject a therapeutically effective amount of a compound of Formula I:

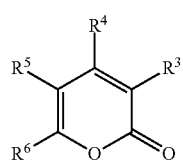

(I)

or an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof; wherein:

R$^3$, R$^4$, R$^5$, and R$^6$ are each independently (a) hydrogen, deuterium, cyano, halo, or nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —C(O)R$^{1a}$, —C(O)OR$^{1a}$, —C(O)NR$^{1b}$R$^{1c}$, —C(O)SR$^{1a}$, —C(NR$^{1a}$)NR$^{1b}$R$^{1c}$, —C(S)R$^{1a}$, —C(S)OR$^{1a}$, —C(S)NR$^{1b}$R$^{1c}$, —OR$^{1a}$, —OC(O)R$^{1a}$, —OC(O)OR$^{1a}$, —OC(O)NR$^{1b}$R$^{1c}$, —OC(O)SR$^{1a}$, —OC(=NR$^{1a}$)NR$^{1b}$R$^{1c}$, —OC(S)R$^{1a}$, —OC(S)OR$^{1a}$, —OC(S)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —N$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(O)SR$^{1d}$, —NR$^{1a}$C(=NR$^{1d}$)NR$^{1b}$R$^{1c}$, —NR$^{1a}$C(S)R$^{1d}$, —NR$^{1a}$C(S)OR$^{1d}$, —NR$^{1a}$C(S)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$; and each R$^{1a}$, R$^{1b}$, R$^{1c}$, and R$^{1d}$ is independently hydrogen, deuterium, $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or R$^{1a}$ and R$^{1c}$ together with the C and N atoms to which they are attached form heterocyclyl; or Rib and R$^{1c}$ together with the N atom to which they are attached form heterocyclyl;

wherein each alkyl, alkenyl, alkynyl, cycloalkyl, aryl, aralkyl, heteroaryl, and heterocyclyl is optionally substituted with one or more, in one embodiment, one, two, three, or four, substituents Q, where each Q is independently selected from (a) deuterium, cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents $Q^a$; and (c) —C(O)R$^a$, —C(O)OR$^a$, —C(O)NR$^b$R$^c$, —C(O)SR$^a$, —C(NR$^a$)NR$^f$R$^g$, —C(S)R$^a$, —C(S)OR$^a$, —C(S)NR$^b$R$^c$, —OR$^a$, —OC(O)R$^a$, —OC(O)OR$^a$, —OC(O)NR$^b$R$^c$, —OC(O)SR$^a$, —OC(=NR$^a$)NR$^b$R$^c$, —OC(S)R$^a$, —OC(S)OR$^a$, —OC(S)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(O)SR$^d$, —NR$^a$C(=NR$^d$)N$^b$R$^c$, —NR$^a$C(S)R$^d$, —NR$^a$C(S)OR$^d$, —NR$^a$C(S)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, and R$^d$ is independently (i) hydrogen or deuterium; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each of which is optionally substituted with one or more, in one embodiment, one, two, three, or four, substituents $Q^a$; or (iii) R$^b$ and R$^c$ together with the N atom to which they are attached form heterocyclyl, optionally substituted with one or more, in one embodiment, one, two, three, or four, substituents $Q^a$;

wherein each $Q^a$ is independently selected from the group consisting of (a) deuterium, cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and (c) —C(O)R$^e$, —C(O)OR$^e$, —C(O)NR$^f$R$^g$, —C(O)SR$^e$, —C(NR$^e$)NR$^f$R$^g$, —C(S)R$^e$, —C(S)OR$^e$, —C(S)NR$^f$R$^g$, —OR$^e$, —OC(O)R$^e$, —OC(O)OR$^e$, —OC(O)NR$^f$R$^g$, —OC(O)SR$^e$, —OC(=NR$^e$)NR$^f$R$^g$, —OC(S)R$^e$, —OC(S)OR$^e$, —OC(S)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^f$, —NR$^e$C(O)NR$^f$R$^g$, —NR$^e$C(O)SR$^f$, —NR$^e$C(=NR$^h$)NR$^f$R$^g$, —NR$^e$C(S)R$^h$, —NR$^e$C(S)OR$^f$, —NR$^e$C(S)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —SR$^e$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen or deuterium; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) R$^f$ and R$^g$ together with the N atom to which they are attached form heterocyclyl.

DETAILED DESCRIPTION

Figure 1:
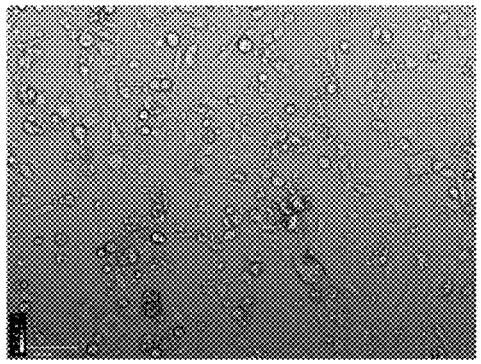
FIG. 1 shows the toxicity of cuprizone (Cpz) on human oligodendrocytes (MO3-13).
Figure 1:
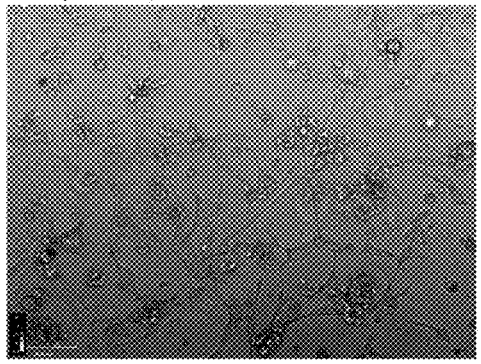
Figure 1:
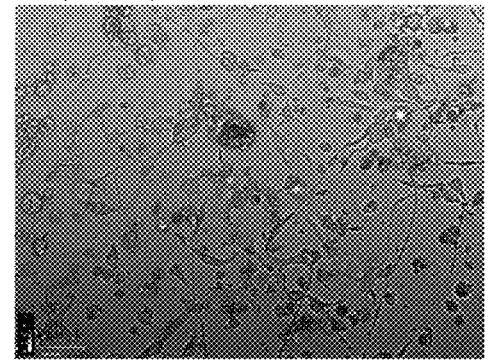
Figure 1:
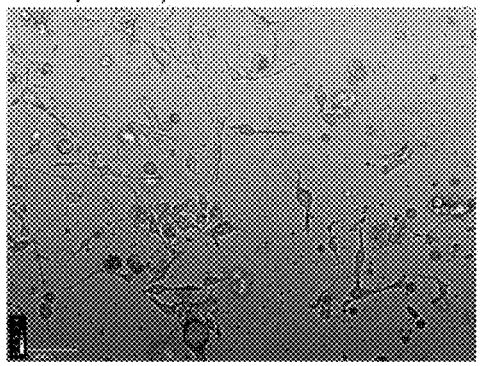
Figure 1:
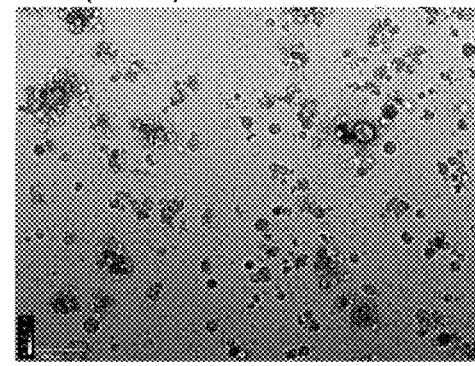

To facilitate understanding of the disclosure set forth herein, a number of terms are defined below.

Generally, the nomenclature used herein and the laboratory procedures in organic chemistry, medicinal chemistry, biochemistry, biology, and pharmacology described herein are those well known and commonly employed in the art. Unless defined otherwise, all technical and scientific terms used herein generally have the same meaning as commonly understood by one of ordinary skill in the art to which this disclosure belongs.

The term "subject" refers to an animal, including, but not limited to, a primate (e.g., human), cow, pig, sheep, goat, horse, dog, cat, rabbit, rat, or mouse. The terms "subject" and "patient" are used interchangeably herein in reference, for example, to a mammalian subject, such as a human subject, in one embodiment, a human. In one embodiment, the subject is a human.

The terms "treat," "treating," and "treatment" are meant to include alleviating or abrogating a disorder, disease, or condition, or one or more of the symptoms associated with the disorder, disease, or condition; or alleviating or eradicating the cause(s) of the disorder, disease, or condition itself.

The terms "prevent," "preventing," and "prevention" are meant to include a method of delaying and/or precluding the onset of a disorder, disease, or condition, and/or its attendant symptoms; barring a subject from acquiring a disorder, disease, or condition; or reducing a subject's risk of acquiring a disorder, disease, or condition.

The term "therapeutically effective amount" are meant to include the amount of a compound that, when administered, is sufficient to prevent development of, or alleviate to some extent, one or more of the symptoms of the disorder, disease, or condition being treated. The term "therapeutically effective amount" also refers to the amount of a compound that is sufficient to elicit the biological or medical response of a biological molecule (e.g., a protein, enzyme, RNA, or DNA), cell, tissue, system, animal, or human, which is being sought by a researcher, veterinarian, medical doctor, or clinician.

The term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, Remington: The Science and Practice of Pharmacy, 22nd ed.; Loyd et al., Eds.; The Pharmaceutical Press, 2012; Handbook of Pharmaceutical Excipients, 7th ed.; Rowe et al., Eds.; The Pharmaceutical Press, 2012; Handbook of Pharmaceutical Additives, 3rd ed.; Ash and Ash Eds.; Synapse Information Resources, Inc., 2007; Pharmaceutical Preformulation and Formulation, 2nd ed.; Gibson Ed.; CRC Press LLC, 2009.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The terms "active ingredient" and "active substance" refer to a compound, which is administered, alone or in combination with one or more pharmaceutically acceptable excipients, to a subject for treating, preventing, or ameliorating one or more symptoms of a disorder, disease, or condition. As used herein, "active ingredient" and "active substance" may be an optically active isomer of a compound described herein.

The terms "drug," "therapeutic agent," and "chemotherapeutic agent" refer to a compound, or a pharmaceutical composition thereof, which is administered to a subject for treating, preventing, or ameliorating one or more symptoms of a disorder, disease, or condition.

The term "alkyl" refers to a linear or branched saturated monovalent hydrocarbon radical, wherein the alkyl is optionally substituted with one or more substituents Q as described herein. For example, $C_{1-6}$ alkyl refers to a linear saturated monovalent hydrocarbon radical of 1 to 6 carbon atoms or a branched saturated monovalent hydrocarbon radical of 3 to 6 carbon atoms. In certain embodiments, the alkyl is a linear saturated monovalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated monovalent hydrocarbon radical of 3 to 20 ($C_{3-20}$), 3 to 15 ($C_{3-15}$), 3 to 10 ($C_3$-10), or 3 to 6 ($C_{3-6}$) carbon atoms. As used herein, linear $C_{1-6}$ and branched $C_{3-6}$ alkyl groups are also referred as "lower alkyl." Examples of alkyl groups include, but are not limited to, methyl, ethyl, propyl (including all isomeric forms), n-propyl, isopropyl, butyl (including all isomeric forms), n-butyl, isobutyl, sec-butyl, t-butyl, pentyl (including all isomeric forms), and hexyl (including all isomeric forms).

The term "alkylene" refers to a linear or branched saturated divalent hydrocarbon radical, wherein the alkylene may optionally be substituted with one or more substituents Q as described herein. For example, $C_{1-6}$ alkylene refers to a linear saturated divalent hydrocarbon radical of 1 to 6 carbon atoms or a branched saturated divalent hydrocarbon radical of 3 to 6 carbon atoms. In certain embodiments, the alkylene is a linear saturated divalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated divalent hydrocarbon radical of 3 to 20 ($C_{3-20}$), 3 to 15 ($C_{3-15}$), 3 to 10 ($C_3$-10), or 3 to 6 ($C_{3-6}$) carbon atoms. As used herein, linear $C_{1-6}$ and branched $C_{3-6}$ alkylene groups are also referred as "lower alkylene." Examples of alkylene groups include, but are not limited to, methylene, ethylene, propylene (including all isomeric forms), n-propylene, isopropylene, butylene (including all isomeric forms), n-butylene, isobutylene, t-butylene, pentylene (including all isomeric forms), and hexylene (including all isomeric forms).

The term "heteroalkylene" refers to a linear or branched saturated divalent hydrocarbon radical that contains one or more heteroatoms each independently selected from O, S, and N in the hydrocarbon chain. For example, $C_{1-6}$ heteroalkylene refers to a linear saturated divalent hydrocarbon radical of 1 to 6 carbon atoms or a branched saturated divalent hydrocarbon radical of 3 to 6 carbon atoms. In certain embodiments, the heteroalkylene is a linear saturated divalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated divalent hydrocarbon radical of 3 to 20 ($C_{3-20}$), 3 to 15 ($C_{3-15}$), 3 to 10 ($C_3$-10), or 3 to 6 ($C_{3-6}$) carbon atoms. As used herein, linear $C_{1-6}$ and branched $C_{3-6}$ heteroalkylene groups are also referred to as "lower heteroalkylene." Examples of heteroalkylene groups include, but are not limited to, —$CH_2O$—, —$CH_2OCH_2$—, —$CH_2CH_2O$—, —$CH_2NH$—, —$CH_2NHCH_2$—, —$CH_2CH_2NH$—, —$CH_2S$—, —$CH_2SCH_2$—, and —$CH_2CH_2S$—. In certain embodiments, heteroalkylene may also be optionally substituted with one or more substituents Q as described herein.

The term "alkenyl" refers to a linear or branched monovalent hydrocarbon radical, which contains one or more carbon-carbon double bond(s), in one embodiment, one, two, three, four, or five carbon-carbon double bond(s), in another embodiment, one carbon-carbon double bond. The alkenyl is optionally substituted with one or more substituents Q as described herein. The term "alkenyl" embraces radicals having a "cis" or "trans" configuration or a mixture thereof, or alternatively, a "Z" or "E" configuration or a mixture thereof, as appreciated by those of ordinary skill in the art. For example, $C_{2-6}$ alkenyl refers to a linear unsaturated monovalent hydrocarbon radical of 2 to 6 carbon atoms or a branched unsaturated monovalent hydrocarbon radical of 3 to 6 carbon atoms. In certain embodiments, the alkenyl is a linear monovalent hydrocarbon radical of 2 to 20 ($C_{2-20}$), 2 to 15 ($C_{2-15}$), 2 to 10 ($C_2$-10), or 2 to 6 ($C_{2-6}$) carbon atoms, or a branched monovalent hydrocarbon radical of 3 to 20 ($C_{3-20}$), 3 to 15 ($C_{3-15}$), 3 to 10 ($C_3$-10), or 3 to 6 ($C_{3-6}$) carbon atoms. Examples of alkenyl groups include, but are not limited to, ethenyl, propen-1-yl, propen-2-yl, allyl, butenyl, and 4-methylbutenyl.

The term "alkenylene" refers to a linear or branched divalent hydrocarbon radical, which contains one or more carbon-carbon double bond(s), in one embodiment, one, two, three, four, or five carbon-carbon double bond(s), in another embodiment, one carbon-carbon double bond. The alkenylene may be optionally substituted with one or more substituents Q as described herein. The term "alkenylene" embraces radicals having a "cis" or "trans" configuration or a mixture thereof, or alternatively, a "Z" or "E" configuration or a mixture thereof, as appreciated by those of ordinary skill in the art. For example, $C_{2-6}$ alkenylene refers to a linear unsaturated divalent hydrocarbon radical of 2 to 6 carbon atoms or a branched unsaturated divalent hydrocarbon radical of 3 to 6 carbon atoms. In certain embodiments, the alkenylene is a linear divalent hydrocarbon radical of 2 to 20 ($C_2$-$C_{20}$), 2 to 15 ($C_{2-15}$), 2 to 10 ($C_{2-10}$), or 2 to 6 ($C_{2-6}$) carbon atoms, or a branched divalent hydrocarbon radical of 3 to 20 ($C_{3-20}$), 3 to 15 ($C_{3-15}$), 3 to 10 ($C_3$-10), or 3 to 6 ($C_{3-6}$) carbon atoms. Examples of alkenylene groups include, but are not limited to, ethenylene, allylene, propenylene, butenylene, and 4-methylbutenylene.

The term "heteroalkenylene" refers to a linear or branched divalent hydrocarbon radical, which contains one or more carbon-carbon double bond(s), in one embodiment, one, two, three, four, or five carbon-carbon double bond(s), in another embodiment, one carbon-carbon double bond, and which contains one or more heteroatoms each independently selected from O, S, and N in the hydrocarbon chain. The heteroalkenylene may be optionally substituted with one or more substituents Q as described herein. The term "heteroalkenylene" embraces radicals having a "cis" or "trans" configuration or a mixture thereof, or alternatively, a "Z" or "E" configuration or a mixture thereof, as appreciated by those of ordinary skill in the art. For example, $C_{2-6}$ heteroalkenylene refers to a linear unsaturated divalent hydrocarbon radical of 2 to 6 carbon atoms or a branched unsaturated divalent hydrocarbon radical of 3 to 6 carbon atoms. In certain embodiments, the heteroalkenylene is a linear divalent hydrocarbon radical of 2 to 20 ($C_{2-20}$), 2 to 15 ($C_{2-15}$), 2 to 10 ($C_2$-10), or 2 to 6 ($C_{2-6}$) carbon atoms, or a branched divalent hydrocarbon radical of 3 to 20 ($C_{3-20}$), 3 to 15 ($C_{3-15}$), 3 to 10 ($C_3$-10), or 3 to 6 ($C_{3-6}$) carbon atoms. Examples of heteroalkenylene groups include, but are not limited to, —CH=CHO—, —CH=CHOCH$_2$—, —CH=CHCH$_2$O—, —CH=CHS—, —CH=CHSCH$_2$—, —CH=CHCH$_2$S—, or —CH=CHCH$_2$NH—.

The term "alkynyl" refers to a linear or branched monovalent hydrocarbon radical, which contains one or more carbon-carbon triple bond(s), in one embodiment, one, two, three, four, or five carbon-carbon triple bond(s), in another embodiment, one carbon-carbon triple bond. The alkynyl is optionally substituted with one or more substituents Q as described herein. For example, $C_{2-6}$ alkynyl refers to a linear unsaturated monovalent hydrocarbon radical of 2 to 6 carbon atoms or a branched unsaturated monovalent hydrocarbon radical of 3 to 6 carbon atoms. In certain embodiments, the alkynyl is a linear monovalent hydrocarbon radical of 2 to 20 ($C_{2-20}$), 2 to 15 ($C_{2-15}$), 2 to 10 ($C_2$-10), or 2 to 6 ($C_{2-6}$) carbon atoms, or a branched monovalent hydrocarbon radical of 4 to 20 ($C_{4-20}$), 4 to 15 ($C_{4-15}$), 4 to 10 ($C_4$-10), or 4 to 6 ($C_{4-6}$) carbon atoms. Examples of alkynyl groups include, but are not limited to, ethynyl (—C≡CH), propynyl (including all isomeric forms, e.g., 1-propynyl (—C≡C—CH$_3$) and propargyl (—CH$_2$C≡CH)), butynyl (including all isomeric forms, e.g., 1-butyn-1-yl and 2-butyn-1-yl), pentynyl (including all isomeric forms, e.g., 1-pentyn-1-yl and 1-methyl-2-butyn-1-yl), and hexynyl (including all isomeric forms, e.g., 1-hexyn-1-yl).

The term "cycloalkyl" refers to a cyclic monovalent hydrocarbon radical, which is optionally substituted with one or more substituents Q as described herein. In one embodiment, the cycloalkyl is a saturated or unsaturated but non-aromatic, and/or bridged, and/or non-bridged, and/or fused bicyclic group. In certain embodiments, the cycloalkyl has from 3 to 20 ($C_{3-20}$), from 3 to 15 ($C_{3-15}$), from 3 to 10 ($C_3$-10), or from 3 to 7 ($C_{3-7}$) carbon atoms. Examples of cycloalkyl groups include, but are not limited to, cyclopropyl, cyclobutyl, cyclopentyl, cyclopentenyl, cyclohexyl, cyclohexenyl, cyclohexadienyl, cycloheptyl, cycloheptenyl, bicyclo[2.1.1]hexyl, bicyclo[2.2.1]heptyl, decalinyl, and adamantyl.

The term "aryl" refers to a monovalent monocyclic aromatic hydrocarbon radical and/or monovalent polycyclic aromatic hydrocarbon radical that contain at least one aromatic carbon ring. In certain embodiments, the aryl has from 6 to 20 ($C_{6-20}$), from 6 to 15 ($C_{6-15}$), or from 6 to 10 ($C_{6-10}$) ring atoms. Examples of aryl groups include, but are not limited to, phenyl, naphthyl, fluorenyl, azulenyl, anthryl, phenanthryl, pyrenyl, biphenyl, and terphenyl. The aryl also refers to bicyclic or tricyclic carbon rings, where one of the rings is aromatic and the others of which may be saturated, partially unsaturated, or aromatic, for example, dihydronaphthyl, indenyl, indanyl, or tetrahydronaphthyl (tetralinyl). In one embodiment, the aryl is monocyclic. In another embodiment, the aryl is polycyclic. In yet another embodiment, the aryl is bicyclic. In still another embodiment, the aryl is tricyclic. In certain embodiments, the aryl is optionally substituted with one or more substituents Q as described herein.

The term "aralkyl" or "arylalkyl" refers to a monovalent alkyl group substituted with one or more aryl groups. In certain embodiments, the aralkyl has from 7 to 30 ($C_{7-30}$), from 7 to 20 ($C_{7-20}$), or from 7 to 16 ($C_{7-16}$) carbon atoms. Examples of aralkyl groups include, but are not limited to, benzyl, 2-phenylethyl, and 3-phenylpropyl. In certain embodiments, the aralkyl is optionally substituted with one or more substituents Q as described herein.

The term "heteroaryl" refers to a monovalent monocyclic aromatic group or monovalent polycyclic aromatic group that contain at least one aromatic ring, wherein at least one aromatic ring contains one or more heteroatoms independently selected from O, S, and N in the ring. The heteroaryl is bonded to the rest of a molecule through the aromatic ring. Each ring of a heteroaryl group can contain one or two O atoms, one or two S atoms, and/or one to four N atoms; provided that the total number of heteroatoms in each ring is four or less and each ring contains at least one carbon atom. In certain embodiments, the heteroaryl has from 5 to 20, from 5 to 15, or from 5 to 10 ring atoms. In one embodiment, the heteroaryl is monocyclic. Examples of monocyclic heteroaryl groups include, but are not limited to, furanyl, imidazolyl, isothiazolyl, isoxazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, and triazolyl. In one embodiment, the heteroaryl is bicyclic. Examples of bicyclic heteroaryl groups include, but are not limited to, benzofuranyl, benzimidazolyl, benzisoxazolyl, benzopyranyl, benzothiadiazolyl, benzothiazolyl, benzothienyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, and thienopyridyl. In yet another embodiment, the heteroaryl is tricyclic. Examples of tricyclic heteroaryl groups include, but are not limited to, acridinyl, benzindolyl, carbazolyl, dibenzofuranyl, perimidinyl, phenanthrolinyl, phenanthridinyl, phenarsazinyl, phenazinyl, phenothiazinyl, phenoxazinyl, and xanthenyl. In certain embodiments, the heteroaryl is optionally substituted with one or more substituents Q as described herein.

The term "heterocyclyl" or "heterocyclic" refers to a monovalent monocyclic non-aromatic ring system or monovalent polycyclic ring system that contains at least one non-aromatic ring, wherein one or more of the non-aromatic ring atoms are heteroatoms independently selected from O, S, and N; and the remaining ring atoms are carbon atoms. In certain embodiments, the heterocyclyl or heterocyclic group has from 3 to 20, from 3 to 15, from 3 to 10, from 3 to 8, from 4 to 7, or from 5 to 6 ring atoms. The heterocyclyl is bonded to the rest of a molecule through the non-aromatic ring. In certain embodiments, the heterocyclyl is a monocyclic, bicyclic, tricyclic, or tetracyclic ring system, which may be fused or bridged, and in which nitrogen or sulfur atoms may be optionally oxidized, nitrogen atoms may be optionally quaternized, and some rings may be partially or fully saturated, or aromatic. The heterocyclyl may be attached to the main structure at any heteroatom or carbon atom which results in the creation of a stable compound. Examples of heterocyclyls and heterocyclic groups include, but are not limited to, azepinyl, benzodioxanyl, benzodioxolyl, benzofuranonyl, benzopyranonyl, benzopyranyl, benzotetrahydrofuranyl, benzotetrahydrothienyl, benzothiopyranyl, benzoxazinyl, β-carbolinyl, chromanyl, chromonyl, cinnolinyl, coumarinyl, decahydroisoquinolinyl, dihydrobenzisothiazinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isobenzotetrahydrofuranyl, isobenzotetrahydrothienyl, isochromanyl, isocoumarinyl, isoindolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, tetrahydroquinolinyl, and 1,3,5-trithianyl. In certain embodiments, the heterocyclyl is optionally substituted with one or more substituents Q as described herein.

The term "halogen", "halide," or "halo" refers to fluorine, chlorine, bromine, and/or iodine.

The term "optionally substituted" is intended to mean that a group or substituent, such as an alkyl, alkylene, heteroalkylene, alkenyl, alkenylene, heteroalkenylene, alkynyl, cycloalkyl, aryl, aralkyl, heteroaryl, or heterocyclyl group, may be substituted with one or more, one, two, three, or four, substituents Q, each of which is independently selected from, e.g., (a) deuterium (-D), cyano (—CN), halo, and nitro (—$NO_2$); (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents $Q^a$; and (c) —C(O)$R^a$, —C(O)O$R^a$, —C(O)NR$^b$R$^c$, —C(O)S$R^a$, —C(N$R^a$)NR$^b$R$^c$, —C(S)$R^a$, —C(S)O$R^a$, —C(S)NR$^b$R$^c$, —O$R^a$, —OC(O)$R^a$, —OC(O)O$R^a$, —OC(O)NR$^b$R$^c$, —OC(O)S$R^a$, —OC(=N$R^a$)NR$^b$R$^c$, —OC(S)$R^a$, —OC(S)O$R^a$, —OC(S)NR$^b$R$^c$, —OS(O)$R^a$, —OS(O)$_2$$R^a$, —OS(O)NR$^b$R$^c$, —OS(O)$_2$NR$^b$R$^c$, —NR$^b$R$^c$, —NR$^a$C(O)$R^d$, —NR$^a$C(O)O$R^d$, —NR$^a$C(O)NR$^b$R$^c$, —NR$^a$C(O)S$R^d$, —NR$^a$C(=N$R^d$)NR$^b$R$^c$, —NR$^a$C(S)$R^d$, —NR$^a$C(S)O$R^d$, —NR$^a$C(S)NR$^b$R$^c$, —NR$^a$S(O)$R^d$, —NR$^a$S(O)$_2$$R^d$, —NR$^a$S(O)NR$^b$R$^c$, —NR$^a$S(O)$_2$NR$^b$R$^g$, —S$R^a$, —S(O)$R^a$, —S(O)$_2$$R^a$, —S(O)NR$^b$R$^c$, and —S(O)$_2$NR$^b$R$^c$, wherein each $R^a$, $R^b$, $R^c$, and $R^d$ is independently (i) hydrogen or deuterium; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each of which is optionally substituted with one or more, in one embodiment, one, two, three, or four, substituents $Q^a$; or (iii) $R^b$ and $R^c$ together with the N atom to which they are attached form heterocyclyl, optionally substituted with one or more, in one embodiment, one, two, three, or four, substituents $Q^a$. As used herein, all groups that can be substituted are "optionally substituted," unless otherwise specified.

In one embodiment, each $Q^a$ is independently selected from the group consisting of (a) deuterium, cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and (c) —C(O)R$^e$, —C(O)OR$^e$, —C(O)NR$^f$R$^g$, —C(O)SR$^e$, —C(NR$^e$)NR$^f$R$^g$, —C(S)R$^e$, —C(S)OR$^e$, —C(S)NR$^f$R$^g$, —OR$^e$, —OC(O)R$^e$, —OC(O)OR$^e$, —OC(O)NR$^f$R$^g$, —OC(O)SR$^e$, —OC(=NR$^e$)NR$^f$R$^g$, —OC(S)R$^e$, —OC(S)OR$^e$, —OC(S)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^f$, —NR$^e$C(O)NR$^f$R$^g$, —NR$^e$C(O)SR$^f$, —NR$^e$C(=NR$^h$)NR$^f$R$^g$, —NR$^e$C(S)R$^h$, —NR$^e$C(S)OR, —NR$^e$C(S)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —SR$^e$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen or deuterium; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) R$^f$ and R$^g$ together with the N atom to which they are attached form heterocyclyl.

In certain embodiments, "optically active" and "enantiomerically active" refer to a collection of molecules, which has an enantiomeric excess of no less than about 50%, no less than about 70%, no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, or no less than about 99.8%. In certain embodiments, an optically active compound comprises about 95% or more of one enantiomer and about 5% or less of the other enantiomer based on the total weight of the enantiomeric mixture in question.

In describing an optically active compound, the prefixes R and S are used to denote the absolute configuration of the compound about its chiral center(s). The (+) and (−) are used to denote the optical rotation of the compound, that is, the direction in which a plane of polarized light is rotated by the optically active compound. The (−) prefix indicates that the compound is levorotatory, that is, the compound rotates the plane of polarized light to the left or counterclockwise. The (+) prefix indicates that the compound is dextrorotatory, that is, the compound rotates the plane of polarized light to the right or clockwise. However, the sign of optical rotation, (+) and (−), is not related to the absolute configuration of the compound, R and S.

The term "isotopically enriched" refers to a compound that contains an unnatural proportion of an isotope at one or more of the atoms that constitute such a compound. In certain embodiments, an isotopically enriched compound contains unnatural proportions of one or more isotopes, including, but not limited to, hydrogen (H), deuterium ($^2$H), tritium ($^3$H), carbon-11 ($^{11}$C), carbon-12 ($^{12}$C), carbon-13 ($^{13}$C), carbon-14 ($^{14}$C), nitrogen-13 ($^{13}$N), nitrogen-14 ($^{14}$N), nitrogen-15 ($^{15}$N), oxygen-14 ($^{14}$O), oxygen-15 ($^{15}$O), oxygen-16 ($^{16}$O), oxygen-17 ($^{17}$O), oxygen-18 ($^{18}$O), fluorine-17 ($^{17}$F), fluorine-18 ($^{18}$F), phosphorus-31 ($^{31}$P), phosphorus-32 ($^{32}$p), phosphorus-33 ($^{33}$P), sulfur-32 ($^{32}$S), sulfur-33 ($^{33}$S), sulfur-34 ($^{34}$S), sulfur-35 ($^{35}$S), sulfur-36 ($^{36}$S), chlorine-35 ($^{35}$Cl), chlorine-36 ($^{36}$Cl), chlorine-37 ($^{37}$Cl), bromine-79 ($^{79}$Br), bromine-81 ($^{81}$Br), iodine-123 ($^{123}$I), iodine-125 ($^{125}$I), iodine-127 ($^{127}$I), iodine-129 ($^{129}$I), and iodine-131 ($^{131}$I). In certain embodiments, an isotopically enriched compound is in a stable form, that is, non-radioactive. In certain embodiments, an isotopically enriched compound contains unnatural proportions of one or more isotopes, including, but not limited to, hydrogen ($^1$H), deuterium ($^2$H), carbon-12 ($^{12}$C), carbon-13 ($^{13}$C), nitrogen-14 ($^{14}$N), nitrogen-15 ($^{15}$N), oxygen-16 ($^{16}$O), oxygen-17 ($^{17}$O), oxygen-18 ($^{18}$O), fluorine-17 ($^{17}$F), phosphorus-31 ($^{31}$P), sulfur-32 ($^{32}$S), sulfur-33 ($^{33}$S), sulfur-34 ($^{34}$S), sulfur-36 ($^{36}$S), chlorine-35 ($^{35}$Cl), chlorine-37 ($^{37}$Cl), bromine-79 ($^{79}$Br), bromine-81 ($^{81}$Br), and iodine-127 ($^{127}$I). In certain embodiments, an isotopically enriched compound is in an unstable form, that is, radioactive. In certain embodiments, an isotopically enriched compound contains unnatural proportions of one or more isotopes, including, but not limited to, tritium ($^3$H), carbon-11 ($^{11}$C), carbon-14 ($^{14}$C), nitrogen-13 ($^{13}$N), oxygen-14 ($^{14}$O), oxygen-15 ($^{15}$O), fluorine-18 ($^{18}$F), phosphorus-32 ($^{32}$P), phosphorus-33 ($^{33}$P), sulfur-35 ($^{35}$S), chlorine-36 ($^{36}$Cl), iodine-123 ($^{123}$I), iodine-125 ($^{125}$I), iodine-129 ($^{129}$I), and iodine-131 ($^{131}$I). It will be understood that, in a compound as provided herein, any hydrogen can be $^2$H, as example, or any carbon can be $^{13}$C, as example, or any nitrogen can be $^{15}$N, as example, or any oxygen can be $^{18}$O, as example, where feasible according to the judgment of one of ordinary skill in the art.

The term "isotopic enrichment" refers to the percentage of incorporation of a less prevalent isotope (e.g., D for deuterium or hydrogen-2) of an element at a given position in a molecule in the place of a more prevalent isotope (e.g., $^1$H for protium or hydrogen-1) of the element. As used herein, when an atom at a particular position in a molecule is designated as a particular less prevalent isotope, it is understood that the abundance of that isotope at that position is substantially greater than its natural abundance.

The term "isotopic enrichment factor" refers the ratio between the isotopic abundance in an isotopically enriched compound and the natural abundance of a specific isotope.

The term "hydrogen" or the symbol "H" refers to the composition of naturally occurring hydrogen isotopes, which include protium (H), deuterium ($^2$H or D), and tritium (H), in their natural abundances. Protium is the most common hydrogen isotope having a natural abundance of more than 99.98%. Deuterium is a less prevalent hydrogen isotope having a natural abundance of about 0.0156%.

The term "deuterium enrichment" refers to the percentage of incorporation of deuterium at a given position in a molecule in the place of hydrogen. For example, deuterium enrichment of 1% at a given position means that 1% of molecules in a given sample contain deuterium at the specified position. Because the naturally occurring distribution of deuterium is about 0.0156% on average, deuterium enrichment at any position in a compound synthesized using non-enriched starting materials is about 0.0156% on average. As used herein, when a particular position in an isotopically enriched compound is designated as having deuterium, it is understood that the abundance of deuterium at that position in the compound is substantially greater than its natural abundance (0.0156%).

The term "carbon" or the symbol "C" refers to the composition of naturally occurring carbon isotopes, which include carbon-12 ($^{12}$C) and carbon-13 ($^{13}$C) in their natural abundances. Carbon-12 is the most common carbon isotope having a natural abundance of more than 98.89%. Carbon-13 is a less prevalent hydrogen isotope having a natural abundance of about 1.11%.

The term "carbon-13 enrichment" or "$^{13}$C enrichment" refers to the percentage of incorporation of carbon-13 at a given position in a molecule in the place of carbon. For example, carbon-13 enrichment of 10% at a given position means that 10% of molecules in a given sample contain carbon-13 at the specified position. Because the naturally occurring distribution of carbon-13 is about 1.11% on average, carbon-13 enrichment at any position in a compound synthesized using non-enriched starting materials is about 1.11% on average. As used herein, when a particular position in an isotopically enriched compound is designated as having carbon-13, it is understood that the abundance of carbon-13 at that position in the compound is substantially greater than its natural abundance (1.11%).

The terms "substantially pure" and "substantially homogeneous" mean sufficiently homogeneous to appear free of readily detectable impurities as determined by standard analytical methods used by one of ordinary skill in the art, including, but not limited to, thin layer chromatography (TLC), gel electrophoresis, high performance liquid chromatography (HPLC), gas chromatography (GC), nuclear magnetic resonance (NMR), and mass spectrometry (MS); or sufficiently pure such that further purification would not detectably alter the physical, chemical, biological, and/or pharmacological properties, such as enzymatic and biological activities, of the substance. In certain embodiments, "substantially pure" or "substantially homogeneous" refers to a collection of molecules, wherein at least about 50%, at least about 70%, at least about 80%, at least about 90%, at least about 95%, at least about 98%, at least about 99%, or at least about 99.5% by weight of the molecules are a single compound, including a single enantiomer, a racemic mixture, or a mixture of enantiomers, as determined by standard analytical methods. As used herein, when an atom at a particular position in an isotopically enriched molecule is designated as a particular less prevalent isotope, a molecule that contains other than the designated isotope at the specified position is an impurity with respect to the isotopically enriched compound. Thus, for a deuterated compound that has an atom at a particular position designated as deuterium, a compound that contains a protium at the same position is an impurity.

The term "solvate" refers to a complex or aggregate formed by one or more molecules of a solute, e.g., a compound described herein, and one or more molecules of a solvent, which present in stoichiometric or non-stoichiometric amount. Suitable solvents include, but are not limited to, water, methanol, ethanol, n-propanol, isopropanol, and acetic acid. In certain embodiments, the solvent is pharmaceutically acceptable. In one embodiment, the complex or aggregate is in a crystalline form. In another embodiment, the complex or aggregate is in a noncrystalline form. Where the solvent is water, the solvate is a hydrate. Examples of hydrates include, but are not limited to, a hemihydrate, monohydrate, dihydrate, trihydrate, tetrahydrate, and pentahydrate.

The phrase "an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof" has the same meaning as the phrase "(i) an enantiomer, a mixture of enantiomers, a mixture of two or more diastereomers, a tautomer, a mixture of two or more tautomers, or an isotopic variant of the compound referenced therein; or (ii) a pharmaceutically acceptable salt, solvate, hydrate, or prodrug of the compound referenced therein, or (iii) a pharmaceutically acceptable salt, solvate, hydrate, or prodrug of an enantiomer, a mixture of enantiomers, a mixture of two or more tautomers, a mixture of two or more tautomers, or an isotopic variant of the compound referenced therein."

Pharmaceutical Compositions

In one embodiment, provided herein is a pharmaceutical composition, comprising a compound of Formula I:

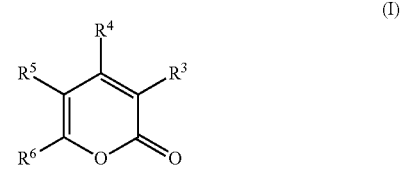

or an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof; and a pharmaceutically acceptable excipient; wherein:

$R^3$, $R^4$, $R^5$, and $R^6$ are each independently (a) hydrogen, deuterium, cyano, halo, or nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)NR$^{1b}$R$^{1c}$, —C(O)S$R^{1a}$, —C(NR$^{1a}$)NR$^{1b}$R$^{1c}$, —C(S)R$^{1a}$, —C(S)OR$^{1a}$, —C(S)NR$^{1b}$R$^{1c}$, —OR$^{1a}$, —OC(O)R$^{1a}$, —OC(O)OR$^{1a}$, —OC(O)NR$^{1b}$R$^{1c}$, —OC(O)SR$^{1a}$, —OC(=NR$^{1a}$)NR$^{1b}$R$^{1c}$, —OC(S)R$^{1a}$, —OC(S)OR$^{1a}$, —OC(S)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —N$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(O)SR$^{1d}$, —NR$^{1a}$C(=NR$^{1d}$)NR$^{1b}$R$^{1c}$, —NR$^{1a}$C(S)R$^{1d}$, —NR$^{1a}$C(S)OR$^{1d}$, —NR$^{1a}$C(S)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$; and each $R^{1a}$, $R^{1b}$, $R^{1c}$, and $R^{1d}$ is independently hydrogen, deuterium, $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or $R^{1a}$ and $R^{1c}$ together with the C and N atoms to which they are attached form heterocyclyl; or Rib and $R^{1c}$ together with the N atom to which they are attached form heterocyclyl;

wherein each alkyl, alkenyl, alkynyl, cycloalkyl, aryl, aralkyl, heteroaryl, and heterocyclyl is optionally substituted with one or more, in one embodiment, one, two, three, or four, substituents Q, where each Q is independently selected from (a) deuterium, cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents $Q^a$; and (c) —C(O)$R^a$, —C(O)O$R^a$, —C(O)NR$^b$R$^c$, —C(O)S$R^a$, —C(NR$^a$)NR$^b$R$^c$, —C(S)R$^a$, —C(S)OR$^a$, —C(S)NR$^b$R$^c$, —OR$^a$, —OC(O)R$^a$, —OC(O)OR$^a$, —OC(O)NR$^b$R$^c$, —OC(O)SR$^a$, —OC(=NR$^a$)NR$^b$R$^c$, —OC(S)R$^a$, —OC(S)OR$^a$, —OC(S)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(O)SR$^d$, —NR$^a$C(=NR$^d$)N$^b$R$^c$, —NR$^a$C(S)R$^d$, —NR$^a$C(S)OR$^d$, —NR$^a$C(S)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, and R$^d$ is independently (i) hydrogen or deuterium; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each of which is optionally substituted with one or more, in one embodiment, one, two, three, or four, substituents $Q^a$; or (iii) $R^b$ and $R^c$ together with the N atom to which they are attached form heterocyclyl, optionally substituted with one or more, in one embodiment, one, two, three, or four, substituents $Q^a$;

wherein each $Q^a$ is independently selected from the group consisting of (a) deuterium, cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and (c) —C(O)$R^e$, —C(O)O$R^e$, —C(O)N$R^f R^g$, —C(O)S$R^e$, —C(N$R^e$)N$R^f R^g$, —C(S)$R^e$, —C(S)O$R^e$, —C(S)N$R^f R^g$, —O$R^e$, —OC(O)$R^e$, —OC(O)O$R^e$, —OC(O)N$R^f R^g$, —OC(O)S$R^e$, —OC(=N$R^e$)N$R^f R^g$, —OC(S)$R^e$, —OC(S)O$R^e$, —OC(S)N$R^f R^g$, —OS(O)$R^e$, —OS(O)$_2 R^e$, —OS(O)N$R^f R^g$, —OS(O)$_2$N$R^f R^g$, —N$R^f R^g$, —N$R^e$C(O)$R^h$, —N$R^e$C(O)O$R^f$, —N$R^e$C(O)N$R^f R^g$, —N$R^e$C(O)S$R^f$, —N$R^e$C(=N$R^h$)N$R^f R^g$, —N$R^e$C(S)$R^h$, —N$R^e$C(S)O$R^f$, —N$R^e$C(S)N$R^f R^g$, —N$R^e$S(O)$R^h$, —N$R^e$S(O)$_2 R^h$, —N$R^e$S(O)N$R^f R^g$, —N$R^e$S(O)$_2$N$R^f R^g$, —S$R^e$, —S(O)$R^e$, —S(O)$_2 R^e$, —S(O)N$R^f R^g$, and —S(O)$_2$N$R^f R^g$; wherein each $R^e$, $R^f$, $R^g$, and $R^h$ is independently (i) hydrogen or deuterium; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) $R^f$ and $R^g$ together with the N atom to which they are attached form heterocyclyl.

In one embodiment, the pharmaceutical composition provided herein is a solid pharmaceutical composition.

In one embodiment, in Formula I, $R^3$ and $R^5$ are each independently hydrogen, deuterium, or fluoro. In another embodiment, in Formula I, $R^3$ and $R^5$ are each independently hydrogen or deuterium.

In one embodiment, in Formula I,
$R^3$ and $R^5$ are each independently hydrogen or deuterium;
$R^4$ is $C_{1-6}$ alkyl or $C_{6-14}$ aryl, each optionally substituted with one or more substituents Q; and
$R^6$ is $C_{3-7}$ cycloalkyl, $C_{6-14}$ aryl, $C_{7-15}$ aralkyl, heteroaryl, or heterocyclyl, optionally substituted with one or more substituents Q.

In one embodiment, in Formula I, $R^3$ and $R^5$ are hydrogen; and $R^4$ is $C_{1-6}$ alkyl or $C_{6-14}$ aryl, each optionally substituted with one or more substituents Q. In another embodiment, in Formula I, $R^3$ and $R^5$ are hydrogen; and $R^4$ is $C_{1-6}$ alkyl, optionally substituted with one or more substituents Q. In yet another embodiment, in Formula I, $R^3$ and $R^5$ are hydrogen; and $R^4$ is —C($R^{4a}$)$_3$, wherein each $R^{4a}$ is independently hydrogen, deuterium, fluoro, or hydroxyl. In yet another embodiment, in Formula I, $R^3$ and $R^5$ are hydrogen; $R^4$ is —C($R^{4a}$)$_3$, wherein each $R^{4a}$ is independently hydrogen, deuterium, fluoro, or hydroxyl; and $R^6$ is $C_{3-7}$ cycloalkyl or $C_{6-14}$ aryl, each of which is optionally substituted with one or more substituents Q. In yet another embodiment, in Formula I, $R^3$ and $R^5$ are hydrogen; $R^4$ is methyl; and $R^6$ is monocyclic $C_{3-7}$ cycloalkyl, optionally substituted with one or more substituents Q. In yet another embodiment, in Formula I, $R^3$ and $R^5$ are hydrogen; $R^4$ is methyl; and $R^6$ is cyclohexyl, optionally substituted with one or more substituents Q. In yet another embodiment, in Formula I, $R^3$ and $R^5$ are hydrogen; $R^4$ is methyl; and $R^6$ is monocyclic $C_{6-14}$ aryl, optionally substituted with one or more substituents Q. In still another embodiment, in formula I, $R^3$ and $R^5$ are hydrogen; $R^4$ is methyl; and $R^6$ is phenyl, optionally substituted with one or more substituents Q.

In one embodiment, in Formula I, $R^3$ and $R^5$ are hydrogen; $R^4$ is $C_{6-14}$ aryl, optionally substituted with one or more substituents Q. In another embodiment, in Formula I, $R^3$ and $R^5$ are hydrogen; $R^4$ is $C_{6-14}$ aryl, optionally substituted with one or more substituents Q; and $R^6$ is $C_{3-7}$ cycloalkyl or $C_{6-14}$ aryl, each of which is optionally substituted with one or more substituents Q. In yet another embodiment, in Formula I, $R^3$ and $R^5$ are hydrogen; $R^4$ is phenyl, optionally substituted with one or more substituents Q; and $R^6$ is monocyclic $C_{3-7}$ cycloalkyl, optionally substituted with one or more substituents Q. In yet another embodiment, in Formula I, $R^3$ and $R^5$ are hydrogen; $R^4$ is phenyl, optionally substituted with one or more substituents Q; and $R^6$ is cyclohexyl, optionally substituted with one or more substituents Q. In yet another embodiment, in Formula I, $R^3$ and $R^5$ are hydrogen; $R^4$ is phenyl, optionally substituted with one or more substituents Q; and $R^6$ is monocyclic $C_{6-14}$ aryl, optionally substituted with one or more substituents Q. In still another embodiment, in formula I, $R^3$ and $R^5$ are hydrogen; $R^4$ is phenyl, optionally substituted with one or more substituents Q; and $R^6$ is phenyl, optionally substituted with one or more substituents Q.

In another embodiment, the compound described herein has the structure of Formula II.

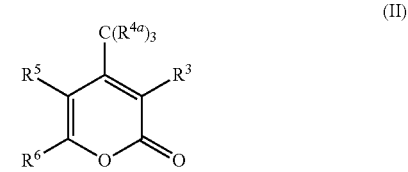

(II)

or an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof; wherein each $R^{4a}$ is independently hydrogen, deuterium, fluoro, or hydroxyl; and $R^3$, $R^5$, and $R^6$ are each as defined herein.

In one embodiment, in Formula II, $R^3$ and $R^5$ are hydrogen. In another embodiment, in Formula II, $R^3$ and $R^5$ are hydrogen; and $R^6$ is $C_{3-7}$ cycloalkyl or $C_{6-14}$ aryl, each optionally substituted with one or more substituents Q. In yet another embodiment, in Formula II, $R^3$ and $R^5$ are hydrogen; and $R^6$ is monocyclic $C_{3-7}$ cycloalkyl, optionally substituted with one or more substituents Q. In yet another embodiment, in Formula II, $R^3$ and $R^5$ are hydrogen; and $R^6$ is cyclohexyl, optionally substituted with one or more substituents Q. In yet another embodiment, in Formula II, $R^3$ and $R^5$ are hydrogen; and $R^6$ is monocyclic $C_{6-14}$ aryl, optionally substituted with one or more substituents Q. In still another embodiment, in Formula II, $R^3$ and $R^5$ are hydrogen; and $R^6$ is phenyl, optionally substituted with one or more substituents Q.

In yet another embodiment, the compound described herein has the structure of Formula III:

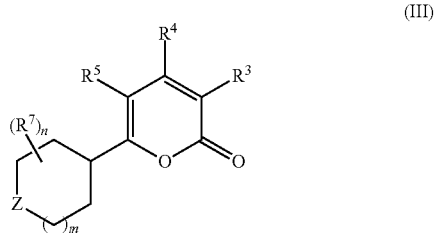

(III)

or an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof; wherein:

Z is a bond, —O—, —S—, —S(O)—, —S(O$_2$)—, or —N(R')— each $R^7$ is independently (a) deuterium, halo, cyano, nitro, or guanidine; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each of which is optionally substituted with one or more substituents Q; or (c) —C(O)$R^{1a}$, —C(O)O$R^{1a}$, —C(O)N$R^{1b}R^{1c}$, —C(O)S$R^{1a}$, —C(N$R^{1a}$)N$R^{1b}R^{1c}$, —C(S)$R^{1a}$, —C(S)O$R^{1a}$, —C(S)N$R^{1b}R^{1c}$, —O$R^{1a}$, —OC(O)$R^{1a}$, —OC(O)O$R^{1a}$, —OC(O)N$R^{1b}R^{1c}$, —OC(O)S$R^{1a}$, —OC(=N$R^{1a}$)N$R^{1b}R^{1c}$, —OC(S)$R^{1a}$, —OC(S)O$R^{1a}$, —OC(S)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^a$C(O)O$R^{1d}$, —N$R^{1a}$C(O)N$R^{1b}R^{1c}$, —N$R^{1a}$C(O)S$R^{1d}$, —N$R^{1a}$C(=N$R^{1d}$)N$R^{1b}R^{1c}$, —N$R^{1a}$C(S)$R^{1d}$, —N$R^{1a}$C(S)O$R^{1d}$, —N$R^{1a}$C(S)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$; or two $R^7$ are linked together to form (a) a bond, —O—, —N$R^8$—, or —S—; or (b) $C_{1-6}$ alkylene, $C_{1-6}$ heteroalkylene, $C_{2-6}$ alkenylene, or $C_{2-6}$ heteroalkenylene, each of which is optionally substituted with one or more substituents Q;

$R^8$ is independently (a) hydrogen or deuterium; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each of which is optionally substituted with one or more substituents Q; or (c) —C(O)$R^{1a}$, —C(O)O$R^{1a}$, —C(O)N$R^{1b}R^{1c}$, —C(O)S$R^{1a}$, —C(N$R^{1a}$)N$R^{1b}R^{1c}$, —C(S)$R^{1a}$, —C(S)O$R^{1a}$, —C(S)N$R^{1b}R^{1c}$, —O$R^{1a}$, —OC(O)$R^{1a}$, —OC(O)O$R^{1a}$, —OC(O)N$R^{1b}R^{1c}$, —OC(O)S$R^{1a}$, —OC(=N$R^{1a}$)N$R^{1b}R^{1c}$, —OC(S)$R^{1a}$, —OC(S)O$R^{1a}$, —OC(S)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(O)S$R^{1d}$, —N$R^{1a}$C(=N$R^{1d}$a)N$R^{1b}R^{1c}$, —N$R^{1a}$C(S)$R^{1d}$, —N$R^{1a}$C(S)O$R^{1d}$, —N$R^{1a}$C(S)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$;

m is an integer of 1, 2, 3, or 4;
n is an integer of 0, 1, 2, 3, 4, 5, 6, or 7; and
$R^3$, $R^4$, $R^5$, $R^{1a}$, $R^{1b}$, $R^{1c}$, and $R^{1d}$ are each as defined herein.

In one embodiment, in Formula III, $R^3$ and $R^5$ are hydrogen. In another embodiment, in Formula III, $R^3$ and $R^5$ are hydrogen; and $R^4$ is methyl, optionally substituted with one or more substituents Q. In yet another embodiment, in Formula III, $R^3$ and $R^5$ are hydrogen; and $R^4$ is —C($R^{4a}$)$_3$, wherein each $R^{4a}$ is independently hydrogen, deuterium, fluoro, or hydroxyl. In yet another embodiment, in Formula III, $R^3$ and $R^5$ are hydrogen; and $R^4$ is methyl.

In one embodiment, in Formula III, $R^3$ and $R^5$ are hydrogen; and $R^4$ is $C_{6-14}$ aryl, optionally substituted with one or more substituents Q. In yet another embodiment, in Formula III, $R^3$ and $R^5$ are hydrogen; and $R^4$ is phenyl, optionally substituted with one or more substituents Q. In yet another embodiment, in Formula III, $R^3$ and $R^5$ are hydrogen; and $R^4$ is phenyl.

In one embodiment, in Formula III, Z is a bond. In another embodiment, in Formula III, Z is a bond; and m is 1 or 2. In yet another embodiment, in Formula III, Z is a bond; m is 1 or 2; and n is 0.

In yet another embodiment, the compound described herein has the structure of Formula IV:

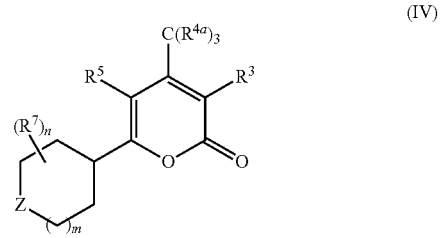

(IV)

or an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof; wherein $R^3$, $R^{4a}$, $R^5$, $R^7$, Z, m, and n are each as defined herein.

In yet another embodiment, the compound described herein has the structure of Formula V:

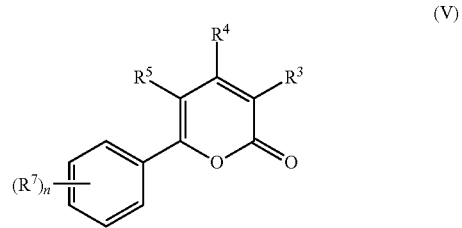

(V)

or an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof; wherein n is an integer of 0, 1, 2, 3, 4, or 5; and $R^3$, $R^4$, $R^5$, and $R^7$ are each as defined herein.

In still another embodiment, the compound described herein has the structure of Formula VI:

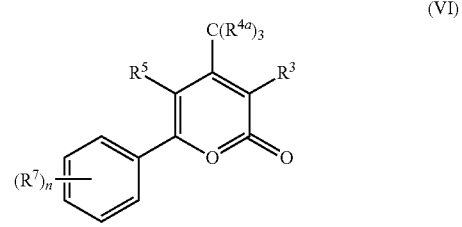

(VI)

or an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof; wherein $R^3$, $R^{4a}$, $R^5$, $R^7$, and n are each as defined herein.

The groups, $R^3$, $R^4$, $R^{4a}$, $R^5$, $R^6$, $R^7$, Z, m, and n in Formulae described herein, including Formulae I to VI, are further defined in the embodiments described herein. All combinations of the embodiments described herein for such groups are within the scope of this disclosure.

In certain embodiments, $R^3$ is hydrogen. In certain embodiments, $R^3$ is deuterium. In certain embodiments, $R^3$ is fluoro.

In certain embodiments, $R^3$ is cyano. In certain embodiments, $R^3$ is halo. In certain embodiments, $R^3$ is chloro. In certain embodiments, $R^3$ is nitro. In certain embodiments, $R^3$ is $C_{1-6}$ alkyl, optionally substituted with one or more substituents Q. In certain embodiments, $R^3$ is $C_{2-6}$ alkenyl, optionally substituted with one or more substituents Q. In certain embodiments, $R^3$ is $C_{2-6}$ alkynyl, optionally substituted with one or more substituents Q. In certain embodiments, $R^3$ is $C_{3-7}$ cycloalkyl, optionally substituted with one or more substituents Q. In certain embodiments, $R^3$ is $C_{6-14}$ aryl, optionally substituted with one or more substituents Q. In certain embodiments, $R^3$ is $C_{7-15}$ aralkyl, optionally substituted with one or more substituents Q. In certain embodiments, $R^3$ is heteroaryl, optionally substituted with one or more substituents Q. In certain embodiments, $R^3$ is heterocyclyl, optionally substituted with one or more substituents Q.

In certain embodiments, $R^3$ is —C(O)$R^{1a}$, wherein $R^{1a}$ is as defined herein. In certain embodiments, $R^3$ is —C(O)O$R^{1a}$, wherein $R^{1a}$ is as defined herein. In certain embodiments, $R^3$ is —C(O)N$R^{1b}R^{1c}$, wherein $R^{1b}$ and $R^{1c}$ are each as defined herein. In certain embodiments, $R^3$ is —C(O)S$R^{1a}$, wherein $R^{1a}$ is as defined herein. In certain embodiments, $R^3$ is —C(N$R^{1a}$)N$R^{1b}R^{1c}$, wherein $R^{1a}$, $R^{1b}$, and $R^{1c}$ are each as defined herein. In certain embodiments, $R^3$ is —C(S)$R^{1a}$, wherein $R^{1a}$ is as defined herein. In certain embodiments, $R^3$ is —C(S)O$R^{1a}$, wherein $R^{1a}$ is as defined herein. In certain embodiments, $R^3$ is —C(S)N$R^{1b}R^c$, wherein $R^{1b}$ and $R^{1c}$ are each as defined herein. In certain embodiments, $R^3$ is —O$R^{1a}$, wherein $R^{1a}$ is as defined herein. In certain embodiments, $R^3$ is —OC(O)$R^{1a}$, wherein $R^{1a}$ is as defined herein. In certain embodiments, $R^3$ is —OC(O)O$R^{1a}$, wherein $R^{1a}$ is as defined herein. In certain embodiments, $R^3$ is —OC(O)N$R^{1b}R^c$, wherein $R^{1b}$ and $R^{1c}$ are each as defined herein. In certain embodiments, $R^3$ is —OC(O)S$R^{1a}$, wherein $R^{1a}$ is as defined herein. In certain embodiments, $R^3$ is —OC(=N$R^{1a}$)N$R^{1b}R^c$, wherein $R^{1a}$, $R^{1b}$, and $R^{1c}$ are each as defined herein. In certain embodiments, $R^3$ is —OC(S)$R^{1a}$, wherein $R^{1a}$ is as defined herein. In certain embodiments, $R^3$ is —OC(S)O$R^{1a}$, wherein $R^{1a}$ is as defined herein. In certain embodiments, $R^3$ is —OC(S)N$R^{1b}R^{1c}$, wherein $R^{1b}$ and $R^{1c}$ are each as defined herein. In certain embodiments, $R^3$ is —OS(O)$R^{1a}$, wherein $R^{1a}$ is as defined herein. In certain embodiments, $R^3$ is —OS(O)$_2R^{1a}$, wherein $R^{1a}$ is as defined herein. In certain embodiments, $R^3$ is —OS(O)N$R^{1b}R^{1c}$, wherein $R^{1b}$ and $R^{1c}$ are each as defined herein. In certain embodiments, $R^3$ is —OS(O)$_2$N$R^{1b}R^{1c}$, wherein $R^{1b}$ and $R^{1c}$ are each as defined herein. In certain embodiments, $R^3$ is —N$R^{1b}R^{1c}$ wherein $R^{1b}$ and $R^{1c}$ are each as defined herein. In certain embodiments, $R^3$ is —N$R^{1a}$C(O)$R^{1d}$, wherein $R^{1a}$ and $R^{1d}$ are each as defined herein. In certain embodiments, $R^3$ is —N$R^{1a}$C(O)O$R^{1d}$, wherein $R^{1a}$ and $R^{1d}$ are each as defined herein. In certain embodiments, $R^3$ is —N$R^{1a}$C(O)N$R^{1b}R^{1c}$ wherein $R^{1a}$, $R^{1b}$, and $R^{1c}$ are each as defined herein. In certain embodiments, $R^3$ is —N$R^{1a}$C(O)S$R^{1d}$, wherein $R^{1a}$ and $R^{1d}$ are each as defined herein. In certain embodiments, $R^3$ is —N$R^{1a}$C(=N$R^{1d}$)N$R^{1b}R^{1c}$ wherein $R^{1a}$, $R^{1b}$, $R^{1c}$, and $R^{1d}$ are each as defined herein. In certain embodiments, $R^3$ is —N$R^{1a}$C(S)$R^{1d}$, wherein $R^{1a}$ and $R^{1d}$ are each as defined herein. In certain embodiments, $R^3$ is —N$R^{1a}$C(S)O$R^{1d}$, wherein $R^{1a}$ and $R^{1d}$ are each as defined herein. In certain embodiments, $R^3$ is —N$R^{1a}$C(S)N$R^{1b}R^{1c}$ wherein $R^{1a}$, $R^{1b}$, and $R^{1c}$ are each as defined herein. In certain embodiments, $R^3$ is —N$R^{1a}$S(O)$R^{1d}$, wherein $R^{1a}$ and $R^{1d}$ are each as defined herein. In certain embodiments, $R^3$ is —N$R^{1a}$S(O)$_2R^{1d}$, wherein $R^{1a}$ and $R^{1d}$ are each as defined herein. In certain embodiments, $R^3$ is —N$R^{1a}$S(O)N$R^{1b}R^{1c}$ wherein $R^{1a}$, $R^{1b}$, and $R^{1c}$ are each as defined herein. In certain embodiments, $R^3$ is —N$R^{1a}$S(O)$_2$N$R^{1b}R^{1c}$ wherein $R^{1a}$, $R^{1b}$, and $R^{1c}$ are each as defined herein. In certain embodiments, $R^3$ is —S$R^{1a}$, wherein $R^{1a}$ is as defined herein. In certain embodiments, $R^3$ is —S(O)$R^{1a}$, wherein $R^{1a}$ is as defined herein. In certain embodiments, $R^3$ is —S(O)$_2R^{1a}$, wherein $R^{1a}$ is as defined herein. In certain embodiments, $R^3$ is —S(O)N$R^{1b}R^{1c}$, wherein $R^{1b}$ and $R^{1c}$ are each as defined herein. In certain embodiments, $R^3$ is —S(O)$_2$N$R^{1b}R^{1c}$, wherein $R^{1b}$ and $R^{1c}$ are each as defined herein.

In certain embodiments, $R^4$ is $C_{1-6}$ alkyl, optionally substituted with one or more substituents Q. In certain embodiments, $R^4$ is —C($R^{4a}$)$_3$, wherein each $R^{4a}$ is independently hydrogen, deuterium, fluoro, or hydroxyl. In certain embodiments, $R^4$ is methyl, optionally substituted with one or more substituents Q. In certain embodiments, $R^4$ is methyl, optionally substituted with one, two, or three deuterium, fluoro, or hydroxyl. In certain embodiments, $R^4$ is —CH$_3$, —CH$_2$D, —CHD$_2$, or —CD3. In certain embodiments, $R^4$ is —CH$_2$F, —CHF$_2$, or —CF$_3$. In certain embodiments, $R^4$ is —CH$_2$OH, —CH(OH)$_2$ (i.e., CHO), or —C(OH)$_3$ (i.e., COOH). In certain embodiments, $R^4$ is hydrogen. In certain embodiments, $R^4$ is deuterium. In certain embodiments, $R^4$ is cyano. In certain embodiments, $R^4$ is halo. In certain embodiments, $R^4$ is fluoro or chloro. In certain embodiments, $R^4$ is nitro. In certain embodiments, $R^4$ is $C_{2-6}$ alkenyl, optionally substituted with one or more substituents Q. In certain embodiments, $R^4$ is $C_{2-6}$ alkynyl, optionally substituted with one or more substituents Q. In certain embodiments, $R^4$ is $C_{3-7}$ cycloalkyl, optionally substituted with one or more substituents Q. In certain embodiments, $R^4$ is monocyclic $C_{3-7}$ cycloalkyl, optionally substituted with one or more substituents Q. In certain embodiments, $R^4$ is cyclohexyl, optionally substituted with one or more substituents Q. In certain embodiments, $R^4$ is $C_{6-14}$ aryl, optionally substituted with one or more substituents Q. In certain embodiments, $R^4$ is monocyclic $C_{6-14}$ aryl, optionally substituted with one or more substituents Q. In certain embodiments, $R^4$ is phenyl, optionally substituted with one or more substituents Q. In certain embodiments, $R^4$ is $C_{7-15}$ aralkyl, optionally substituted with one or more substituents Q. In certain embodiments, $R^4$ is heteroaryl, optionally substituted with one or more substituents Q. In certain embodiments, $R^4$ is monocyclic heteroaryl, optionally substituted with one or more substituents Q. In certain embodiments, $R^4$ is 5 to 7 membered heteroaryl, optionally substituted with one or more substituents Q. In certain embodiments, $R^4$ is heterocyclyl, optionally substituted with one or more substituents Q. In certain embodiments, $R^4$ is monocyclic heterocyclyl, optionally substituted with one or more substituents Q. In certain embodiments, $R^4$ is 5 to 7 membered heterocyclyl, optionally substituted with one or more substituents Q.

In certain embodiments, $R^4$ is —C(O)$R^{1a}$, wherein $R^{1a}$ is as defined herein. In certain embodiments, $R^4$ is —C(O)O$R^{1a}$, wherein $R^{1a}$ is as defined herein. In certain embodiments, $R^4$ is —C(O)N$R^{1b}R^c$, wherein $R^{1b}$ and $R^{1c}$ are each as defined herein. In certain embodiments, $R^4$ is —C(O)S$R^{1a}$, wherein $R^{1a}$ is as defined herein. In certain embodiments, $R^4$ is —C($NR^{1a}$)$NR^{1b}R^c$, wherein $R^{1a}$, $R^{1b}$, and $R^{1c}$ are each as defined herein. In certain embodiments, $R^4$ is —C(S)$R^{1a}$, wherein $R^{1a}$ is as defined herein. In certain embodiments, $R^4$ is —C(S)O$R^{1a}$, wherein $R^{1a}$ is as defined herein. In certain embodiments, $R^4$ is —C(S)$NR^{1b}R^c$, wherein $R^{1b}$ and $R^{1c}$ are each as defined herein. In certain embodiments, $R^4$ is —O$R^{1a}$, wherein $R^{1a}$ is as defined herein. In certain embodiments, $R^4$ is —OC(O)$R^{1a}$, wherein $R^{1a}$ is as defined herein. In certain embodiments, $R^4$ is —OC(O)O$R^{1a}$, wherein $R^{1a}$ is as defined herein. In certain embodiments, $R^4$ is —OC(O)$NR^{1b}R^c$, wherein $R^{1b}$ and $R^{1c}$ are each as defined herein. In certain embodiments, $R^4$ is —OC(O)S$R^{1a}$, wherein $R^{1a}$ is as defined herein. In certain embodiments, $R^4$ is —OC(=$NR^{1a}$)$NR^{1b}R^{1c}$, wherein $R^{1a}$, $R^{1b}$, and $R^{1c}$ are each as defined herein. In certain embodiments, $R^4$ is —OC(S)$R^{1a}$, wherein $R^{1a}$ is as defined herein. In certain embodiments, $R^4$ is —OC(S)O$R^{1a}$, wherein $R^{1a}$ is as defined herein. In certain embodiments, $R^4$ is —OC(S)$NR^{1b}R^{1c}$, wherein $R^{1b}$ and $R^{1c}$ are each as defined herein. In certain embodiments, $R^4$ is —OS(O)$R^{1a}$, wherein $R^{1a}$ is as defined herein. In certain embodiments, $R^4$ is —OS(O)$_2R^{1a}$, wherein $R^{1a}$ is as defined herein. In certain embodiments, $R^4$ is —OS(O)$NR^{1b}R^{1c}$, wherein $R^{1b}$ and $R^{1c}$ are each as defined herein. In certain embodiments, $R^4$ is —OS(O)$_2NR^{1b}R^{1c}$, wherein $R^{1b}$ and $R^{1c}$ are each as defined herein. In certain embodiments, $R^4$ is —$NR^{1b}R^{1c}$ wherein $R^{1b}$ and $R^{1c}$ are each as defined herein. In certain embodiments, $R^4$ is —$NR^{1a}$C(O)$R^{1d}$, wherein $R^{1a}$ and $R^{1d}$ are each as defined herein. In certain embodiments, $R^4$ is —$NR^{1a}$C(O)O$R^{1d}$ wherein $R^{1a}$ and $R^{1d}$ are each as defined herein. In certain embodiments, $R^4$ is —$NR^{1a}$C(O)$NR^{1b}R^{1c}$ wherein $R^{1a}$, $R^{1b}$, and $R^{1c}$ are each as defined herein. In certain embodiments, $R^4$ is —$NR^{1a}$C(O)S$R^{1d}$ wherein $R^{1a}$ and $R^{1d}$ are each as defined herein. In certain embodiments, $R^4$ is —$NR^{1a}$C(=$NR^{1d}$)$NR^{1b}R^{1c}$ wherein $R^{1a}$, $R^{1b}$, $R^{1c}$, and $R^{1d}$ are each as defined herein. In certain embodiments, $R^4$ is —$NR^{1a}$C(S)$R^{1d}$, wherein $R^{1a}$ and $R^{1d}$ are each as defined herein. In certain embodiments, $R^4$ is —$NR^{1a}$C(S)O$R^{1d}$, wherein $R^{1a}$ and $R^{1d}$ are each as defined herein. In certain embodiments, $R^4$ is —$NR^{1a}$C(S)$NR^{1b}R^{1c}$ wherein $R^{1a}$, $R^{1b}$, and $R^{1c}$ are each as defined herein. In certain embodiments, $R^4$ is —$NR^{1a}$S(O)$R^{1d}$, wherein $R^{1a}$ and $R^{1d}$ are each as defined herein. In certain embodiments, $R^4$ is —$NR^{1a}$S(O)$_2R^{1d}$, wherein $R^{1a}$ and $R^{1d}$ are each as defined herein. In certain embodiments, $R^4$ is —$NR^{1a}$S(O)$NR^{1b}R^{1c}$ wherein $R^{1a}$, $R^{1b}$, and $R^{1c}$ are each as defined herein. In certain embodiments, $R^4$ is —$NR^{1a}$S(O)$_2NR^{1b}R^{1c}$ wherein $R^{1a}$, $R^{1b}$, and $R^{1c}$ are each as defined herein. In certain embodiments, $R^4$ is —S$R^{1a}$, wherein $R^{1a}$ is as defined herein. In certain embodiments, $R^4$ is —S(O)$R^{1a}$, wherein $R^{1a}$ is as defined herein. In certain embodiments, $R^4$ is —S(O)$_2R^{1a}$, wherein $R^{1a}$ is as defined herein. In certain embodiments, $R^4$ is —S(O)$NR^{1b}R^c$, wherein $R^{1b}$ and $R^{1c}$ are each as defined herein. In certain embodiments, $R^4$ is —S(O)$_2NR^{1b}R^c$, wherein $R^{1b}$ and $R^{1c}$ are each as defined herein.

In certain embodiments, each $R^{4a}$ is independently hydrogen. In certain embodiments, each $R^{4a}$ is independently deuterium. In certain embodiments, each $R^{4a}$ is independently halo. In certain embodiments, each $R^{4a}$ is independently fluoro. In certain embodiments, each $R^{4a}$ is independently hydroxyl.

In certain embodiments, $R^5$ is hydrogen. In certain embodiments, $R^5$ is deuterium. In certain embodiments, $R^5$ is fluoro.

In certain embodiments, $R^5$ is cyano. In certain embodiments, $R^5$ is halo. In certain embodiments, $R^5$ is chloro. In certain embodiments, $R^5$ is nitro. In certain embodiments, $R^5$ is $C_{1-6}$ alkyl, optionally substituted with one or more substituents Q. In certain embodiments, $R^5$ is $C_{2-6}$ alkenyl, optionally substituted with one or more substituents Q. In certain embodiments, $R^5$ is $C_{2-6}$ alkynyl, optionally substituted with one or more substituents Q. In certain embodiments, $R^5$ is $C_{3-7}$ cycloalkyl, optionally substituted with one or more substituents Q. In certain embodiments, $R^5$ is $C_{6-14}$ aryl, optionally substituted with one or more substituents Q. In certain embodiments, $R^5$ is $C_{7-15}$ aralkyl, optionally substituted with one or more substituents Q. In certain embodiments, $R^5$ is heteroaryl, optionally substituted with one or more substituents Q. In certain embodiments, $R^5$ is heterocyclyl, optionally substituted with one or more substituents Q.

In certain embodiments, $R^5$ is —C(O)$R^{1a}$, wherein $R^{1a}$ is as defined herein. In certain embodiments, $R^5$ is —C(O)O$R^{1a}$, wherein $R^{1a}$ is as defined herein. In certain embodiments, $R^5$ is —C(O)$NR^{1b}R^c$, wherein $R^{1b}$ and $R^{1c}$ are each as defined herein. In certain embodiments, $R^5$ is —C(O)S$R^{1a}$, wherein $R^{1a}$ is as defined herein. In certain embodiments, $R^5$ is —C($NR^{1a}$)$NR^{1b}R^c$, wherein $R^{1a}$, $R^{1b}$, and $R^{1c}$ are each as defined herein. In certain embodiments, $R^5$ is —C(S)$R^{1a}$, wherein $R^{1a}$ is as defined herein. In certain embodiments, $R^5$ is —C(S)O$R^{1a}$, wherein $R^{1a}$ is as defined herein. In certain embodiments, $R^5$ is —C(S)$NR^{1b}R^c$, wherein $R^{1b}$ and $R^{1c}$ are each as defined herein. In certain embodiments, $R^5$ is —O$R^{1a}$, wherein $R^{1a}$ is as defined herein. In certain embodiments, $R^5$ is —OC(O)$R^{1a}$, wherein $R^{1a}$ is as defined herein. In certain embodiments, $R^5$ is —OC(O)O$R^{1a}$, wherein $R^{1a}$ is as defined herein. In certain embodiments, $R^5$ is —OC(O)$NR^{1b}R^{1c}$, wherein $R^{1b}$ and $R^{1c}$ are each as defined herein. In certain embodiments, $R^5$ is —OC(O)S$R^{1a}$, wherein $R^{1a}$ is as defined herein. In certain embodiments, $R^5$ is —OC(=$NR^{1a}$)$NR^{1b}R^{1c}$, wherein $R^{1a}$, $R^{1b}$, and $R^{1c}$ are each as defined herein. In certain embodiments, $R^5$ is —OC(S)$R^{1a}$, wherein $R^{1a}$ is as defined herein. In certain embodiments, $R^5$ is —OC(S)O$R^{1a}$, wherein $R^{1a}$ is as defined herein. In certain embodiments, $R^5$ is —OC(S)$NR^{1b}R^{1c}$, wherein $R^{1b}$ and $R^{1c}$ are each as defined herein. In certain embodiments, $R^5$ is —OS(O)$R^{1a}$, wherein $R^{1a}$ is as defined herein. In certain embodiments, $R^5$ is —OS(O)$_2R^{1a}$, wherein $R^{1a}$ is as defined herein. In certain embodiments, $R^5$ is —OS(O)$NR^{1b}R^{1c}$, wherein $R^{1b}$ and $R^{1c}$ are each as defined herein. In certain embodiments, $R^5$ is —OS(O)$_2NR^{1b}R^{1c}$, wherein $R^{1b}$ and $R^{1c}$ are each as defined herein. In certain embodiments, $R^5$ is —$NR^{1b}R^{1c}$, wherein $R^{1b}$ and $R^{1c}$ are each as defined herein. In certain embodiments, $R^5$ is —$NR^{1a}$C(O)$R^{1d}$, wherein $R^{1a}$ and $R^{1d}$ are each as defined herein. In certain embodiments, $R^5$ is —$NR^{1a}$C(O)O$R^{1d}$, wherein $R^{1a}$ and $R^{1d}$ are each as defined herein. In certain embodiments, $R^5$ is —$NR^{1a}$C(O)$NR^{1b}R^{1c}$ wherein $R^{1a}$, $R^{1b}$, and $R^{1c}$ are each as defined herein. In certain embodiments, $R^5$ is —$NR^{1a}$C(O)S$R^{1d}$, wherein $R^{1a}$ and $R^{1d}$ are each as defined herein. In certain embodiments, $R^5$ is —$NR^{1a}$C(=$NR^{1d}$)$NR^{1b}R^{1c}$ wherein $R^{1a}$, $R^{1b}$, $R^{1c}$, and $R^{1d}$ are each as defined herein. In certain embodiments, $R^5$ is —$NR^{1a}$C(S)$R^{1d}$, wherein $R^{1a}$ and $R^{1d}$ are each as defined herein. In certain embodiments, $R^5$ is —$NR^{1a}$C(S)O$R^{1d}$, wherein $R^{1a}$ and $R^{1d}$ are each as defined herein. In certain embodiments, $R^5$ is —$NR^{1a}$C(S)$NR^{1b}R^{1c}$ wherein $R^{1a}$, $R^{1b}$, and $R^{1c}$ are each as defined herein. In certain embodiments, $R^5$ is —$NR^{1a}$S(O)$R^{1d}$, wherein $R^{1a}$ and $R^{1d}$ are each as defined herein. In certain embodiments, $R^5$ is —$NR^{1a}$S(O)$_2R^{1d}$, wherein $R^{1a}$ and $R^{id}$ are each as defined herein. In certain embodiments, $R^5$ is —$NR^{1a}$S(O)$NR^{1b}R^{1c}$ wherein $R^{1a}$, $R^{1b}$, and $R^{1c}$ are each as defined herein. In certain embodiments, $R^5$ is —$NR^{1a}$S(o)$_2NR^{1b}R^{1c}$ wherein $R^{1a}$, $R^{1b}$, and $R^{1c}$ are each as defined herein. In certain embodiments, $R^5$ is —$SR^{1a}$, wherein $R^{1a}$ is as defined herein. In certain embodiments, $R^5$ is —$S(O)R^{1a}$, wherein $R^{1a}$ is as defined herein. In certain embodiments, $R^5$ is —$S(O)_2R^{1a}$, wherein $R^{1a}$ is as defined herein. In certain embodiments, $R^5$ is —$S(O)NR^{1b}R^{1c}$, wherein $R^{1b}$ and $R^{1c}$ are each as defined herein. In certain embodiments, $R^5$ is —$S(O)_2NR^{1b}R^{1c}$, wherein $R^{1b}$ and $R^{1c}$ are each as defined herein.

In certain embodiments, $R^6$ is $C_{3-7}$ cycloalkyl, optionally substituted with one or more substituents Q. In certain embodiments, $R^6$ is monocyclic $C_{3-7}$ cycloalkyl, optionally substituted with one or more substituents Q. In certain embodiments, $R^6$ is cyclohexyl, optionally substituted with one or more substituents Q. In certain embodiments, $R^6$ is $C_{6-14}$ aryl, optionally substituted with one or more substituents Q. In certain embodiments, $R^6$ is monocyclic $C_{6-14}$ aryl, optionally substituted with one or more substituents Q. In certain embodiments, $R^6$ is phenyl, optionally substituted with one or more substituents Q. In certain embodiments, $R^6$ is $C_{7-15}$ aralkyl, optionally substituted with one or more substituents Q. In certain embodiments, $R^6$ is heteroaryl, optionally substituted with one or more substituents Q. In certain embodiments, $R^6$ is monocyclic heteroaryl, optionally substituted with one or more substituents Q. In certain embodiments, $R^6$ is 5 to 7 membered heteroaryl, optionally substituted with one or more substituents Q. In certain embodiments, $R^6$ is heterocyclyl, optionally substituted with one or more substituents Q. In certain embodiments, $R^6$ is monocyclic heterocyclyl, optionally substituted with one or more substituents Q. In certain embodiments, $R^6$ is 5 to 7 membered heterocyclyl, optionally substituted with one or more substituents Q.

In certain embodiments, $R^6$ is hydrogen. In certain embodiments, $R^6$ is deuterium. In certain embodiments, $R^6$ is cyano. In certain embodiments, $R^6$ is halo. In certain embodiments, $R^6$ is fluoro or chloro. In certain embodiments, $R^6$ is nitro. In certain embodiments, $R^6$ is $C_{2-6}$ alkenyl, optionally substituted with one or more substituents Q. In certain embodiments, $R^6$ is $C_{2-6}$ alkynyl, optionally substituted with one or more substituents Q.

In certain embodiments, $R^6$ is —$C(O)R^{1a}$, wherein $R^{1a}$ is as defined herein. In certain embodiments, $R^6$ is —$C(O)OR^{1a}$, wherein $R^{1a}$ is as defined herein. In certain embodiments, $R^6$ is —$C(O)NR^{1b}R^c$, wherein $R^{1b}$ and $R^{1c}$ are each as defined herein. In certain embodiments, $R^6$ is —$C(O)SR^{1a}$, wherein $R^{1a}$ is as defined herein. In certain embodiments, $R^6$ is —$C(NR^{1a})NR^{1b}R^c$, wherein $R^{1a}$, $R^{1b}$, and $R^{1c}$ are each as defined herein. In certain embodiments, $R^6$ is —$C(S)R^{1a}$, wherein $R^{1a}$ is as defined herein. In certain embodiments, $R^6$ is —$C(S)OR^{1a}$, wherein $R^{1a}$ is as defined herein. In certain embodiments, $R^6$ is —$C(S)NR^{1b}R^c$, wherein $R^{1b}$ and $R^{1c}$ are each as defined herein. In certain embodiments, $R^6$ is —$OR^{1a}$, wherein $R^{1a}$ is as defined herein. In certain embodiments, $R^6$ is —$OC(O)R^{1a}$, wherein $R^{1a}$ is as defined herein. In certain embodiments, $R^6$ is —$OC(O)OR^{1a}$, wherein $R^{1a}$ is as defined herein. In certain embodiments, $R^6$ is —$OC(O)NR^{1b}R^c$, wherein $R^{1b}$ and $R^{1c}$ are each as defined herein. In certain embodiments, $R^6$ is —$OC(O)SR^{1a}$, wherein $R^{1a}$ is as defined herein. In certain embodiments, $R^6$ is —$OC(=NR^{1a})NR^{1b}R^{1c}$, wherein $R^{1a}$, $R^{1b}$, and $R^{1c}$ are each as defined herein. In certain embodiments, $R^6$ is —$OC(S)R^{1a}$, wherein $R^{1a}$ is as defined herein. In certain embodiments, $R^6$ is —$OC(S)OR^{1a}$, wherein $R^{1a}$ is as defined herein. In certain embodiments, $R^6$ is —$OC(S)NR^{1b}R^{1c}$, wherein $R^{1b}$ and $R^{1c}$ are each as defined herein. In certain embodiments, $R^6$ is —$OS(O)R^{1a}$, wherein $R^{1a}$ is as defined herein. In certain embodiments, $R^6$ is —$OS(O)_2R^{1a}$, wherein $R^{1a}$ is as defined herein. In certain embodiments, $R^6$ is —$OS(O)NR^{1b}R^{1c}$, wherein $R^{1b}$ and $R^{1c}$ are each as defined herein. In certain embodiments, $R^6$ is —$OS(O)_2NR^{1b}R^{1c}$, wherein $R^{1b}$ and $R^{1c}$ are each as defined herein. In certain embodiments, $R^6$ is —$NR^{1b}R^{1c}$, wherein $R^{1b}$ and $R^{1c}$ are each as defined herein. In certain embodiments, $R^6$ is —$NR^{1a}C(O)R^{1d}$, wherein $R^{1a}$ and $R^{1d}$ are each as defined herein. In certain embodiments, $R^6$ is —$NR^{1a}C(O)OR^{1d}$ wherein $R^{1a}$ and $R^{1d}$ are each as defined herein. In certain embodiments, $R^6$ is —$NR^{1a}C(O)NR^{1b}R^{1c}$ wherein $R^{1a}$, $R^{1b}$, and $R^{1c}$ are each as defined herein. In certain embodiments, $R^6$ is —$NR^{1a}C(O)SR^{1d}$ wherein $R^{1a}$ and $R^{1d}$ are each as defined herein. In certain embodiments, $R^6$ is —$NR^{1a}C(=NR^{1d})NR^{1b}R^{1c}$ wherein $R^{1a}$, $R^{1b}$, $R^{1c}$, and $R^{1d}$ are each as defined herein. In certain embodiments, $R^6$ is —$NR^{1a}C(S)R^{1d}$, wherein $R^{1a}$ and $R^{1d}$ are each as defined herein. In certain embodiments, $R^6$ is —$NR^{1a}C(S)OR^{1d}$, wherein $R^{1a}$ and $R^{1d}$ are each as defined herein. In certain embodiments, $R^6$ is —$NR^{1a}C(S)NR^{1b}R^{1c}$ wherein $R^{1a}$, $R^{1b}$, and $R^{1c}$ are each as defined herein. In certain embodiments, $R^6$ is —$NR^{1a}S(O)R^{1d}$, wherein $R^{1a}$ and $R^{1d}$ are each as defined herein. In certain embodiments, $R^6$ is —$NR^{1a}S(O)_2R^{1d}$, wherein $R^{1a}$ and $R^{1d}$ are each as defined herein. In certain embodiments, $R^6$ is —$NR^{1a}S(O)NR^{1b}R^{1c}$ wherein $R^{1a}$, $R^{1b}$, and $R^{1c}$ are each as defined herein. In certain embodiments, $R^6$ is —$NR^{1a}S(o)_2NR^{1b}R^{1c}$ wherein $R^{1a}$, $R^{1b}$, and $R^{1c}$ are each as defined herein. In certain embodiments, $R^6$ is —$SR^{1a}$, wherein $R^{1a}$ is as defined herein. In certain embodiments, $R^6$ is —$S(O)R^{1a}$, wherein $R^{1a}$ is as defined herein. In certain embodiments, $R^6$ is —$S(O)_2R^{1a}$, wherein $R^{1a}$ is as defined herein. In certain embodiments, $R^6$ is —$S(O)NR^{1b}R^{1c}$, wherein $R^{1b}$ and $R^{1c}$ are each as defined herein. In certain embodiments, $R^6$ is —$S(O)_2NR^{1b}R^{1c}$, wherein $R^{1b}$ and $R^{1c}$ are each as defined herein.

In certain embodiments, $R^7$ is deuterium. In certain embodiments, $R^7$ is halo. In certain embodiments, $R^7$ is fluoro or chloro. In certain embodiments, $R^7$ is cyano. In certain embodiments, $R^7$ is nitro. In certain embodiments, $R^7$ is guanidine. In certain embodiments, $R^7$ is $C_{1-6}$ alkyl, optionally substituted with one or more substituents Q. In certain embodiments, $R^7$ is methyl, ethyl, propyl (e.g., n-propyl or isopropyl), butyl (e.g., n-butyl, 2-butyl, isobutyl, or t-butyl), pentyl (e.g., n-pentyl, 2-pentyl, 3-pentyl, 2-methylbutyl, 3-methylbutyl, 1,1-dimethylpropyl, 1,2-dimethylpropyl, or 2,2-dimethylpropyl). In certain embodiments, $R^7$ is methyl, —$CH_2D$, —$CHD_2$, or —$CD3$. In certain embodiments, $R^7$ is $C_{2-6}$ alkenyl, optionally substituted with one or more substituents Q. In certain embodiments, $R^7$ is $C_{2-6}$ alkynyl, optionally substituted with one or more substituents Q. In certain embodiments, $R^7$ is $C_{3-7}$ cycloalkyl, optionally substituted with one or more substituents Q. In certain embodiments, $R^7$ is $C_{6-14}$ aryl, optionally substituted with one or more substituents Q. In certain embodiments, $R^7$ is $C_{7-15}$ aralkyl, optionally substituted with one or more substituents Q. In certain embodiments, $R^7$ is heteroaryl, optionally substituted with one or more substituents Q. In certain embodiments, $R^7$ is heterocyclyl, optionally substituted with one or more substituents Q.

In certain embodiments, $R^7$ is —$C(O)R^{1a}$, wherein $R^{1a}$ is as defined herein. In certain embodiments, $R^7$ is —$C(O)OR^{1a}$, wherein $R^{1a}$ is as defined herein. In certain embodiments, $R^7$ is —$C(O)NR^{1b}R^c$, wherein $R^{1b}$ and $R^{1c}$ are each as defined herein. In certain embodiments, $R^7$ is —$C(O)SR^{1a}$, wherein $R^{1a}$ is as defined herein. In certain embodiments, $R^7$ is —$C(NR^{1a})NR^{1b}R^c$, wherein $R^{1a}$, $R^{1b}$, and $R^{1c}$ are each as defined herein. In certain embodiments, $R^7$ is —$C(S)R^{1a}$, wherein $R^{1a}$ is as defined herein. In certain embodiments, $R^7$ is —C(S)$OR^{1a}$, wherein $R^{1a}$ is as defined herein. In certain embodiments, $R^7$ is —C(S)$NR^{1b}R^c$, wherein $R^{1b}$ and $R^{1c}$ are each as defined herein. In certain embodiments, $R^7$ is —$OR^{1a}$, wherein $R^{1a}$ is as defined herein. In certain embodiments, $R^7$ is —OC(O)$R^{1a}$, wherein $R^{1a}$ is as defined herein. In certain embodiments, $R^7$ is —OC(O)$OR^{1a}$, wherein $R^{1a}$ is as defined herein. In certain embodiments, $R^7$ is —OC(O)$NR^{1b}R^c$, wherein $R^{1b}$ and $R^{1c}$ are each as defined herein. In certain embodiments, $R^7$ is —OC(O)$SR^{1a}$, wherein $R^{1a}$ is as defined herein. In certain embodiments, $R^7$ is —OC(=$NR^{1a}$)$NR^{1b}R^c$, wherein $R^{1a}$, $R^{1b}$, and $R^{1c}$ are each as defined herein. In certain embodiments, $R^7$ is —OC(S)$R^{1a}$, wherein $R^{1a}$ is as defined herein. In certain embodiments, $R^7$ is —OC(S)$OR^{1a}$, wherein $R^{1a}$ is as defined herein. In certain embodiments, $R^7$ is —OC(S)$NR^{1b}R^{1c}$, wherein $R^{1b}$ and $R^{1c}$ are each as defined herein. In certain embodiments, $R^7$ is —OS(O)$R^{1a}$, wherein $R^{1a}$ is as defined herein. In certain embodiments, $R^7$ is —OS(O)$_2R^{1a}$, wherein $R^{1a}$ is as defined herein. In certain embodiments, $R^7$ is —OS(O)$NR^{1b}R^{1c}$, wherein $R^{1b}$ and $R^{1c}$ are each as defined herein. In certain embodiments, $R^7$ is —OS(O)$_2NR^{1b}R^{1c}$, wherein $R^{1b}$ and $R^{1c}$ are each as defined herein. In certain embodiments, $R^7$ is —$NR^{1b}R^{1c}$ wherein $R^{1b}$ and $R^{1c}$ are each as defined herein. In certain embodiments, $R^7$ is —$NR^{1a}$C(O)$R^{1d}$, wherein $R^{1a}$ and $R^{1d}$ are each as defined herein. In certain embodiments, $R^7$ is —$NR^{1a}$C(O)$OR^{1d}$, wherein $R^{1a}$ and $R^{1d}$ are each as defined herein. In certain embodiments, $R^7$ is —$NR^{1a}$C(O)$NR^{1b}R^{1c}$, wherein $R^{1a}$, $R^{1b}$, and $R^{1c}$ are each as defined herein. In certain embodiments, $R^7$ is —$NR^{1a}$C(O)$SR^{1d}$, wherein $R^{1a}$ and $R^{1d}$ are each as defined herein. In certain embodiments, $R^7$ is —$NR^{1a}$C(=$NR^{1d}$)$NR^{1b}R^{1c}$ wherein $R^{1a}$, $R^{1b}$, $R^{1c}$, and $R^{1d}$ are each as defined herein. In certain embodiments, $R^7$ is —$NR^{1a}$C(S)$R^{1d}$, wherein $R^{1a}$ and $R^{1d}$ are each as defined herein. In certain embodiments, $R^7$ is —$NR^{1a}$C(S)$OR^{1d}$, wherein $R^{1a}$ and $R^{1d}$ are each as defined herein. In certain embodiments, $R^7$ is —$NR^{1a}$C(S)$NR^{1b}R^{1c}$ wherein $R^{1a}$, $R^{1b}$, and $R^{1c}$ are each as defined herein. In certain embodiments, $R^7$ is —$NR^{1a}$S(O)$R^{1d}$, wherein $R^{1a}$ and $R^{1d}$ are each as defined herein. In certain embodiments, $R^7$ is —$NR^{1a}$S(O)$_2R^{1d}$, wherein $R^{1a}$ and $R^{id}$ are each as defined herein. In certain embodiments, $R^7$ is —$NR^{1a}$S(O)$NR^{1b}R^{1c}$ wherein $R^{1a}$, $R^{1b}$, and $R^{1c}$ are each as defined herein. In certain embodiments, $R^7$ is —$NR^{1a}$S(o)$_2NR^{1b}R^{1c}$ wherein $R^{1a}$, $R^{1b}$, and $R^{1c}$ are each as defined herein. In certain embodiments, $R^7$ is —$SR^{1a}$, wherein $R^{1a}$ is as defined herein. In certain embodiments, $R^7$ is —S(O)$R^{1a}$, wherein $R^{1a}$ is as defined herein. In certain embodiments, $R^7$ is —S(O)$_2R^{1a}$, wherein $R^{1a}$ is as defined herein. In certain embodiments, $R^7$ is —S(O)$NR^{1b}R^{1c}$, wherein $R^{1b}$ and $R^{1c}$ are each as defined herein. In certain embodiments, $R^7$ is —S(O)$_2NR^{1b}R^{1c}$, wherein $R^{1b}$ and $R^{1c}$ are each as defined herein.

In certain embodiments, two $R^7$ are linked together to form a bond. In certain embodiments, two $R^7$ are linked together to form —O—. In certain embodiments, two $R^7$ are linked together to form —$NR^8$—, where $R^8$ is as defined herein. In certain embodiments, two $R^7$ are linked together to form —S—. In certain embodiments, two $R^7$ are linked together to form $C_{1-6}$ alkylene, optionally substituted with one or more substituents Q. In certain embodiments, two $R^7$ are linked together to form methylene, ethylene, or propylene, each optionally substituted with one or more substituents Q. In certain embodiments, two $R^7$ are linked together to form $C_{1-6}$ heteroalkylene, optionally substituted with one or more substituents Q. In certain embodiments, two $R^7$ are linked together to form $C_{2-6}$ alkenylene, optionally substituted with one or more substituents Q. In certain embodiments, two $R^7$ are linked together to form $C_{2-6}$ heteroalkenylene, optionally substituted with one or more substituents Q. In certain embodiments, two $R^7$ are linked together to form a fused ring. In certain embodiments, two $R^7$ are linked together to form a bridged ring. In certain embodiments, two $R^7$ are linked together to form a spiro ring.

In certain embodiments, Z is a bond. In certain embodiments, Z is —O—. In certain embodiments, Z is —S—. In certain embodiments, Z is —S(O)—. In certain embodiments, Z is —S(O$_2$)—. In certain embodiments, Z is —N(R')—, where $R^8$ is as defined herein. In certain embodiments, Z is —NH—. In certain embodiments, Z is —N(C(O)$R^{1a}$)—, where $R^{1a}$ is as defined herein. In certain embodiments, Z is —N(C(O)$C_{1-6}$ alkyl)-. In certain embodiments, Z is —N(C(O)$CH_3$)—.

In certain embodiments, m is 1. In certain embodiments, m is 2. In certain embodiments, m is 3. In certain embodiments, m is 4.

In certain embodiments, n is 0. In certain embodiments, n is 1. In certain embodiments, n is 2. In certain embodiments, n is 3. In certain embodiments, n is 4. In certain embodiments, n is 5. In certain embodiments, n is 6. In certain embodiments, n is 7.

In one embodiment, provided herein is a pharmaceutical composition, comprising a compound selected from the group consisting of:

6-cyclohexyl-4-methyl-2H-pyran-2-one (A1),
6-cyclohexyl-4-phenyl-2H-pyran-2-one (A2), and
4,6-diphenyl-2H-pyran-2-one (A3);

and tautomers and isotopic variants thereof; and pharmaceutically acceptable salts, solvates, hydrates, and prodrugs thereof; and a pharmaceutically acceptable excipient.

In certain embodiments, the compound described herein is deuterium-enriched. In certain embodiments, the compound described herein is carbon-13 enriched. In certain embodiments, the compound described herein is carbon-14 enriched. In certain embodiments, the compound described herein contains one or more less prevalent isotopes for other elements, including, but not limited to, $^{15}$N for nitrogen; $^{17}$O or $^{18}$O for oxygen, and $^{33}$S, $^{34}$S, or $^{36}$S for sulfur.

In certain embodiments, the compound described herein has an isotopic enrichment factor of no less than about 5, no less than about 10, no less than about 20, no less than about 30, no less than about 40, no less than about 50, no less than about 60, no less than about 70, no less than about 80, no less than about 90, no less than about 100, no less than about 200, no less than about 500, no less than about 1,000, no less than about 2,000, no less than about 5,000, or no less than about 10,000. In any events, however, an isotopic enrichment factor for a specified isotope is no greater than the maximum isotopic enrichment factor for the specified isotope, which is the isotopic enrichment factor when a compound at a given position is 100% enriched with the specified isotope. Thus, the maximum isotopic enrichment factor is different for different isotopes. The maximum isotopic enrichment factor is 6410 for deuterium and 90 for carbon-13.

In certain embodiments, the compound described herein has a deuterium enrichment factor of no less than about 64 (about 1% deuterium enrichment), no less than about 130 (about 2% deuterium enrichment), no less than about 320 (about 5% deuterium enrichment), no less than about 640 (about 10% deuterium enrichment), no less than about 1,300 (about 20% deuterium enrichment), no less than about 3,200 (about 50% deuterium enrichment), no less than about 4,800 (about 75% deuterium enrichment), no less than about 5,130 (about 80% deuterium enrichment), no less than about 5,450 (about 85% deuterium enrichment), no less than about 5,770

(about 90% deuterium enrichment), no less than about 6,090 (about 95% deuterium enrichment), no less than about 6,220 (about 97% deuterium enrichment), no less than about 6,280 (about 98% deuterium enrichment), no less than about 6,350 (about 99% deuterium enrichment), or no less than about 6,380 (about 99.5% deuterium enrichment). The deuterium enrichment can be determined using conventional analytical methods known to one of ordinary skill in the art, including mass spectrometry and nuclear magnetic resonance spectroscopy.

In certain embodiments, the compound described herein has a carbon-13 enrichment factor of no less than about 1.8 (about 2% carbon-13 enrichment), no less than about 4.5 (about 5% carbon-13 enrichment), no less than about 9 (about 10% carbon-13 enrichment), no less than about 18 (about 20% carbon-13 enrichment), no less than about 45 (about 50% carbon-13 enrichment), no less than about 68 (about 75% carbon-13 enrichment), no less than about 72 (about 80% carbon-13 enrichment), no less than about 77 (about 85% carbon-13 enrichment), no less than about 81 (about 90% carbon-13 enrichment), no less than about 86 (about 95% carbon-13 enrichment), no less than about 87 (about 97% carbon-13 enrichment), no less than about 88 (about 98% carbon-13 enrichment), no less than about 89 (about 99% carbon-13 enrichment), or no less than about 90 (about 99.5% carbon-13 enrichment). The carbon-13 enrichment can be determined using conventional analytical methods known to one of ordinary skill in the art, including mass spectrometry and nuclear magnetic resonance spectroscopy.

In certain embodiments, at least one of the atoms of the compound described herein, as specified as isotopically enriched, has isotopic enrichment of no less than about 1%, no less than about 2%, no less than about 5%, no less than about 10%, no less than about 20%, no less than about 50%, no less than about 70%, no less than about 80%, no less than about 90%, or no less than about 98%. In certain embodiments, the atoms of the compound described herein, as specified as isotopically enriched, have isotopic enrichment of no less than about 1%, no less than about 2%, no less than about 5%, no less than about 10%, no less than about 20%, no less than about 50%, no less than about 70%, no less than about 80%, no less than about 90%, or no less than about 98%. In any events, the isotopic enrichment of the isotopically enriched atom of the compound described herein is no less than the natural abundance of the isotope specified.

In certain embodiments, at least one of the atoms of the compound described herein, as specified as deuterium-enriched, has deuterium enrichment of no less than about 1%, no less than about 2%, no less than about 5%, no less than about 10%, no less than about 20%, no less than about 50%, no less than about 70%, no less than about 80%, no less than about 90%, or no less than about 98%. In certain embodiments, the atoms of the compound described herein, as specified as deuterium-enriched, have deuterium enrichment of no less than about 1%, no less than about 2%, no less than about 5%, no less than about 10%, no less than about 20%, no less than about 50%, no less than about 70%, no less than about 80%, no less than about 90%, or no less than about 98%.

In certain embodiments, at least one of the atoms of the compound described herein, as specified as $^{13}$C-enriched, has carbon-13 enrichment of no less than about 2%, no less than about 5%, no less than about 10%, no less than about 20%, no less than about 50%, no less than about 70%, no less than about 80%, no less than about 90%, or no less than about 98%. In certain embodiments, the atoms of the compound described herein, as specified as $^{13}$C-enriched, have carbon-13 enrichment of no less than about 1%, no less than about 2%, no less than about 5%, no less than about 10%, no less than about 20%, no less than about 50%, no less than about 70%, no less than about 80%, no less than about 90%, or no less than about 98%.

In certain embodiments, the compound described herein is isolated or purified. In certain embodiments, the compound described herein has a purity of at least about 50%, at least about 70%, at least about 80%, at least about 90%, at least about 95%, at least about 98%, at least about 99%, or at least about 99.5% by weight.

The compounds described herein are intended to encompass all possible stereoisomers, unless a particular stereochemistry is specified. Where the compound described herein contains an alkenyl or alkenylene group, the compound may exist as one or mixture of geometric cis/trans (or Z/E) isomers. Where structural isomers are interconvertible, the compound may exist as a single tautomer or a mixture of tautomers. This can take the form of proton tautomerism in the compound that contains, for example, an imino, keto, or oxime group; or so-called valence tautomerism in the compound that contain an aromatic moiety. It follows that a single compound may exhibit more than one type of isomerism.

The compounds described herein may be enantiomerically pure, such as a single enantiomer or a single diastereomer, or be stereoisomeric mixtures, such as a mixture of enantiomers, e.g., a racemic mixture of two enantiomers; or a mixture of two or more diastereomers. As such, one of ordinary skill in the art will recognize that administration of a compound in its (R) form is equivalent, for compounds that undergo epimerization in vivo, to administration of the compound in its (S) form. Conventional techniques for the preparation/isolation of individual enantiomers include synthesis from a suitable optically pure precursor, asymmetric synthesis from achiral starting materials, or resolution of an enantiomeric mixture, for example, chiral chromatography, recrystallization, resolution, diastereomeric salt formation, or derivatization into diastereomeric adducts followed by separation.

When the compound described herein contains an acidic or basic moiety, it may also be provided as a pharmaceutically acceptable salt (See, Berge et al., *J. Pharm. Sci.* 1977, 66, 1-19; and "Handbook of Pharmaceutical Salts, Properties, and Use," Stahl and Wermuth, Ed.; Wiley-VCH and VHCA, Zurich, 2002).

Suitable acids for use in the preparation of pharmaceutically acceptable salts include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxoglutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Suitable bases for use in the preparation of pharmaceutically acceptable salts, including, but not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methylglucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

The compound described herein may also be provided as a prodrug, which is a functional derivative of the compound, for example, of Formula I and is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis. See Harper, *Progress in Drug Research* 1962, 4, 221-294; Morozowich et al. in "Design of Biopharmaceutical Properties through Prodrugs and Analogs," *Roche Ed., APHA Acad. Pharm. Sci.* 1977; "Bioreversible Carriers in Drug in Drug Design, Theory and Application," Roche Ed., APHA Acad. Pharm. Sci. 1987; "Design of Prodrugs," Bundgaard, Elsevier, 1985; Wang et al., *Curr. Pharm. Design* 1999, 5, 265-287; Pauletti et al., *Adv. Drug. Delivery Rev.* 1997, 27, 235-256; Mizen et al., *Pharm. Biotech.* 1998, 11, 345-365; Gaignault et al., *Pract. Med. Chem.* 1996, 671-696; Asgharnejad in "Transport Processes in Pharmaceutical Systems," Amidon et al., Ed., Marcell Dekker, 185-218, 2000; Balant et al., *Eur. J. DrugMetab. Pharmacokinet.* 1990, 15, 143-53; Balimane and Sinko, *Adv. Drug Delivery Rev.* 1999, 39, 183-209; Browne, *Clin. Neuropharmacol.* 1997, 20, 1-12; Bundgaard, *Arch. Pharm. Chem.* 1979, 86, 1-39; Bundgaard, *Controlled Drug Delivery* 1987, 17, 179-96; Bundgaard, *Adv. Drug Delivery Rev.* 1992, 8, 1-38; Fleisher et al., *Adv. Drug Delivery Rev.* 1996, 19, 115-130; Fleisher et al., *Methods Enzymol.* 1985, 112, 360-381; Farquhar et al., *J. Pharm. Sci.* 1983, 72, 324-325; Freeman et al., *J. Chem. Soc., Chem. Commun.* 1991, 875-877; Friis and Bundgaard, *Eur. J. Pharm. Sci.* 1996, 4, 49-59; Gangwar et al., *Des. Biopharm. Prop. Prodrugs Analogs,* 1977, 409-421; Nathwani and Wood, *Drugs* 1993, 45, 866-94; Sinhababu and Thakker, *Adv. Drug Delivery Rev.* 1996, 19, 241-273; Stella et al., *Drugs* 1985, 29, 455-73; Tan et al., *Adv. Drug Delivery Rev.* 1999, 39, 117-151; Taylor, *Adv. Drug Delivery Rev.* 1996, 19, 131-148; Valentino and Borchardt, *Drug Discovery Today* 1997, 2, 148-155; Wiebe and Knaus, *Adv. Drug Delivery Rev.* 1999, 39, 63-80; and Waller et al., *Br. J. Clin. Pharmac.* 1989, 28, 497-507.

The compounds described herein can be prepared, isolated, or obtained by any method known to one of ordinary skill in the art. For an example, a compound of Formula I can be prepared according to the methods described in Luo et al., *Org. Lett.* 2011, 13, 2834-2836; and Lee, *Mar. Drugs* 2015, 13, 1581-1620; the disclosure of each of which is incorporated herein by reference in its entirety.

In certain embodiments, a compound of Formula I is synthesized according to Scheme I in the presence of a catalyst (e.g., a palladium catalyst such as $Pd(OAc)_2$), wherein X is a leaving group (e.g., iodo, bromo, or triflate), and $R^3$, $R^4$, $R^5$, and $R^6$ are each as defined herein.

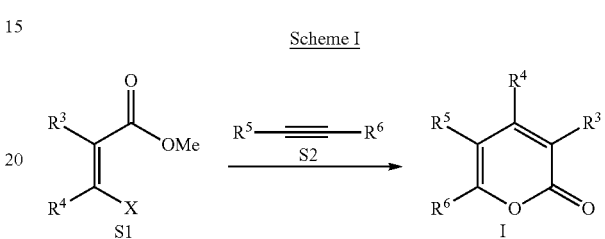

Scheme I

In certain embodiments, a compound of Formula I is synthesized according to Scheme II in the presence of a catalyst (e.g., a gold catalyst such as $Au(PPh3)Cl$), wherein $R^3$ is hydrogen, and $R^4$, $R^5$, and $R^6$ are each as defined herein.

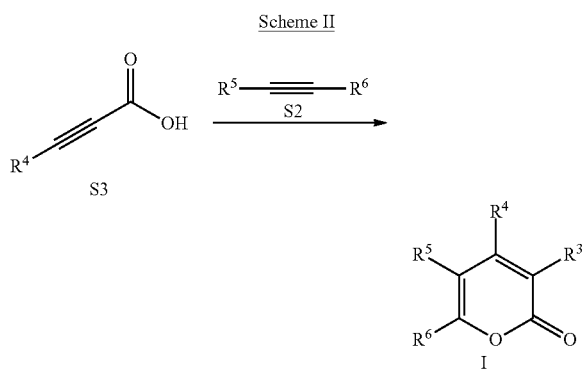

Scheme II

In one embodiment, an isotope is introduced into a compound described herein by synthetic techniques that employ suitable isotopically enriched reagents, whereby isotopic enrichment is pre-determined. In another embodiment, an isotope is introduced into a compound described herein by exchange techniques, wherein isotopic enrichment is determined by equilibrium conditions, which may be highly variable depending on the reaction conditions. In yet another embodiment, deuterium is introduced into a compound described herein by direct deuteration.

In one embodiment, to introduce deuterium at $R^3$ and/or $R^4$, compound S1 with the corresponding deuterium substitution is coupled with compound S2 to form a deuterated compound of Formula I. In another embodiment, to introduce deuterium at $R^5$ and/or $R^6$, compound S2 with the corresponding deuterium substitution is coupled with compound S1 to form a deuterated compound of Formula I. The deuterated starting materials and intermediates used herein are either commercially available, or can be prepared by methods known to one of ordinary skill in the art.

The compound described herein may be administered alone, or in combination with one or more other compounds described herein. The pharmaceutical compositions that comprise a compound described herein, e.g., a compound of Formula I, can be formulated in various dosage forms for oral, parenteral, and topical administration. The pharmaceutical compositions can also be formulated as modified release dosage forms, including delayed-, extended-, prolonged-, sustained-, pulsatile-, controlled-, accelerated-, fast-, targeted-, programmed-release, and gastric retention dosage forms. These dosage forms can be prepared according to conventional methods and techniques known to those skilled in the art (see, *Remington: The Science and Practice of Pharmacy*, supra; *Modified-Release Drug Delivery Technology, 2nd Edition*, Rathbone et al., Eds., Marcel Dekker, Inc.: New York, New York., 2008).

In one embodiment, the pharmaceutical compositions provided herein are formulated in a dosage form for oral administration, which comprise a compound described herein, e.g., a compound of Formula I, including an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, and one or more pharmaceutically acceptable excipients or carriers.

In another embodiment, the pharmaceutical compositions provided herein are formulated as a suspension for oral administration, which comprise a compound described herein, e.g., a compound of Formula I, including an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, and one or more pharmaceutically acceptable excipients or carriers. In one embodiment, the suspension provided herein comprises a compound described herein, e.g., a compound of Formula I, including an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; and one or more excipients or carriers selected from the group consisting of water, glycerin, sorbitol, sodium saccharin, xanthan gum, flavoring, citric acid, sodium citrate, methylparaben, propylparaben, and potassium sorbate. In another embodiment, the suspension provided herein comprises a compound described herein, e.g., a compound of Formula I, including an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; and water, glycerin, sorbitol, sodium saccharin, xanthan gum, flavoring, citric acid, sodium citrate, methylparaben, propylparaben, and potassium sorbate.

In yet another embodiment, the pharmaceutical compositions provided herein are formulated in a dosage form for parenteral administration, which comprise a compound described herein, e.g., a compound of Formula I, including an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; and one or more pharmaceutically acceptable excipients or carriers. In one embodiment, the pharmaceutical compositions provided herein are formulated in a dosage form for intravenous administration. In another embodiment, the pharmaceutical compositions provided herein are formulated in a dosage form for intramuscular administration. In yet another embodiment, the pharmaceutical compositions provided herein are formulated in a dosage form for subcutaneous administration.

In yet another embodiment, the pharmaceutical compositions provided herein are formulated in a dosage form for topical administration, which comprise a compound described herein, e.g., a compound of Formula I, including an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, and one or more pharmaceutically acceptable excipients or carriers.

In one embodiment, the pharmaceutical compositions provided herein are formulated as a cream for topical administration, which comprise a compound described herein, e.g., a compound of Formula I, including an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof, and one or more pharmaceutically acceptable excipients or carriers. In one embodiment, the cream provided herein comprises a compound described herein, e.g., a compound of Formula I, including an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof; and one or more excipients or carriers selected from the group consisting of water, octyldodecanol, mineral oil, stearyl alcohol, cocamide DEA, polysorbate 60, myristyl alcohol, sorbitan monostearate, lactic acid, and benzyl alcohol. In another embodiment, the cream provided herein comprises a compound described herein, e.g., a compound of Formula I, including an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; and water, octyldodecanol, mineral oil, stearyl alcohol, cocamide DEA, polysorbate 60, myristyl alcohol, sorbitan monostearate, lactic acid, and benzyl alcohol.

In another embodiment, the pharmaceutical compositions provided herein are formulated as a gel for topical administration, which comprise a compound described herein, e.g., a compound of Formula I, including an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof, and one or more pharmaceutically acceptable excipients or carriers. In one embodiment, the gel provided herein comprises a compound described herein, e.g., a compound of Formula I, including an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof; and one or more excipients or carriers selected from the group consisting of water, isopropyl alcohol, octyldodecanol, dimethicone copolyol 190, carbomer 980, sodium hydroxide, and docusate sodium. In another embodiment, the gel provided herein comprises a compound described herein, e.g., a compound of Formula I, including an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, and water, isopropyl alcohol, octyldodecanol, dimethicone copolyol 190, carbomer 980, sodium hydroxide, and docusate sodium.

In yet another embodiment, the pharmaceutical compositions provided herein are formulated as a shampoo for topical administration, which comprise a compound described herein, e.g., a compound of Formula I, including an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, and one or more pharmaceutically acceptable excipients or carriers. In one embodiment, the shampoo provided herein comprises a compound described herein, e.g., a compound of Formula I, including an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; and one or more excipients or carriers selected from the group consisting of water, sodium laureth sulfate, disodium laureth sulfosuccinate, sodium chloride, and laureth-2. In another embodiment, the shampoo provided herein comprises a compound described herein, e.g., a compound of Formula I, including an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof; and water, sodium laureth sulfate, disodium laureth sulfosuccinate, sodium chloride, and laureth-2.

In still another embodiment, the pharmaceutical compositions provided herein are formulated as a lacquer for topical administration, which comprise a compound described herein, e.g., a compound of Formula I, including an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, and one or more pharmaceutically acceptable excipients or carriers. In one embodiment, the lacquer provided herein comprises a compound described herein, e.g., a compound of Formula I, including an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof; and one or more excipients or carriers selected from the group consisting of ethyl acetate, isopropyl alcohol, and butyl monoester of poly(methylvinyl ether/maleic acid) in isopropyl alcohol. In another embodiment, the lacquer provided herein comprises a compound described herein, e.g., a compound of Formula I, including an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; and ethyl acetate, isopropyl alcohol, and butyl monoester of poly(methylvinyl ether/maleic acid) in isopropyl alcohol.

The pharmaceutical compositions provided herein can be provided in a unit-dosage form or multiple-dosage form. A unit-dosage form, as used herein, refers to physically discrete a unit suitable for administration to a human and animal subject, and packaged individually as is known in the art. Each unit-dose contains a predetermined quantity of an active ingredient(s) sufficient to produce the desired therapeutic effect, in association with the required pharmaceutical carriers or excipients. Examples of a unit-dosage form include an ampoule, syringe, and individually packaged tablet and capsule. A unit-dosage form may be administered in fractions or multiples thereof. A multiple-dosage form is a plurality of identical unit-dosage forms packaged in a single container to be administered in segregated unit-dosage form. Examples of a multiple-dosage form include a vial, bottle of tablets or capsules, or bottle of pints or gallons.

The pharmaceutical compositions provided herein can be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

A. Oral Administration

The pharmaceutical compositions provided herein for oral administration can be provided in solid, semisolid, or liquid dosage forms for oral administration. As used herein, oral administration also includes buccal, lingual, and sublingual administration. Suitable oral dosage forms include, but are not limited to, tablets, fastmelts, chewable tablets, capsules, pills, strips, troches, lozenges, pastilles, cachets, pellets, medicated chewing gum, bulk powders, effervescent or non-effervescent powders or granules, oral mists, solutions, emulsions, suspensions, wafers, sprinkles, elixirs, and syrups. In addition to the active ingredient(s), the pharmaceutical compositions can contain one or more pharmaceutically acceptable carriers or excipients, including, but not limited to, binders, fillers, diluents, disintegrants, wetting agents, lubricants, glidants, coloring agents, dye-migration inhibitors, sweetening agents, flavoring agents, emulsifying agents, suspending and dispersing agents, preservatives, solvents, non-aqueous liquids, organic acids, and sources of carbon dioxide.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, PA); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The amount of a binder or filler in the pharmaceutical compositions provided herein varies upon the type of formulation, and is readily discernible to those of ordinary skill in the art. The binder or filler may be present from about 50 to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets. The amount of a diluent in the pharmaceutical compositions provided herein varies upon the type of formulation, and is readily discernible to those of ordinary skill in the art.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of a disintegrant in the pharmaceutical compositions provided herein varies upon the type of formulation, and is readily discernible to those of ordinary skill in the art. The amount of a disintegrant in the pharmaceutical compositions provided herein varies upon the type of formulation, and is readily discernible to those of ordinary skill in the art. The pharmaceutical compositions provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W. R. Grace Co., Baltimore, MD) and CAB-O-SIL® (Cabot Co. of Boston, MA); and mixtures thereof. The pharmaceutical compositions provided herein may contain about 0.1 to about 5% by weight of a lubricant.

Suitable glidants include, but are not limited to, colloidal silicon dioxide, CAB-O-SIL® (Cabot Co. of Boston, MA), and asbestos-free talc. Suitable coloring agents include, but are not limited to, any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Suitable flavoring agents include, but are not limited to, natural flavors extracted from plants, such as fruits, and synthetic blends of compounds which produce a pleasant taste sensation, such as peppermint and methyl salicylate. Suitable sweetening agents include, but are not limited to, sucrose, lactose, mannitol, syrups, glycerin, and artificial sweeteners, such as saccharin and aspartame. Suitable emulsifying agents include, but are not limited to, gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suitable suspending and dispersing agents include, but are not limited to, sodium carboxymethylcellulose, pectin, tragacanth, Veegum, acacia, sodium carbomethylcellulose, hydroxypropyl methylcellulose, and polyvinylpyrrolidone.

Suitable preservatives include, but are not limited to, glycerin, methyl and propylparaben, benzoic add, sodium benzoate and alcohol. Suitable wetting agents include, but are not limited to, propylene glycol monostearate, sorbitan monooleate, diethylene glycol monolaurate, and polyoxyethylene lauryl ether. Suitable solvents include, but are not limited to, glycerin, sorbitol, ethyl alcohol, and syrup. Suitable non-aqueous liquids utilized in emulsions include, but are not limited to, mineral oil and cottonseed oil. Suitable organic acids include, but are not limited to, citric and tartaric acid. Suitable sources of carbon dioxide include, but are not limited to, sodium bicarbonate and sodium carbonate.

It should be understood that many carriers and excipients may serve several functions, even within the same formulation.

The pharmaceutical compositions provided herein for oral administration can be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms can be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein for oral administration can be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

The pharmaceutical compositions provided herein for oral administration can be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquid or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations can further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical compositions provided herein for oral administration can be also provided in the forms of liposomes, micelles, microspheres, or nanosystems. Micellar dosage forms can be prepared as described in U.S. Pat. No. 6,350,458.

The pharmaceutical compositions provided herein for oral administration can be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The pharmaceutical compositions provided herein for oral administration can be formulated as immediate or modified release dosage forms, including delayed-, sustained, pulsed-, controlled, targeted-, and programmed-release forms.

B. Parenteral Administration

The pharmaceutical compositions provided herein can be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, intravesical, and subcutaneous administration.

The pharmaceutical compositions provided herein for parenteral administration can be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, *Remington: The Science and Practice of Pharmacy*, supra).

The pharmaceutical compositions intended for parenteral administration can include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Suitable non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Suitable water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcelluose, hydroxypropyl methylcellulose, and polyvinylpyrrolidone. Suitable emulsifying agents are those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, KS).

When the pharmaceutical compositions provided herein are formulated for multiple dosage administration, the multiple dosage parenteral formulations must contain an antimicrobial agent at bacteriostatic or fungistatic concentrations. All parenteral formulations must be sterile, as known and practiced in the art.

In one embodiment, the pharmaceutical compositions for parenteral administration are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions provided herein for parenteral administration can be formulated as immediate or modified release dosage forms, including delayed-, sustained, pulsed-, controlled, targeted-, and programmed-release forms.

The pharmaceutical compositions provided herein for parenteral administration can be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include, but are not limited to, polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

Suitable outer polymeric membranes include but are not limited to, polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

C. Topical Administration

The pharmaceutical compositions provided herein can be administered topically to the skin, orifices, or mucosa. The topical administration, as used herein, includes (intra)dermal, conjunctival, intracorneal, intraocular, ophthalmic, auricular, transdermal, nasal, vaginal, urethral, respiratory, and rectal administration.

The pharmaceutical compositions provided herein can be formulated in any dosage forms that are suitable for topical administration for local or systemic effect, including emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, and dermal patches. The topical formulation of the pharmaceutical compositions provided herein can also comprise liposomes, micelles, microspheres, nanosystems, and mixtures thereof.

Pharmaceutically acceptable carriers and excipients suitable for use in the topical formulations provided herein include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryoprotectants, lyoprotectants, thickening agents, and inert gases.

The pharmaceutical compositions can also be administered topically by electroporation, iontophoresis, phonophoresis, sonophoresis, or microneedle or needle-free injection, such as POWDERJECT™ (Chiron Corp., Emeryville, CA), and BIOJECT™ (Bioject Medical Technologies Inc., Tualatin, OR).

The pharmaceutical compositions provided herein can be provided in the forms of ointments, creams, and gels. Suitable ointment vehicles include oleaginous or hydrocarbon vehicles, including lard, benzoinated lard, olive oil, cottonseed oil, and other oils, white petrolatum; emulsifiable or absorption vehicles, such as hydrophilic petrolatum, hydroxystearin sulfate, and anhydrous lanolin; water-removable vehicles, such as hydrophilic ointment; water-soluble ointment vehicles, including polyethylene glycols of varying molecular weight; emulsion vehicles, either water-in-oil (W/O) emulsions or oil-in-water (O/W) emulsions, including cetyl alcohol, glyceryl monostearate, lanolin, and stearic acid (see, Remington: The Science and Practice of Pharmacy, supra). These vehicles are emollient but generally require addition of antioxidants and preservatives.

Suitable cream base can be oil-in-water or water-in-oil. Suitable cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation may be a nonionic, anionic, cationic, or amphoteric surfactant.

Gels are semisolid, suspension-type systems. Single-phase gels contain organic macromolecules distributed substantially uniformly throughout the liquid carrier. Suitable gelling agents include, but are not limited to, crosslinked acrylic acid polymers, such as carbomers, carboxypolyalkylenes, and CARBOPOL®; hydrophilic polymers, such as polyethylene oxides, polyoxyethylene-polyoxypropylene copolymers, and polyvinylalcohol; cellulosic polymers, such as hydroxypropyl cellulose, hydroxyethyl cellulose, hydroxypropyl methylcellulose, hydroxypropyl methylcellulose phthalate, and methylcellulose; gums, such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

The pharmaceutical compositions provided herein can be administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes as described in Remington: The Science and Practice of Pharmacy, supra.

Rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include bases or vehicles, such as stiffening agents, which produce a melting point in the proximity of body temperature, when formulated with the pharmaceutical compositions provided herein; and antioxidants as described herein, including bisulfite and sodium metabisulfite. Suitable vehicles include, but are not limited to, cocoa butter (*theobroma* oil), glycerin-gelatin, carbowax (polyoxyethylene glycol), spermaceti, paraffin, white and yellow wax, and appropriate mixtures of mono-, di- and triglycerides of fatty acids, and hydrogels, such as polyvinyl alcohol, hydroxyethyl methacrylate, and polyacrylic acid. Combinations of the various vehicles can also be used. Rectal and vaginal suppositories may be prepared by compressing or molding. The typical weight of a rectal and vaginal suppository is about 2 to about 3 g.

The pharmaceutical compositions provided herein can be administered ophthalmically in the forms of solutions, suspensions, ointments, emulsions, gel-forming solutions, powders for solutions, gels, ocular inserts, and implants.

The pharmaceutical compositions provided herein can be administered intranasally or by inhalation to the respiratory tract. The pharmaceutical compositions can be provided in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical compositions can also be provided as a dry powder for insufflation, alone or in combination with an inert carrier such as lactose or phospholipids; and nasal drops. For intranasal use, the powder can comprise a bioadhesive agent, including chitosan or cyclodextrin.

Solutions or suspensions for use in a pressurized container, pump, spray, atomizer, or nebulizer can be formulated to contain ethanol, aqueous ethanol, or a suitable alternative agent for dispersing, solubilizing, or extending release of the active ingredient provided herein; a propellant as solvent; and/or a surfactant, such as sorbitan trioleate, oleic acid, or an oligolactic acid.

The pharmaceutical compositions provided herein can be micronized to a size suitable for delivery by inhalation, such as about 50 micrometers or less, or about 10 micrometers or less. Particles of such sizes can be prepared using a comminuting method known to those skilled in the art, such as spiral jet milling, fluid bed jet milling, supercritical fluid processing to form nanoparticles, high pressure homogenization, or spray drying.

Capsules, blisters, and cartridges for use in an inhaler or insufflator can be formulated to contain a powder mix of the pharmaceutical compositions provided herein; a suitable powder base, such as lactose or starch; and a performance modifier, such as l-leucine, mannitol, or magnesium stearate. The lactose may be anhydrous or in the form of the monohydrate. Other suitable excipients or carriers include, but are not limited to, dextran, glucose, maltose, sorbitol, xylitol, fructose, sucrose, and trehalose. The pharmaceutical compositions provided herein for inhaled/intranasal administration can further comprise a suitable flavor, such as menthol and levomenthol; and/or sweeteners, such as saccharin and saccharin sodium.

The pharmaceutical compositions provided herein for topical administration can be formulated to be immediate release or modified release, including delayed-, sustained-, pulsed-, controlled-, targeted, and programmed release.

D. Modified Release

The pharmaceutical compositions provided herein can be formulated as a modified release dosage form. As used herein, the term "modified release" refers to a dosage form in which the rate or place of release of the active ingredient(s) is different from that of an immediate dosage form when administered by the same route. Modified release dosage forms include, but are not limited to, delayed-, extended-, prolonged-, sustained-, pulsatile-, controlled-, accelerated- and fast-, targeted-, programmed-release, and gastric retention dosage forms. The pharmaceutical compositions in modified release dosage forms can be prepared using a variety of modified release devices and methods known to those skilled in the art, including, but not limited to, matrix controlled release devices, osmotic controlled release devices, multiparticulate controlled release devices, ion-exchange resins, enteric coatings, multilayered coatings, microspheres, liposomes, and combinations thereof. The release rate of the active ingredient(s) can also be modified by varying the particle sizes and polymorphorism of the active ingredient(s).

Examples of modified release include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; and 6,699,500.

1. Matrix Controlled Release Devices

The pharmaceutical compositions provided herein in a modified release dosage form can be fabricated using a matrix controlled release device known to those skilled in the art (see, Takada et al. in "*Encyclopedia of Controlled Drug Delivery*," Vol. 2, Mathiowitz Ed., Wiley, 1999).

In certain embodiments, the pharmaceutical compositions provided herein in a modified release dosage form is formulated using an erodible matrix device, which is water-swellable, erodible, or soluble polymers, including, but not limited to, synthetic polymers, and naturally occurring polymers and derivatives, such as polysaccharides and proteins.

Materials useful in forming an erodible matrix include, but are not limited to, chitin, chitosan, dextran, and pullulan; gum agar, gum arabic, gum karaya, locust bean gum, gum tragacanth, carrageenans, gum ghatti, guar gum, xanthan gum, and scleroglucan; starches, such as dextrin and maltodextrin; hydrophilic colloids, such as pectin; phosphatides, such as lecithin; alginates; propylene glycol alginate; gelatin; collagen; cellulosics, such as ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethyl hydroxyethyl cellulose (EHEC); polyvinyl pyrrolidone; polyvinyl alcohol; polyvinyl acetate; glycerol fatty acid esters; polyacrylamide; polyacrylic acid; copolymers of ethacrylic acid or methacrylic acid (EUDRAGIT®, Rohm America, Inc., Piscataway, NJ); poly(2-hydroxyethyl-methacrylate); polylactides; copolymers of L-glutamic acid and ethyl-L-glutamate; degradable lactic acid-glycolic acid copolymers; poly-D-(-)-3-hydroxybutyric acid; and other acrylic acid derivatives, such as homopolymers and copolymers of butylmethacrylate, methyl methacrylate, ethyl methacrylate, ethylacrylate, (2-dimethylaminoethyl)methacrylate, and (trimethylaminoethyl)methacrylate chloride.

In certain embodiments, the pharmaceutical compositions provided herein are formulated with a non-erodible matrix device. The active ingredient(s) is dissolved or dispersed in an inert matrix and is released primarily by diffusion through the inert matrix once administered. Materials suitable for use as a non-erodible matrix device include, but are not limited to, insoluble plastics, such as polyethylene, polypropylene, polyisoprene, polyisobutylene, polybutadiene, polymethylmethacrylate, polybutylmethacrylate, chlorinated polyethylene, polyvinylchloride, methyl acrylate-methyl methacrylate copolymers, ethylene-vinyl acetate copolymers, ethylene/propylene copolymers, ethylene/ethyl acrylate copolymers, vinyl chloride copolymers with vinyl acetate, vinylidene chloride, ethylene and propylene, ionomer polyethylene terephthalate, butyl rubbers, epichlorohydrin rubbers, ethylene/vinyl alcohol copolymer, ethylene/vinyl acetate/vinyl alcohol terpolymer, ethylene/vinyloxyethanol copolymer, polyvinyl chloride, plasticized nylon, plasticized polyethylene terephthalate, natural rubber, silicone rubbers, polydimethylsiloxanes, and silicone carbonate copolymers; hydrophilic polymers, such as ethyl cellulose, cellulose acetate, crospovidone, and cross-linked partially hydrolyzed polyvinyl acetate; and fatty compounds, such as carnauba wax, microcrystalline wax, and triglycerides.

In a matrix controlled release system, the desired release kinetics can be controlled, for example, via the polymer type employed, the polymer viscosity, the particle sizes of the polymer and/or the active ingredient(s), the ratio of the active ingredient(s) versus the polymer, and other excipients or carriers in the compositions.

The pharmaceutical compositions provided herein in a modified release dosage form can be prepared by methods known to those skilled in the art, including direct compression, dry or wet granulation followed by compression, and melt-granulation followed by compression.

2. Osmotic Controlled Release Devices

The pharmaceutical compositions provided herein in a modified release dosage form can be fabricated using an osmotic controlled release device, including, but not limited to, one-chamber system, two-chamber system, asymmetric membrane technology (AMT), and extruding core system (ECS). In general, such devices have at least two components: (a) a core which contains an active ingredient; and (b) a semipermeable membrane with at least one delivery port, which encapsulates the core. The semipermeable membrane controls the influx of water to the core from an aqueous environment of use so as to cause drug release by extrusion through the delivery port(s).

In addition to the active ingredient(s), the core of the osmotic device optionally includes an osmotic agent, which creates a driving force for transport of water from the environment of use into the core of the device. One class of osmotic agents is water-swellable hydrophilic polymers, which are also referred to as "osmopolymers" and "hydrogels." Suitable water-swellable hydrophilic polymers as osmotic agents include, but are not limited to, hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly(acrylic) acid, poly(methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

The other class of osmotic agents is osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphates, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol; organic acids, such as ascorbic acid, benzoic acid, fumaric acid, citric acid, maleic acid, sebacic acid, sorbic acid, adipic acid, edetic acid, glutamic acid, p-toluenesulfonic acid, succinic acid, and tartaric acid; urea; and mixtures thereof.

Osmotic agents of different dissolution rates can be employed to influence how rapidly the active ingredient(s) is initially delivered from the dosage form. For example, amorphous sugars, such as MANNOGEM™ EZ (SPI Pharma, Lewes, DE) can be used to provide faster delivery during the first couple of hours to promptly produce the desired therapeutic effect, and gradually and continually release of the remaining amount to maintain the desired level of therapeutic or prophylactic effect over an extended period of time. In this case, the active ingredient(s) is released at such a rate to replace the amount of the active ingredient metabolized and excreted.

The core can also include a wide variety of other excipients and carriers as described herein to enhance the performance of the dosage form or to promote stability or processing.

Materials useful in forming the semipermeable membrane include various grades of acrylics, vinyls, ethers, polyamides, polyesters, and cellulosic derivatives that are water-permeable and water-insoluble at physiologically relevant pHs, or are susceptible to being rendered water-insoluble by chemical alteration, such as crosslinking. Examples of suitable polymers useful in forming the coating, include plasticized, unplasticized, and reinforced cellulose acetate (CA), cellulose diacetate, cellulose triacetate, CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxylated ethylene-vinylacetate, EC, PEG, PPG, PEG/PPG copolymers, PVP, HEC, HPC, CMC, CMEC, HPMC, HPMCP, HPMCAS, HPMCAT, poly(acrylic) acids and esters and poly-(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes, and synthetic waxes.

Semipermeable membrane can also be a hydrophobic microporous membrane, wherein the pores are substantially filled with a gas and are not wetted by the aqueous medium but are permeable to water vapor, as disclosed in U.S. Pat. No. 5,798,119. Such hydrophobic but water-vapor permeable membrane are typically composed of hydrophobic polymers such as polyalkenes, polyethylene, polypropylene, polytetrafluoroethylene, polyacrylic acid derivatives, polyethers, polysulfones, polyethersulfones, polystyrenes, polyvinyl halides, polyvinylidene fluoride, polyvinyl esters and ethers, natural waxes, and synthetic waxes.

The delivery port(s) on the semipermeable membrane can be formed post-coating by mechanical or laser drilling. Delivery port(s) can also be formed in situ by erosion of a plug of water-soluble material or by rupture of a thinner portion of the membrane over an indentation in the core. In addition, delivery ports can be formed during coating process, as in the case of asymmetric membrane coatings of the type disclosed in U.S. Pat. Nos. 5,612,059 and 5,698,220.

The total amount of the active ingredient(s) released and the release rate can substantially by modulated via the thickness and porosity of the semipermeable membrane, the composition of the core, and the number, size, and position of the delivery ports.

The pharmaceutical compositions in an osmotic controlled-release dosage form can further comprise additional conventional excipients or carriers as described herein to promote performance or processing of the formulation.

The osmotic controlled-release dosage forms can be prepared according to conventional methods and techniques known to those skilled in the art (see, Remington: The Science andPractice ofPharmacy, supra; Santus and Baker, *J. Controlled Release* 1995, 35, 1-21; Verma et al., *Drug Development and Industrial Pharmacy* 2000, 26, 695-708; Verma et al., *J. Controlled Release* 2002, 79, 7-27).

In certain embodiments, the pharmaceutical compositions provided herein are formulated as AMT controlled-release dosage form, which comprises an asymmetric osmotic membrane that coats a core comprising the active ingredient(s) and other pharmaceutically acceptable excipients or carriers. See, U.S. Pat. No. 5,612,059 and WO 2002/17918. The AMT controlled-release dosage forms can be prepared according to conventional methods and techniques known to those skilled in the art, including direct compression, dry granulation, wet granulation, and a dip-coating method.

In certain embodiments, the pharmaceutical compositions provided herein are formulated as ESC controlled-release dosage form, which comprises an osmotic membrane that coats a core comprising the active ingredient(s), a hydroxylethyl cellulose, and other pharmaceutically acceptable excipients or carriers.

3. Multiparticulate Controlled Release Devices

The pharmaceutical compositions provided herein in a modified release dosage form can be fabricated as a multiparticulate controlled release device, which comprises a multiplicity of particles, granules, or pellets, ranging from about 10 μm to about 3 mm, about 50 μm to about 2.5 mm, or from about 100 μm to about 1 mm in diameter. Such multiparticulates can be made by the processes known to those skilled in the art, including wet- and dry-granulation, extrusion/spheronization, roller-compaction, melt-congealing, and by spray-coating seed cores. See, for example, *Multiparticulate Oral Drug Delivery*; Marcel Dekker: 1994; and *Pharmaceutical Pelletization Technology*; Marcel Dekker: 1989.

Other excipients or carriers as described herein can be blended with the pharmaceutical compositions to aid in processing and forming the multiparticulates. The resulting particles can themselves constitute the multiparticulate device or can be coated by various film-forming materials, such as enteric polymers, water-swellable, and water-soluble polymers. The multiparticulates can be further processed as a capsule or a tablet.

4. Targeted Delivery

The pharmaceutical compositions provided herein can also be formulated to be targeted to a particular tissue, receptor, or other area of the body of the subject to be treated, including liposome-, resealed erythrocyte-, and antibody-based delivery systems. Examples include, but are not limited to, those disclosed in U.S. Pat. Nos. 6,316,652; 6,274,552; 6,271,359; 6,253,872; 6,139,865; 6,131,570; 6,120,751; 6,071,495; 6,060,082; 6,048,736; 6,039,975; 6,004,534; 5,985,307; 5,972,366; 5,900,252; 5,840,674; 5,759,542; and 5,709,874.

Methods of Use

In one embodiment, provided herein is a method for treating one or more symptoms of an inflammatory, neurodegenerative, or immune-mediated disease, in one embodiment, multiple sclerosis, in a subject, which comprises administering to the subject a therapeutically effective amount of a compound described herein, e.g., a compound of Formula I, including an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof.

In another embodiment, provided herein is a method for treating an inflammatory disease in a subject, which comprises administering to the subject a therapeutically effective amount of a compound described herein, e.g., a compound of Formula I, including an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof.

In yet another embodiment, provided herein is a method for treating a neurodegenerative disease in a subject, which comprises administering to the subject a therapeutically effective amount of a compound described herein, e.g., a compound of Formula I, including an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof.

In still another embodiment, provided herein is a method for treating an immune-mediated disease in a subject, which comprises administering to the subject a therapeutically effective amount of a compound described herein, e.g., a compound of Formula I, including an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof.

In certain embodiments, the therapeutically effective amount is ranging from about 0.1 to about 100 mg/kg/day, from about 0.1 to about 50 mg/kg/day, from about 0.1 to about 40 mg/kg/day, from about 0.1 to about 30 mg/kg/day, from about 0.1 to about 25 mg/kg/day, from about 0.1 to about 20 mg/kg/day, from about 0.1 to about 15 mg/kg/day, from about 0.1 to about 10 mg/kg/day, or from about 0.1 to about 5 mg/kg/day. In one embodiment, the therapeutically effective amount is ranging from about 0.1 to about 100 mg/kg/day. In another embodiment, the therapeutically effective amount is ranging from about 0.1 to about 50 mg/kg/day. In yet another embodiment, the therapeutically effective amount is ranging from about 0.1 to about 40 mg/kg/day. In yet another embodiment, the therapeutically effective amount is ranging from about 0.1 to about 30 mg/kg/day. In yet another embodiment, the therapeutically effective amount is ranging from about 0.1 to about 25 mg/kg/day. In yet another embodiment, the therapeutically effective amount is ranging from about 0.1 to about 20 mg/kg/day. In yet another embodiment, the therapeutically effective amount is ranging from about 0.1 to about 15 mg/kg/day. In yet another embodiment, the therapeutically effective amount is ranging from about 0.1 to about 10 mg/kg/day. In still another embodiment, the therapeutically effective amount is ranging from about 0.1 to about 5 mg/kg/day.

It is understood that the administered dose can also be expressed in units other than mg/kg/day. For example, doses for parenteral administration can be expressed as $mg/m^2/day$. One of ordinary skill in the art would readily know how to convert doses from mg/kg/day to $mg/m^2$/day to given either the height or weight of a subject or both. For example, a dose of 1 $mg/m^2$/day for a 65 kg human is approximately equal to 38 mg/kg/day.

In certain embodiments, the subject is a mammal. In certain embodiments, the subject is a human.

In certain embodiments, the diseases that are treatable with the methods provided herein include, but are not limited to, chronic active hepatitis (CAH), primary biliary cirrhosis (PBC), primary sclerosing cholangitis (PSC), celiac disease, pernicious anemia, and inflammatory bowel disease.

In certain embodiments, the diseases that are treatable with the methods provided herein include, but are not limited to, chronic inflammatory demyelinating polyradiculoneuropathy (CIDP), acute inflammatory demyelinating polyneuropathy (AIDP), Lambert-Eaton myasthenic syndrome (LEMS), myasthenia gravis, meuromyotonia (Isaacs' syndrome), stiff man syndrome or Moersch-Woltmann syndrome, multiple sclerosis (MS), Gullain-Barre syndrome, multifocal motor neuropathy with conduction block (MMN), monoclonal gammopathy, paraneoplastic neurological disorders (PND's), Oppsoclonus-myoclonus syndrome (OMS), encephalomyelitis, and autoimmune retinopathy (AR) (recoverin-associated retinopathy(RAR)).

In certain embodiments, the diseases that are treatable with the methods provided herein include, but are not limited to, systemic necrotizing vascolitides, polyarteritis nodosa (PAN), polymyalgia rheumatic, Churg-Strauss syndrome (CSS), allergic granulomatosis angiitis, hypersensitivity vasculitis, Wegener's, granulomatosis, temporal arteritis, giant cell arteritis (GCV), Takayasu's arteritis (TAK), Kawasaki disease (KD), isolated vasculitis of the central nervous system, CNS vasculitis, thromboangiitis obliterans, Buerger's disease, sarcoidosis, graft-versus-host disease (GVHD), cryoglobulinemia, and cryopathies.

In certain embodiments, the diseases that are treatable with the methods provided herein include, but are not limited to, Meniere's disease, Raynaud's phenomenon, antiphospholipid syndrome (APS), autoimmune lymphoproliferative syndrome (ALPS), autoimmune inner ear disease (AIED), and Cogan's syndrome.

In certain embodiments, the diseases that are treatable with the methods provided herein include, but are not limited to, alopecia areata, autoimmune hemolytic anemia, autoimmune hepatitis, dermatomyositis, diabetes (type 1), certain juvenile idiopathic arthritis, glomerulonephritis, Graves' disease, Guilain-Barre syndrome, idiopathic thrombocytopenic purpura, myasthenia gravis, certain myocarditis, multiple sclerosis, pemphigus/pemphigoid, pernicious anemia, polyarteritis nodosa, polymyositis, primary biliary cirrhosis, psoriatic arthritis, psoriasis, rheumatoid arthritis, schleroderma/systemic sclerosis, Sjogren's syndrome, systemic lupus erythematosus, certain thyroiditis, certain uveitis, vitiligo, and granulomatosis with polyangiitis (Wegener's).

In certain embodiments, the inflammatory, neurodegenerative, or immune-mediated disease is an inflammatory disease. In certain embodiments, the inflammatory, neurodegenerative, or immune-mediated disease is a neurodegenerative disease. In certain embodiments, the inflammatory, neurodegenerative, or immune-mediated disease is an immune-mediated disease.

In certain embodiments, the immune-mediated disease is an inflammatory disease or disorder related to immune dysfunction, immunodeficiency, or immunomodulation, including, but not limited to, autoimmune diseases, tissue transplant rejection, graft-versus-host disease, wound healing, kidney disease, multiple sclerosis, thyroiditis, type 1 diabetes, sarcoidosis, allergic rhinitis, inflammatory bowel diseases (including Crohn's disease and ulcerative colitis (UC)), systemic lupus erythematosus (SLE), arthritis, osteoarthritis, rheumatoid arthritis, osteoporosis, asthma, and chronic obstructive pulmonary disease (COPD).

In certain embodiments, the immune-mediated disease is an autoimmune disease. In certain embodiments, the autoimmune is a B cell-mediated autoimmune disease. In certain embodiments, the autoimmune disease is an antibody-mediated autoimmune disease. In certain embodiments, the autoimmune disease is a T-cell mediated autoimmune disease.

In certain embodiments, the autoimmune disease is alopecia areata, autoimmune hemolytic anemia, autoimmune hepatitis, dermatomyositis, diabetes (type 1), certain juvenile idiopathic arthritis, glomerulonephritis, Graves' disease, Guilain-Barre syndrome, idiopathic thrombocytopenic purpura, myasthenia gravis, certain myocarditis, multiple sclerosis, pemphigus/pemphigoid, pernicious anemia, polyarteritis nodosa, polymyositis, primary biliary cirrhosis, psoriatic arthritis, psoriasis, rheumatoid arthritis, schleroderma/systemic sclerosis, Sjogren's syndrome, systemic lupus erythematosus, certain thyroiditis, certain uveitis, vitiligo, or granulomatosis with polyangiitis (Wegener's).

In certain embodiments, the autoimmune disease is multiple sclerosis (MS). In certain embodiments, the autoimmune disease is relapsing-remitting MS (RR-MS). In certain embodiments, the autoimmune disease is primary progressive MS (PP-MS). In certain embodiments, the autoimmune disease is progressive relapsing MS (PR-MS). In certain embodiments, the autoimmune disease is secondary progressive MS (SP-MS).

The methods provided herein encompass treating a subject regardless of patient's age, although some diseases or disorders are more common in certain age groups.

Depending on the disease to be treated and the subject's condition, a compound described herein, e.g., a compound of Formula I, including an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, may be administered by oral, parenteral (e.g., intramuscular, intraperitoneal, intravenous, CIV, intracistemal injection or infusion, subcutaneous injection, or implant), inhalation, nasal, vaginal, rectal, sublingual, or topical (e.g., transdermal or local) routes of administration. A compound described herein, e.g., an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, may be formulated, alone or together, in suitable dosage unit with pharmaceutically acceptable excipients, carriers, adjuvants and vehicles, appropriate for each route of administration.

In one embodiment, a compound described herein, e.g., a compound of Formula I, including an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof, is administered orally. In another embodiment, a compound described herein, e.g., a compound of Formula I, including an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof, is administered parenterally. In yet another embodiment, a compound described herein, e.g., a compound of Formula I, including an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof, is administered intravenously. In yet another embodiment, a compound described herein, e.g., a compound of Formula I, including an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof, is administered intramuscularly. In yet another embodiment, a compound described herein, e.g., a compound of Formula I, including an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof, is administered subcutaneously. In still another embodiment, a compound described herein, e.g., a compound of Formula I, including an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, is administered topically.

A compound described herein, e.g., a compound of Formula I, including an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof, can be delivered as a single dose such as, e.g., a single bolus injection, or oral tablets or pills; or over time such as, e.g., continuous infusion over time or divided bolus doses over time. The compound described herein can be administered repetitively if necessary, for example, until the patient experiences stable disease or regression, or until the patient experiences disease progression or unacceptable toxicity. Stable disease or lack thereof is determined by methods known in the art such as evaluation of patient symptoms, physical examination, visualization of the tumor that has been imaged using X-ray, CAT, PET, or MRI scan and other commonly accepted evaluation modalities.

A compound described herein, e.g., a compound of Formula I, including an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof, can be administered once daily (QD), or divided into multiple daily doses such as twice daily (BID), and three times daily (TID). In addition, the administration can be continuous, i.e., every day, or intermittently. The term "intermittent" or "intermittently" as used herein is intended to mean stopping and starting at either regular or irregular intervals. For example, intermittent administration of a compound described herein, e.g., a compound of Formula I, including an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, is administration for one to six days per week, administration in cycles (e.g., daily administration for two to eight consecutive weeks, then a rest period with no administration for up to one week), or administration on alternate days.

In certain embodiments, a compound described herein, e.g., a compound of Formula I, including an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, is cyclically administered to a patient. Cycling therapy involves the administration of an active agent for a period of time, followed by a rest for a period of time, and repeating this sequential administration. Cycling therapy can reduce the development of resistance to one or more of the therapies, avoid or reduce the side effects of one of the therapies, and/or improves the efficacy of the treatment.

In one embodiment, provided herein is a method for inducing the production of myelin basic protein in a cell, comprising contacting the cell with a compound described herein, e.g., a compound of Formula I, including an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

In another embodiment, provided herein is a method for inhibiting a pro-inflammatory cytokine in a cell, comprising contacting the cell with a compound described herein, e.g., a compound of Formula I, including an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

In yet another embodiment, provided herein is a method for providing neuroprotection to a subject, comprising administering to the subject a compound described herein, e.g., a compound of Formula I, including an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

A compound described herein, e.g., a compound of Formula I, including an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof, can also be combined or used in combination with other therapeutic agents useful in the treatment and/or prevention of a disease described herein.

As used herein, the term "in combination" includes the use of more than one therapy (e.g., one or more prophylactic and/or therapeutic agents). However, the use of the term "in combination" does not restrict the order in which therapies (e.g., prophylactic and/or therapeutic agents) are administered to a subject with a disease or disorder. A first therapy (e.g., a prophylactic or therapeutic agent such as a compound described herein) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to the subject. Triple therapy is also contemplated herein.

The route of administration of a compound described herein, e.g., a compound of Formula I, including an enantiomer, a mixture of enantiomers, or a mixture of diastereomers thereof, or a pharmaceutically acceptable salt, solvate, or prodrug thereof, is independent of the route of administration of a second therapy. In one embodiment, a compound described herein, e.g., a compound of Formula I, including an enantiomer, a mixture of enantiomers, or a mixture of diastereomers thereof; or a pharmaceutically acceptable salt, solvate, or prodrug thereof, is administered orally. In another embodiment, a compound described herein, e.g., a compound of Formula I, including an enantiomer, a mixture of enantiomers, or a mixture of diastereomers thereof, or a pharmaceutically acceptable salt, solvate, or prodrug thereof, is administered intravenously. Thus, in accordance with these embodiments, a compound described herein, e.g., a compound of Formula I, including an enantiomer, a mixture of enantiomers, or a mixture of diastereomers thereof; or a pharmaceutically acceptable salt, solvate, or prodrug thereof, is administered orally or intravenously, and the second therapy can be administered orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form. In one embodiment, a compound described herein, e.g., a compound of Formula I, including an enantiomer, a mixture of enantiomers, or a mixture of diastereomers thereof, or a pharmaceutically acceptable salt, solvate, or prodrug thereof, and a second therapy are administered by the same mode of administration, orally or by IV. In another embodiment, a compound described herein, e.g., a compound of Formula I, including an enantiomer, a mixture of enantiomers, or a mixture of diastereomers thereof; or a pharmaceutically acceptable salt, solvate, or prodrug thereof, is administered by one mode of administration, e.g., by IV, whereas the second agent (an anticancer agent) is administered by another mode of administration, e.g., orally.

In certain embodiments, each method provided herein may independently, further comprise the step of administering a second therapeutic agent.

The compounds provided herein can also be provided as an article of manufacture using packaging materials well known to those of skill in the art. See, e.g., U.S. Pat. Nos. 5,323,907; 5,052,558; and 5,033,252. Examples of pharmaceutical packaging materials include, but are not limited to, blister packs, bottles, tubes, inhalers, pumps, bags, vials, containers, syringes, and any packaging material suitable for a selected formulation and intended mode of administration and treatment.

In certain embodiments, provided herein also are kits which, when used by the medical practitioner, can simplify the administration of appropriate amounts of active ingredients to a subject. In certain embodiments, the kit provided herein includes a container and a dosage form of a compound described herein, including a single enantiomer or a mixture of diastereomers thereof; or a pharmaceutically acceptable salt, solvate, or prodrug thereof.

In certain embodiments, the kit includes a container comprising a dosage form of the compound described herein, including a single enantiomer or a mixture of diastereomers thereof, or a pharmaceutically acceptable salt, solvate, or prodrug thereof, in a container comprising one or more other therapeutic agent(s) described herein.

Kits provided herein can further include devices that are used to administer the active ingredients. Examples of such devices include, but are not limited to, syringes, needle-less injectors drip bags, patches, and inhalers. The kits provided herein can also include condoms for administration of the active ingredients.

Kits provided herein can further include pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: aqueous vehicles, including, but not limited to, Water for Injection USP, Sodium Chloride Injection, Ringer's Injection, Dextrose Injection, Dextrose and Sodium Chloride Injection, and Lactated Ringer's Injection; water-miscible vehicles, including, but not limited to, ethyl alcohol, polyethylene glycol, and polypropylene glycol; and non-aqueous vehicles, including, but not limited to, corn oil, cottonseed oil, peanut oil, sesame oil, ethyl oleate, isopropyl myristate, and benzyl benzoate.

In certain embodiments, provided herein is a method of reducing the secretion of a pro-inflammatory cytokine in a cell, comprising the step of contacting the cell with an effective amount of a compound described herein, e.g., a compound of Formula I, including an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof. In certain embodiments, the pro-inflammatory cytokine is tumor necrosis factor-alpha (TNF-$\alpha$). In certain embodiments, the cell is a human cell.

In certain embodiments, provided herein is a method of protecting an oligodendrocyte against apoptosis induced by a pro-inflammatory cytokine, comprising the step of contacting the oligodendrocyte with an effective amount of a compound described herein, e.g., a compound of Formula I, including an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof. In certain embodiments, the pro-inflammatory cytokine is tumor necrosis factor-alpha (TNF-$\alpha$). In certain embodiments, the oligodendrocyte is a human oligodendrocyte.

In certain embodiments, provided herein is a method of inducing the production of myelin basic protein in a cell, comprising the step of contacting the cell with an effective amount of a compound described herein, e.g., a compound of Formula I, including an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof. In certain embodiments, the cell is a human cell.

In certain embodiment, the effective amount of the compound described herein ranges from about 1 µM to about 1 mM, from about 10 µM to about 10 µM, from about 100 µM to about 2 µM, or from about 1 nM to about 1 µM.

The disclosure will be further understood by the following non-limiting examples.

Examples

As used herein, the symbols and conventions used in these processes, schemes and examples, regardless of whether a particular abbreviation is specifically defined, are consistent with those used in the contemporary scientific literature, for example, the *Journal of the American Chemical Society* or the *Journal of Biological Chemistry*. Specifically, but without limitation, the following abbreviations may be used in the examples and throughout the specification: g (grams); mg (milligrams); mL (milliliters); µL (microliters); mM (millimolar); µM (micromolar); Hz (Hertz); MHz (megahertz); mmol (millimoles); hr or hrs (hours); min (minutes); MS (mass spectrometry); ESI (electrospray ionization); TLC (thin layer chromatography); HPLC (high pressure liquid chromatography); $CDCl_3$ (deuterated chloroform); DMSO-$d_6$ (deuterated dimethylsulfoxide); and DMF (N,N-dimethylformamide).

For all of the following examples, standard work-up and purification methods known to those skilled in the art can be utilized. Unless otherwise indicated, all temperatures are expressed in ° C. (degrees Centigrade). All reactions are conducted at room temperature unless otherwise noted. Synthetic methodologies illustrated herein are intended to exemplify the applicable chemistry through the use of specific examples and are not indicative of the scope of the disclosure.

Example B1

Reduction of TNF-α Secretion from Human Primary Glioblastoma Cells (U87)

TNF-α secretion is measured using U87 cell line. Cells are distributed into 6 well dishes and allowed to adhere overnight. When cells are confluent, they are treated with a test compound at 10 µM in each dish, wherein the test compound is solubilized in neat DMEM. Cells are exposed to the test compound for 48 hrs. Conditioned media is collected and assayed for TNF-α using mouse monoclonal to TNF-α (Abcam 52B83, Cambridge, MA). Conditioned media (100 µL) is applied to each slot. The nitrocellulose filter membrane is blocked with ECL advanced block (2% in Tris buffered saline with Tween-20 (0.05%)) for 1 hr with gentle shaking at room temperature. Primary mouse anti-TNF-α (Abcam 52B83) is diluted 1,000× in the blocking solution. Primary antibodies are applied to blots and incubated overnight at 4° C. with gentle shaking. Blots are developed using enhanced ECL (GE Healthcare) method. Images of bound antibodies are captured using Image Lab software driving a Bio-Rad ChemiDoc XRS+ image capture system.

Example B2

Protection of Human Ologodendrocytes (MO3-13) Against TNF-α Toxicity

MO3-13 cells were grown in 6 well dishes (100,000 cells per dish) and allowed to adhere overnight. Cells were treated with increasing amounts of human recombinant TNF-α protein (Abcam Ab9642). Cells either treated with increasing amounts of TNF-α protein or with vehicle (PBS) were allowed to grow for additional 24 hrs, after which MO3-13 cells were trypsinized and counted using Trypan blue and a Nebauer hemocytometer. Mean cell counts were plotted graphically against TNF-α concentrations. The $LD_{50}$ of human TNF-α was determined to be 30 ng/mL on MO3-13 cells. The protective effects of a test compound on MO3-13 cells that are exposed to $LD_{50}$ human TNF-α protein are then determined.

The protective effects of the test compound on MO3-13 cells against TNF-α toxicity are also determined. MO3-13 cells are grown in 6 well dishes and allowed to adhere overnight. Cells are grown to 70% confluence and then differentiated into oligodendrocyte-like cells by removal of FBS from DMEM medium for 48 hrs. Cells are treated with vehicle (no treatment); human TNF-α protein (30 ng/mL); the test compound at 1 µM; and a combination of the test compound at 1 µM and human TNF-α protein (30 ng/mL). Cells are treated with Abcam's Kinetic Apoptosis Kit (Microscopy) prior to live cell fluorescence microscopy imaging using an inverted Zeiss epi-fluorescent microscope. Merged images of phase contrast, green (pSIVA-IANBD) and red (PI) fluorescence are captured after 1 hr, 15 and 72 hrs in cell culture.

Example B3

Protection of Ologodendrocytes from Cuprizone (Cpz) Demyelination

The Cpz toxicity to MO3-13 was first evaluated. MO3-13 cells were plated onto 10 cm cell culture dishes and grown in DMEM containing 5% FBS. Cells were grown to 75% confluence, after which serum containing DMEM medium was replaced with FBS free DMEM. Cells were grown for 48 hrs under serum deprived conditions. Increasing amounts of Cpz solubilized in 100% ethanol were added to selected dishes and cells were allowed to grow a further 24 hrs, after which cells were assessed visually using an inverted Zeiss microscope equipped with phase contrast optics. As shown in FIG. 1, the treatment of differentiated MO3-13 cells with increasing amounts of Cpz revealed that Cpz was toxic to MO3-13 cells. Experiments designed to assess protection from Cpz toxicity used a 50 µM Cpz exposure.

Figure 2:
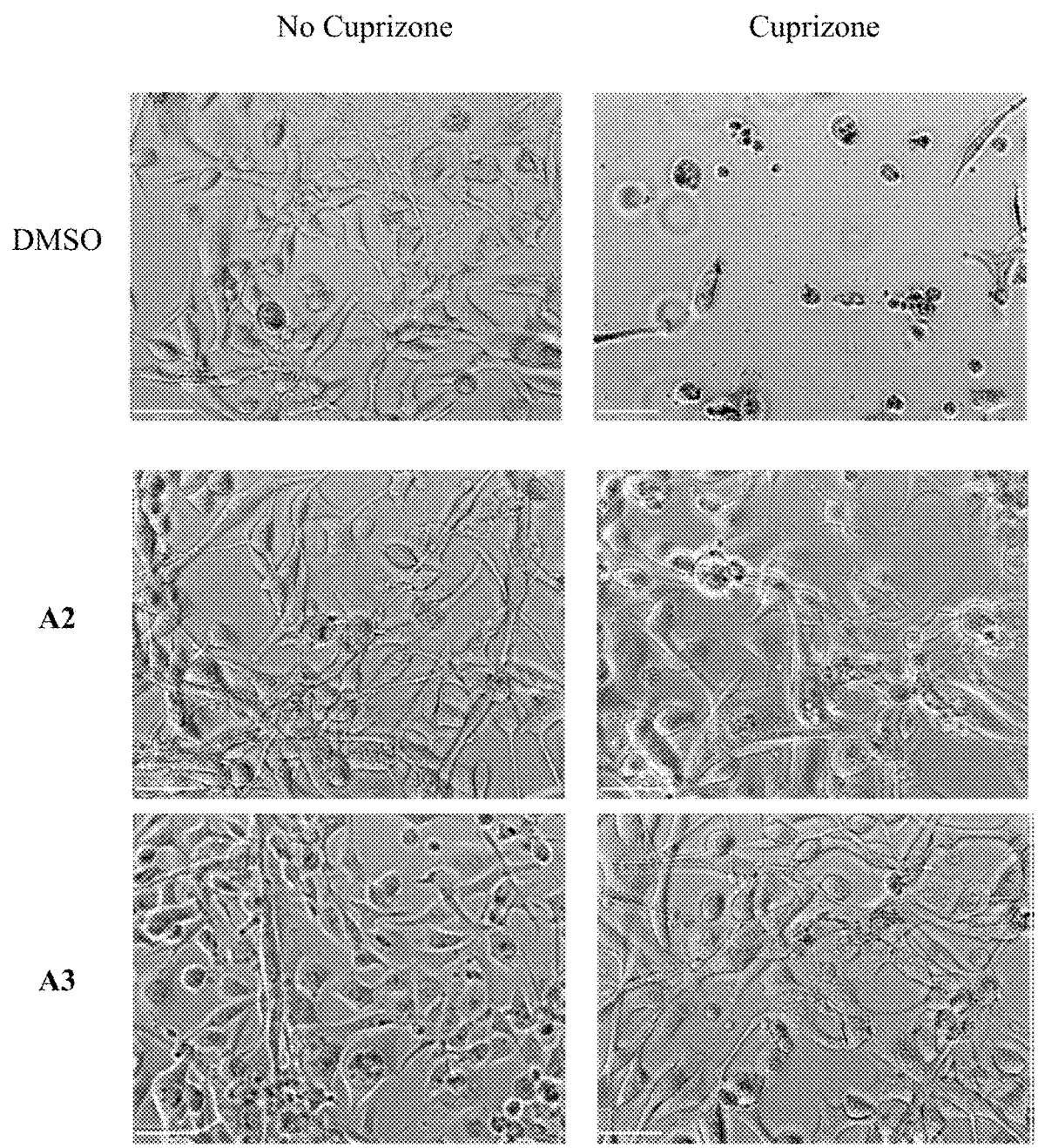
FIG. 2 shows the protection of human oligodendrocytes (MO3-13) with either compound A2 or A3 at at 5 µM against the toxicity of Cpz at 50 µM.

The protective effects of compounds A2 and A2 on MO3-13 cells from Cpz toxicity were then determined. MO3-13 cells were plated onto 6 cm cell culture dishes and grown in DMEM containing 5% FBS. Cells were grown to 75% confluence, after which serum containing DMEM medium was replaced with FBS free DMEM. Cells were grown for 48 hrs under serum deprived conditions. Cpz at a final concentration of 50 µM was solubilized in 100% ethanol was added to selected dishes with compound A1 or A2 at 5 µM in DMSO, or DMSO alone as a control. Cells were grown a further 24 hrs, after which they were assessed visually using an inverted Zeiss microscope equipped with phase contrast optics. The results are shown in FIG. 2.

The protective effects of a test compound from Cpz toxicity is determined using primary mouse oligodendrocytes (Celprogen) and followed with MITOTRACKER®. Stock MITOTRACKER® (Molecular Probes) is diluted with DMSO to a final concentration of 1 mM. MITOTRACKER® (100 nM) is incubated with the live cells at 37° C. for 30 min. MITOTRACKER® labeling of mitochondria is assessed using a Zeiss inverted microscope.

Following MITOTRACKER® treatment, cells are processed for immunocytochemistry. Cells grown on mouse oligodendrocyte extracellular matrix coated cover slips (Celprogen) are fixed with fixing solution containing 0.1% gluteraldehyde, 2% paraformaldehyde, 80 mM Pipes, 5 mM EGTA, pH 8.0, 1 mM $MgCl_2$, and 0.5% Triton-X100. The cells are fixed for 7 min at 37° C. The cells on cover slips are washed and then blocked with 2% bovine serum albumin (BSA) for 1 hr. Primary antibodies are diluted in 2% BSA and incubated on the cover glass for 1 hr in a humid chamber. Following incubation, cover slips are washed and then incubated for 1 hr with species-specific secondary antibodies conjugated with fluorescent label or with biotin. After washing, slides are incubated with streptavidin conjugated with fluorescein fluorescent labels for 40 min. Cover slips are washed again and mounted with DABCO mountant. Fluorescently labeled cells are visualized with a Zeiss epi-fluorescent microscope. Data collected is for MITOTRACKER® (red channel) and beta-catenin (green channel).

The protective effects of a test compound from Cpz toxicity is determined using primary human oligodendrocytes, which are grown and differentiated in 6 well dishes coated with human oligodendrocyte extracellular matrix (ECM) (Celprogen). Cells are weaned off with fetal bovine serum containing differentiation medium (Celprogen) up to 25 days in culture. The cells are exposed to either no treatment (Vehicles=ethanol and DMSO); the test compound ranging in dosage of 2, 5 and 10 µM; Cpz (50 µM) (Sigma Aldrich) or a combination of the test compound and Cpz (50 µM). Cells are treated for 24 hrs, after which images are captured of live cells using an inverted Zeiss microscope.

The protective effects of a test compound from Cpz toxicity are determined using primary human oligodendrocytes (Celprogen) and followed with MITOTRACKER®. MITOTRACKER® (100 nM) is incubated with the live cells at 37° C. for 30 min. MITOTRACKER® labeling of mitochondria is assessed using a Zeiss inverted microscope. Following MITOTRACKER® treatment, cells are processed for immunocytochemistry. Cells grown on human oligodendrocyte extracellular matrix coated cover slips (Celprogen) are fixed with fixing solution containing 0.1% gluteraldehyde, 2% paraformaldehyde, 80 mM Pipes, 5 mM EGTA, pH 8.0, 1 mM $MgCl_2$, and 0.5% Triton-X100. The cells are fixed for 7 min at 37° C. The cells on cover slips are washed and then blocked with 2% bovine serum albumin (BSA) for 1 hr. Primary antibodies are diluted in 2% BSA and incubated on the cover glass for 1 hr in a humid chamber. Following incubation, cover slips are washed and then incubated for 1 hr with species-specific secondary antibodies conjugated with fluorescent label or with biotin. After washing, slides are incubated with streptavidin conjugated with fluorescein fluorescent labels for 40 min. Cover slips are washed again and mounted with DABCO mountant. Fluorescently labeled cells are visualized with a Zeiss epi-fluorescent microscope. Data collected is for MITOTRACKER® (red channel) and MBP (green channel). Nuclei are labeled with DAPI (blue channel).

Example B4

Induction of Myelin Basic Protein (MBP) Production

Figure 3:
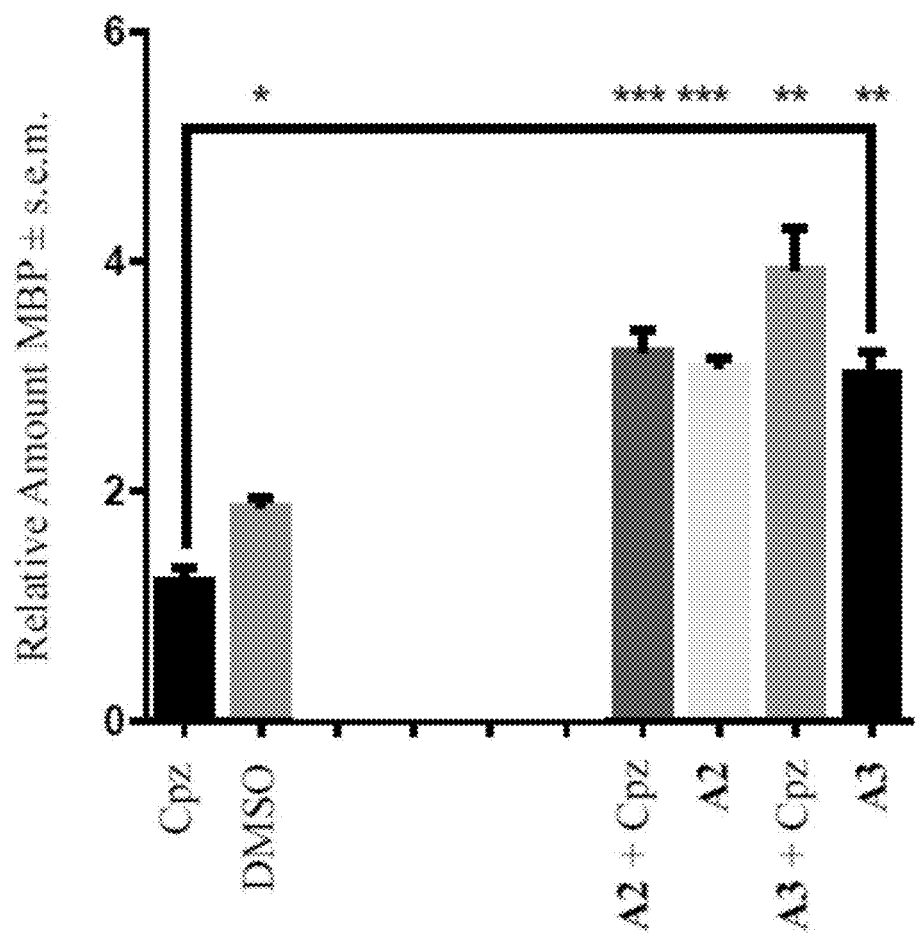
FIG. 3 shows the induction of myelin basic protein (MBP) production with either compound A2 or A3 at 5 µM on human oligodendrocytes (MO3-13) in the presence of Cpz at 50 µM.

Dilutions (0.1 mg/mL) of MO3-13 whole cell extracts were prepared and the proteins (5 µg) from the dilutions were blotted onto nitrocellulose membrane using a slot blotter. The non-protein sites on the blot were blocked with 2% ECL block in PBS-Tween20. Primary anti-Bov MBP was diluted in block solution at 300×. The primary antibody was incubated overnight at 4° C. with gentle shaking. The following day the blot was developed using enhanced ECL (GE Healthcare) method. Image of bound antibody were captured using Image Lab software driving a Bio-Rad ChemiDoc XRS+ image capture system. As shown in FIG. 3, the data revealed that treatment of MO3-13 cells with Cpz resulted in reduced anti-MBP antibody binding as compared with non-treated (DMSO) cells. For those treated with either one of compounds A2 and A3 alone or with Cpz plus one of compounds A2 and A3, MBP bound by anti-MBP was significantly higher.

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference in its entirety. —$NR^{1a}C(S)NR^{1b}R^{1c}$, —$NR^{1a}S(O)R^{1d}$, —$NR^{1a}S(O)_2R^{1d}$, —$NR^{1a}S(O)NR^{1b}R^{1c}$, —$NR^{1a}S(O)_2NR^{1b}R^{1c}$, —$SR^{1a}$, —$S(O)R^{1a}$, —$S(O)_2R^{1a}$, —$S(O)NR^{1b}R^{1c}$, or —$S(O)_2NR^{1b}R^{1c}$, $R^6$ is $C_{3-7}$ cycloalkyl;

each $R^{1a}$ is independently hydrogen, deuterium, $C_{1-6}$ alkyl, $C_{2-6}$ alkenyl, $C_{2-6}$ alkynyl, $C_{3-7}$ cycloalkyl, $C_{7-15}$ aralkyl, heteroaryl, or heterocyclyl; and each $R^{1b}$, $R^{1c}$, and $R^{1d}$ is independently hydrogen, deuterium, $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or $R^{1a}$ and $R^{1c}$ together with the C and N atoms to which they are attached form heterocyclyl; or $R^{1b}$ and $R^{1c}$ together with the N atom to which they are attached form heterocyclyl;

wherein each alkyl, alkenyl, alkynyl, cycloalkyl, aryl, aralkyl, heteroaryl, and heterocyclyl is optionally substituted with one or more substituents Q, where each Q is independently selected from (a) deuterium, cyano, halo, and nitro; (b) $C^{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each of which is further optionally substituted with one or more substituents $Q^a$; and (c)-$C(O)R^a$,-$C(O) OR^a$, —$C(O)NR^bR^c$,-$C(O)SR^a$,-$C(NR^a)NR^bR^c$,-$C(S)R^a$,-$C(S)OR^a$,-$C(S)NR^bR^c$,-$OR^a$,-$OC(O)R^a$, —$OC(O)OR^a$,-$OC(O)NR^bR^c$,-$OC(O)SR^a$,-$OC(=NR^a)NR^bR^c$, $OC(S)R^a$,-$OC(S)OR^a$, —$OC(S)NR^bR^c$,-$OS(O)R^a$,-$OS(O)_2R^a$,-$OS(O)NR^bR^c$,-$OS(O)_2NR^bR^c$,-$NR^bR^c$,-$NR^aC(O)R^d$, -$NR^aC(O)OR^d$,-$NR^aC(O)NR^bR^c$,-$NR^aC(O)SR^d$,-$NR^aC(=NR^d)NR^bR^c$,-$NR^aC(S)R^d$, -$NR^aC(S)OR^d$,-$NR^aC(S)NR^bR^c$,-$NR^aS(O)R^d$,-$NR^aS(O)_2R^d$,-$NR^aS(O)NR^bR^c$, -$NR^aS(O)_2NR^bR^c$,-$SR^a$,-$S(O)R^a$,-$S(O)_2R^a$,-$S(O)NR^bR^c$, and -$S(O)_2NR^bR^c$, wherein each $R^a$, $R^b$, $R^c$, and $R^d$ is independently (i) hydrogen or deuterium; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each of which is optionally substituted with one or more substituents $Q^a$; or (iii) $R^b$ and $R^c$ together with the N atom to which they are attached form heterocyclyl, optionally substituted with one or more substituents $Q^a$;

wherein each $Q^a$ is independently selected from the group consisting of (a) deuterium, cyano, halo, and nitro; (b)

$C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and (c)-C(O)R$^e$,-C(O)OR$^c$, C(O)NR$^f$R$^g$, —C(O)SR$^e$,-C(NR$^e$) NR$^f$R$^g$,-C(S)R$^e$,-C(S)OR$^e$,-C(S)NR$^f$R$^g$,-OR$^e$,-OC(O)R$^e$,-OC(O)OR$^e$, -OC(O)NR$^f$R$^g$,-OC(O)SR$^e$,-OC(=NR$^e$)NR$^f$R$^g$,-OC(S)R$^e$,-OC(S)OR$^e$,-OC(S)NR$^f$R$^g$, -OS(O)R$^e$,-OS(O)$_2$R$^e$,-OS(O)NR$^f$R$^g$,-OS(O)$_2$NR$^f$R$^g$,-NR$^f$R$^g$,-NR$^e$C(O)R$^h$,-NR$^e$C(O)OR$^f$,

What is claimed is:

1. A method for treating, preventing, or ameliorating one or more symptoms of an inflammatory, neurodegenerative, or immune-mediated disease in a subject, comprising administering to the subject a therapeutically effective amount of a pharmaceutical composition comprising a compound of Formula I:

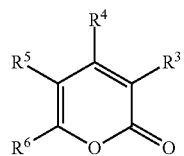

(I)

or an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof; and a pharmaceutically acceptable excipient; wherein:

$R^3$ is hydrogen or deuterium; and $R^5$ is (a) hydrogen, deuterium, cyano, halo, or nitro; or (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or $R^3$ is (a) hydrogen, deuterium, cyano, halo, or nitro; or (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; and $R^5$ is hydrogen or deuterium;

$R^4$ is (a) hydrogen, deuterium, cyano, halo, or nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) -C(O)R$^{1a}$,-C(O)OR$^{1a}$,-C(O)NR$^{1b}$R$^{1c}$,-C(O)SR$^{1a}$,-C(NR$^{1a}$) NR$^{1b}$R$^{1c}$,-C(S)R$^{1a}$,-C(S)OR$^{1a}$, —C(S)NR$^{1b}$R$^{1c}$,-OR$^{1a}$,-OC(O)R$^{1a}$,-OC(O) OR$^{1a}$ ,-OC(O)NR$^{1b}$R$^{1c}$,-OC(O)SR$^{1a}$, —OC(=NR$^{1a}$)NR$^{1b}$R$^{1c}$,-OC(S)R$^{1a}$,-OC(S)OR$^{1a}$,-OC(S)NR$^{1b}$R$^{1c}$,-OS(O)R$^{1a}$,-OS(O)$_2$R$^{1a}$, -OS(O)NR$^{1b}$R$^{1c}$,-OS(O)$_2$NR$^{1b}$R$^{1c}$,-NR$^{1b}$R$^{1c}$,-NR$^{1a}$C(O)R$^{1d}$,-NR$^{1a}$C(O)OR$^{1d}$, -NR$^{1a}$C(O)NR$^{1b}$R$^{1c}$,-NR$^{1a}$C(O)SR$^{1d}$,-NR$^{1a}$C(=NR$^{1d}$) NR$^{1b}$R$^{1c}$,-NR$^{1a}$C(S)R$^{1d}$,-NR$^{1a}$C(S)OR$^{1d}$, —NR$^e$C(O)NR$^f$Rg,-NR$^e$C(O)SR$^f$,-NR$^e$C(=NR$^h$)NR$^f$R$^g$,-NR$^e$C(S)R$^h$,-NR$^e$C(S)OR$^f$, —NR$^e$C(S)NR$^f$R$^g$,-NR$^e$S(O)R$^h$,-NR$^e$S(O)$_2$R$^h$,-NR$^e$S(O)NR$^f$R$^g$,-NR$^e$S(O)$_2$NR$^f$R$^g$,-SR$^e$, —S(O)R$^e$,-S(O)$_2$R$^e$,-S(O)NR$^f$R$^g$, and -S(O)$_2$NR$^f$R$^g$; wherein each R$^e$, R$^f$, R$^g$, and R$^h$ is independently (i) hydrogen or deuterium; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) R$^f$ and R$^g$ together with the N atom to which they are attached form heterocyclyl.

2. A method for treating, preventing, or ameliorating one or more symptoms of an inflammatory, neurodegenerative, or immune-mediateed disease in a subject, comprising administering to the subject a therapeutically effective amount of a compound of Formula III:

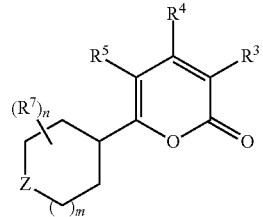

(III)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug therof;

wherein $R^3$ and $R^5$ are each independently (a) hydrogen, deuterium, cyano, halo, or nitro; or (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl;

$R^4$ is (a) hydrogen, deuterium, cyano, halo, or nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —C(O)R$^{1a}$, —C(O)OR$^{1a}$, —C(O) NR$^{1b}$R$^{1c}$, —C(O)SR$^{1a}$, —C(NR$^{1a}$)NR$^{1b}$R$^{1c}$, —C(S) R$^{1a}$, —C(S)OR$^{1a}$, —C(S)NR$^{1b}$R$^{1c}$, —OR$^{1a}$, —OC(O)R$^{1a}$, —OC(O)OR$^{1a}$, —OC(O)NR$^{1b}$R$^{1c}$, —OC(O)SR$^{1a}$, —OC(=NR$^{1a}$)NR$^{1b}$R$^{1c}$, —OC(S)R$^{1a}$, —OC(S)OR$^{1a}$, —OC(S)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(O)SR$^{1d}$, —NR$^{1a}$C(=NR$^{1d}$)NR$^{1b}$R$^{1c}$, —NR$^{1a}$C(S) R$^{1d}$, —NR$^{1a}$C(S)OR$^{1d}$, —NR$^{1a}$C(S)NR$^{1b}$R$^{1c}$, —NR$^{1a}$S(O)R$^{1d}$, —NR$^{1a}$S(O)$_2$R$^{1d}$, —NR$^{1a}$S(O) NR$^{1b}$R$^{1c}$, —NR$^{1a}$S(O)$_2$NR$^{1b}$R$^{1c}$, —SR$^{1a}$, —S(O) R$^{1a}$, —S(O)$_2$R$^{1a}$, —S(O)NR$^{1b}$R$^{1c}$ or —S(O)$_2$NR$^{1b}$R$^{1c}$;

Z is a bond,-O-,-S-,-S(O)-,-S(O$_2$)-, or -N(R$^8$)-;

each R$^7$ is independently (a) deuterium, halo, cyano, nitro, or guanidine; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c)-C(O)R$^{1a}$,-C(O) OR$^{1a}$,-C(O)NR$^{1b}$R$^{1c}$,-C(O)SR$^{1a}$,-C(NR$^{1a}$)NR$^{1b}$R$^{1c}$, —C(S)R$^{1a}$,-C(S)OR$^{1a}$,-C(S)NR$^{1b}$R$^{1c}$,-OR$^{1a}$,-OC(O)R$^{1a}$,-OC(O)OR$^{1a}$,-OC(O)NR$^{1b}$R$^{1c}$, -OC(O)SR$^{1a}$,-OC(=NR$^{1a}$)NR$^{1b}$R$^{1c}$,-OC(S)R$^{1a}$,-OC(S)OR$^{1a}$,-OC(S)NR$^{1b}$R$^{1c}$,-OS(O)R$^{1a}$, -OS(O)$_2$R$^{1a}$,-OS(O)NR$^{1b}$R$^{1c}$,-OS(O)$_2$NR$^{1b}$R$^{1c}$,-NR$_{1b}$R$^{1c}$,-NR$^{1a}$C(O)R$^{1d}$,-NR$^{1a}$C(O)OR$_{1d}$, -NR$^{1a}$C(O)NR$^{1b}$R$^{1c}$,-NR$^{1a}$C (O) SR$^{1d}$,-NR$^{1a}$C(=NR$^{1d}$) NR$_{1b}$R$^{1c}$,-NR$^{1a}$C(S)R$^{1d}$, -NR$^{1a}$C(S) R$^{1d}$,-NR$^{1a}$C(S)NR$^{1b}$R$^{1c}$,-NR$^{1a}$S(O)R$^{1d}$,-NR$^{1a}$S(O)$_2$R$^{1d}$,-NR$^{1a}$S(O)NR$_{1b}$R$^{1c}$, -NR$^{1a}$S(O)$_2$NR$_{1b}$R$_{1c}$,-SR$^{1a}$,-S(O)R$^{1a}$,-S(O)$_2$R$^{1a}$,-S(O)NR$^{1b}$R$^{1c}$, or -S(O)$_2$NR$^{1b}$R$^{1c}$, or two R$^7$ are linked together to form (a) a bond,-O-,-NR$^8$-, or -S-; or (b) $C_{1-6}$ alkylene, $C_{1-6}$ heteroalkylene, $C_{2-6}$ alkenylene, or $C_{2-6}$ heteroalkenylene;

$R^8$ is independently (a) hydrogen or deuterium; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c)-C(O)R$^{1a}$,-C(O)OR$^{1a}$,-C(O)NR$^{1b}$R$^{1c}$,-C(O) SR$^{1a}$,-C(NR$^{1a}$)NR$^{1b}$R$^{1c}$,-C(S)R$^{1a}$,-C(S)OR$^{1a}$, —C(S)NR$^{1b}$R$^{1c}$,-OR$^{1a}$,-OC(O)R$^{1a}$, -OC(O)OR$^{1a}$,-OC(O)NR$^{1b}$R$^{1c}$,-OC(O)SR$^{1a}$, —OC(=NR$^{1a}$) NR$^{1b}$R$^{1c}$,-OC(S)R$^{1a}$,-OC(S)OR$^{1a}$,-OC(S)NR$^{1b}$R$^{1c}$,-

$OS(O)R^{1a}$,-$OS(O)_2R^{1a}$, -$OS(O)NR^{1b}R^{1c}$,-$OS(O)_2NR^{1b}R^{1c}$,-$NR_{1b}R^{1c}$,-$NR^{1a}C(O)R^{1d}$,-$NR^{1a}C(O)OR^{1d}$, -$NR^{1a}C(O)NR^{1b}R^{1c}$,-$NR^{1a}C(O)SR^{1d}$,-$NR^{1a}C(=NR^{1d})$ $NR^{1b}R^{1c}$,-$NR^{1a}C(S)R^{1d}$,-$NR^{1a}C(S)OR^{1d}$, -$NR^{1a}C(S)NR^{1b}R^{1c}$,-$NR^{1a}S(O)R^{1d}$,-$NR^{1a}S(O)_2R^{1d}$,-$NR^{1a}S(O)NR^{1b}R^{1c}$,-$NR^{1a}S(O)_2NR^{1b}R^{1c}$, -$SR^{1a}$,-$S(O)R^{1a}$,-$S(O)_2R^{1a}$,-$S(O)NR^{1b}R^{1c}$, or -$S(O)_2NR^{1b}R^{1c}$, m is an integer of 1, 2, 3, or 4;

n is an integer of 0, 1, 2, 3, 4, 5, 6, or 7;

each $R^{1a}$ is independently hydrogen, deuterium, $C_{1-6}$ alkyl, $C_{2-6}$ alkenyl, $C_{2-6}$ alkynyl, $C_{3-7}$ cycloalkyl, $C_{7-15}$ aralkyl, heteroaryl, or heterocyclyl; and each $R^{1b}$, $R^{1c}$, and $R^{1d}$ is independently hydrogen, deuterium, $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or $R^{1a}$ and $R^{1c}$ together with the C and N atoms to which they are attached form heterocyclyl; or $R^{1b}$ and $R^{1c}$ together with the N atom to which they are attached form heterocyclyl;

wherein each alkyl, alkenyl, alkynyl, cycloalkyl, aryl, aralkyl, heteroaryl, and heterocyclyl is optionally substituted with one or more substituents Q, where each Q is independently selected from (a) deuterium, cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each of which is further optionally substituted with one or more substituents $Q^a$; and (c)-$C(O)R^a$,-$C(O)$ $OR^a$, —$C(O)NR^bR^c$,-$C(O)SR^a$,-$C(NR^a)NRDR^a$,-$C(S)R^a$,-$C(S)OR^a$,-$C(S)NR^bR^c$,-$OR^a$,-$OC(O)R^a$, -$OC(O)OR^a$,-$OC(O)NR^bR^c$,-$OC(O)SR^a$,-$OC(=NR^a)NR^bR^c$,-$OC(S)R^a$,-$OC(S)OR^a$, —$OC(S)NR^bR^c$,-$OS(O)R^a$,-$OS(O)_2R^a$,-$OS(O)NR^bR^c$,-$OS(O)_2NR^bR^c$,-$NR^bR^c$,-$NR^aC(O)R^d$, -$NR^aC(O)OR^d$,-$NR^aC(O)NR^bR^c$,-$NR^aC(O)SR^d$,-$NR^aC(=NR^d)NR^bR^c$,-$NR^aC(S)R^d$,-$NR^aC(S)OR^d$,-$NR^aC(S)NR^bR^c$,-$NR^aS(O)R^d$,-$NR^aS(O)_2R^d$,-$NR^aS(O)NR^bR^c$, -$NR^aS(O)^2NR^bR^c$,-$SR^a$,-$S(O)R^a$,-$S(O)_2R^a$,-$S(O)NR^bR^c$, and -$S(O)_2NR_bR^c$, wherein each $R^a$, $R^b$, $R^c$, and $R^d$ is independently (i) hydrogen or deuterium; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each of which is optionally substituted with one or more substituents $Q^a$; or (iii) $R^b$ and $R^c$ together with the N atom to which they are attached form heterocyclyl, optionally substituted with one or more substituents $Q^a$;

wherein each $Q^a$ is independently selected from the group consisting of (a) deuterium, cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and (c)-$C(O)R^e$,-$C(O)OR^e$,-$C(O)NR^fR^g$, —$C(O)SR^e$,-$C(NR^e)NR^fR^g$,-$C(S)R^e$,-$C(S)OR^e$,-$C(S)$ $NR^fR^g$,-$OR^e$,-$OC(O)R^e$,-$OC(O)OR^e$, -$OC(O)NR^fR^g$,-$OC(O)SR^e$,-$OC(=NR^e)NR^fR^g$,-$OC(S)R^e$,-$OC(S)OR^e$,-$OC(S)NR^fR^g$, -$OS(O)R^e$,-$OS(O)_2R^e$,-$OS(O)NR^fR^g$,-$OS(O)_2NR^fR^g$,-$NR^fR^g$,-$NR^eC(O)R^h$,-$NR^eC(O)OR^f$, —$NR^eC(O)NR^fR^g$,-$NR^eC(O)SR^f$,-$NR^eC(=NR^h)$ $NR^fR^g$,-$NR^eC(S)R^h$,-$NR^eC(S)OR^f$, —$NR^eC(S)NR^fR^g$,-$NR^aS(O)R^h$,-$NR^aS(O)_2R^h$,-$NR^aS(O)NR^fR^g$,-$NR^aS(O)_2NR^fR^g$,-$SR^a$, —$S(O)Re$, -$S(O)_2R^e$, -$S(O)NR^fR^g$, and -$S(O)_2NR^fR^g$; wherein each $R^e$, $R^f$, $R^g$, and $R^h$ is independently (i) hydrogen or deuterium; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl;

or (iii) $R^f$ and $R^g$ together with the N atom to which they are attached form heterocyclyl.

3. The method of claim 2, wherein Z is a bond.

4. The method of claim 2, wherein m is an integer of 0 or 1.

5. A method for treating, preventing, or ameliorating one or more symptoms of an inflammatory, neurodegenerative, or immune-mediated disease in a subject, comprising administering to the subject a therapeutically effective amount of a pharmaceutical composition comprising a compound of Formula I:

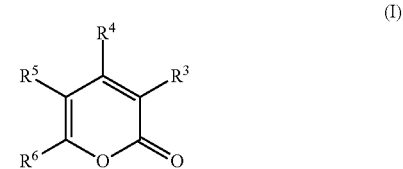

(I)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; and a pharmaceutically acceptable excipient; wherein:

$R^3$ is hydrogen or deuterium; and $R^5$ is (a) hydrogen, deuterium, cyano, halo, or nitro; or (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or $R^3$ is (a) hydrogen, deuterium, cyano, halo, or nitro; or (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; and $R^5$ is hydrogen or deuterium;

$R^4$ is $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl;

$R^6$ is $C_{3-7}$ cycloalkyl or heterocyclyl;

each $R^{1a}$ is independently hydrogen, deuterium, $C_{1-6}$ alkyl, $C_{2-6}$ alkenyl, $C_{2-6}$ alkynyl, $C_{3-7}$ cycloalkyl, $C_{7-15}$ aralkyl, heteroaryl, or heterocyclyl; and each $R^{1b}$, $R^{1c}$, and $R^{1d}$ is independently hydrogen, deuterium, $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or $R^{1a}$ and $R^{1c}$ together with the C and N atoms to which they are attached form heterocyclyl; or $R^{1b}$ and Rlc together with the N atom to which they are attached form heterocyclyl;

wherein each alkyl, alkenyl, alkynyl, cycloalkyl, aryl, aralkyl, heteroaryl, and heterocyclyl is optionally substituted with one or more substituents Q, where each Q is independently selected from (a) deuterium, cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each of which is further optionally substituted with one or more substituents $Q_a$; and (c)-$C(O)R^a$,-$C(O)$ $OR^a$, —$C(O)NR^bR^c$,-$C(O)SR^a$,-$C(NR^a)NR^bR^c$,-$C(S)R^a$,-$C(S)OR^a$,-$C(S)NR^bR^c$,-$OR^a$,-$OC(O)R^a$, —$OC(O)OR^a$,-$OC(O)NR^bR^c$,-$OC(O)SR^a$,-$OC(=NR^a)NR^bR^c$, —$OC(S)R^a$,-$OC(S)OR^a$, —$OC(S)NR_bR^c$,-$OS(O)R^a$,-$OS(O)_2R^a$,-$OS(O)NR^bR^c$,-$OS(O)_2NR^bR^c$,-$NR^bR^c$,-$NR^aC(O)R^d$, —$NR^aC(O)OR^d$,-$NR^aC(O)NR^bR^c$,-$NR^aC(O)SR^d$,-$NR^aC(=NR^d)NR_bR^c$,-$NR^aC(S)R^d$, —$NR^aC(S)OR^d$,-$NR^aC(S)NR^bR^c$,-$NR^aS(O)R^d$,-$NR^aS(O)_2R^d$,-$NR^aS(O)NR^bR^c$, —NR$^a$S(O)$_2$NR$_b$R$^c$,-SR$^a$,-S(O)R$^a$,-S(O)$_2$R$^a$,-S(O)NR$^b$R$^c$, and -S(O)$_2$NR$^b$R$^c$, wherein each R$^a$ R$^b$, R$^c$, and R$^d$ is independently (i) hydrogen or deuterium; (ii) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl, each of which is optionally substituted with one or more substituents Q$^a$, or (iii) R$^b$ and R$^c$ together with the N atom to which they are attached form heterocyclyl, optionally substituted with one or more substituents Q$^a$;

wherein each Q$^a$ is independently selected from the group consisting of (a) deuterium, cyano, halo, and nitro; (b) C$^{1-6}$ alkyl, C$^{2-6}$ alkenyl, C$_{2-6}$ alkynyl, C$^{3-7}$ cycloalkyl, C$^{6-14}$ aryl, C$^{7-15}$ aralkyl, heteroaryl, and heterocyclyl; and (c)-C(O)R$^e$,-C(O)OR$^e$,-C(O)NR$^f$R$^g$, —C(O)SR$^e$,-C(NR$^e$)NR$^f$R$^g$,-C(S)R$^e$, C(S)OR$^e$, C(S)NR$^f$R$^g$,-OR$^e$, OC(O)R$^e$,-OC(O)OR$^e$, —OC(O)NR$^f$R$^g$, -OC(O)SR$^e$,-OC(=NR$^e$)NR$^f$R$^g$,-OC(S)R$^e$, OC(S)OR$^e$, -OC(S)NR$^f$R$^g$, —OS(O)R$^e$,-OS(O)$_2$R$^e$,-OS(O)NR$^f$R$^g$, —OS(O)$_2$NR$^f$R$^g$,-NR$^f$R$^g$,-NR$^e$C(O)R$^h$,-NR$^e$C(O)OR$^f$, -NR$^e$C(O)NR$^f$R$^g$,-NR$^e$C(O)SR$^f$, -NR$^e$C(=NR$^h$)NR$^f$R$^g$,-NR$^e$C(S)R$^h$,-NR$^e$C(S)OR$^f$, —NR$^e$C(S)NR$^f$R$^g$,-NR$^a$S(O)R$^h$,-NR$^a$S(O)$_2$R$^h$,-NR$^a$S(O)NR$^f$R$^g$,-NR$^a$S(O)$_2$NR$^f$R$^g$,-SR$^e$ S(O)R$^e$, -S(O)$_2$R$^e$, —S(O)NR$^f$R$^g$, and -S(O)$_2$NR$^f$ R$^g$; wherein each R$^e$, R$^f$, R$^g$ and R$^h$ is independently (i) hydrogen or deuterium; (ii) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl; or (iii) R$^f$ and R$^g$ together with the N atom to which they are attached form heterocyclyl.

6. The method of claim 5, wherein R$^4$ is C$_{1-6}$ alkyl or C$_{6-14}$ aryl, each optionally substituted with one or more substituents Q.

7. The method of claim 6, wherein R$^4$ is methyl or phenyl, each optionally substituted with one or more substituents Q.

8. The method of claim 1, wherein R$^3$ is hydrogen or deuterium.

9. The method of claim 1, wherein R$^5$ is hydrogen or deuterium.

10. A method for treating, preventing, or ameliorating one or more symptoms of an inflammatory, neurodegenerative, or immune-mediated disease in a subject, comprising administering to the subject a therapeutically effective amount of 6-cyclohexyl-4-methyl-2H-pyran-2-one, 6-cyclohexyl-4-phenyl-2H-pyran-2-one, or 4,6-diphenyl-2H-pyran-2-one; or a tautomer, a mixture of two or more tautomers, or an isotopic variant thereof; or a pharmaceutically acceptable salt, solvate, hydrate, or prodrug thereof.

11. A method for treating, preventing, or ameliorating one or more symptoms of an inflammatory, neurodegenerative, or immune-mediated disease in a subject comprising administering to the subject a therapeutically effective amount of a pharmaceutical composition comprising a compound of Formula I:

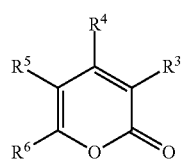

(I)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; and a pharmaceutically acceptable excipient;

wherein:

R$^3$ is hydrogen or deuterium; and R$^5$ is (a) hydrogen, deuterium, cyano, halo, or nitro; or (b) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl; or R$^3$ is (a) hydrogen, deuterium, cyano, halo, or nitro; or (b) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl; and R$^5$ is hydrogen or deuterium;

R$^4$ is (a) hydrogen, deuterium, cyano, halo, or nitro; (b) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl; or (c) —C(O)R$^{1a}$,-C(O)OR$^{1a}$, C(O)NR$^{1b}$R$^{1c}$,-C(O)SR$^{1a}$,-C(NR$^{1a}$)NR$^{1b}$R$^{1c}$, -C(S)R$^{1a}$,-C(S)OR$^{1a}$, —C(S)NR$^{1b}$R$^{1c}$,-OR$^{1a}$, —OC(O)R$^{1a}$, —OC(O)OR$^{1a}$, —OC(O)NR$^{1b}$R$^{1c}$, —OC(O)SR$^{1a}$, —OC(=NR$^{1a}$)NR$^{1b}$R$^{1c}$,-OC(S)R$^{1a}$, —OC(S)OR$^{1a}$,-OC(S)NR$^{1b}$R$^{1c}$, —OS(O)R$^{1a}$,-OS(O)$_2$R$^{1a}$, —OS(O)NR$^{1b}$R$^{1c}$,-OS(O)$_2$NR$^{1b}$R$^{1c}$,-NR$^{1b}$R$^{1c}$,-NR$_{1a}$C(O)R$^{1d}$,-NR$^{1a}$C(O)OR$^{1d}$, —NR$^{1a}$C(O)NR$^{1b}$R$^{1c}$,-NR$^{1a}$C(O)SR$^{1d}$, —NR$^{1a}$C(=NR$^{1d}$)NR$^{1b}$R$^{1c}$,-NR$_{1a}$C(S)R$^{1d}$,—NR$^{1a}$C(S)OR$^{1d}$, -NR$^{1a}$C(S)NR$^{1b}$R$^{1c}$,-NR$^{1a}$S(O)R$^{1d}$, —NR$^{1a}$S(O)$_2$R$^{1d}$, —NR$^{1a}$S(O)NR$^{1b}$R$^{1c}$,-NR$^{1a}$S(O)$_2$NR$^{1b}$R$^{1c}$, -SR$^{1a}$,-S(O)R$^{1a}$,-S(O)$_2$R$^{1a}$, -S(O)NR$^{1b}$R$^{1c}$, or -S(O)$_2$NR$^{1b}$R$^{1c}$, R$^6$ is C$_{3-7}$ cycloalkyl or heterocyclyl;

each R$^{1a}$ is independently hydrogen, deuterium, C$_{1-6}$ alkyl, C$_{2-6}$ alkenyl, C$_{2-6}$ alkynyl, C$_{3-7}$ cycloalkyl, C$_{7-15}$ aralkyl, heteroaryl, or heterocyclyl; and each R$^{1b}$, R$^{1c}$, and R$^{1d}$ is independently hydrogen, deuterium, C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl; or R$^{1a}$ and R$_{1c}$ together with the C and N atoms to which they are attached form heterocyclyl; or R$^{1b}$ and R$^{1c}$ together with the N atom to which they are attached form heterocyclyl;

wherein each alkyl, alkenyl, alkynyl, cycloalkyl, aryl, aralkyl, heteroaryl, and heterocyclyl is optionally substituted with one or more substituents Q, where each Q is independently selected from (a) deuterium, cyano, halo, and nitro; (b) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, and heterocyclyl, each of which is further optionally substituted with one or more substituents Q$^a$, and (c)-C(O)R$^a$,-C(O)OR$^a$, —C(O)NR$^b$R$^c$, —C(O)SR$^a$,-C(NR$^a$)NR$^b$R$^c$,-C(S)R$^a$,-C(S)OR$^a$,-C(S)NR$^b$R$^c$,-OR$^a$, —OC(O)R$^a$, —OC(O)OR$^a$,-OC(O)NR$^b$R$^c$,-OC(O)SR$^a$, —OC(=NR$^a$)NR$^b$R$^c$,-OC(S)R$^a$,-OC(S)OR$^a$, —OC(S)NR$^b$R$^c$,-OS(O)R$^a$,-OS(O)$_2$R$^a$,-OS(O)NR$^b$R$^c$,-OS(O)$_2$NR$^b$R$^c$,-NR$^b$R$^c$,-NR$^a$C(O)R$^d$, -NR$^a$C(O)OR$^d$,-NR$^a$C(O)NR$^b$R$^c$,-NR$^a$C(O)SR$^d$,-NR$^a$C(=NR$^d$)NR$^b$R$^c$, -NR$^a$C(S)R$^d$, -NR$^a$C(S)OR$^d$,-NR$^a$C(S)NR$^b$R$^c$,-NR$^a$S(O)R$^d$,-NR$^a$S(O)$_2$R$^d$,-NR$^a$S(O)NR$^b$R$^c$, -NR$^a$S(O)$_2$NR$^b$R$^c$,-SR$^a$,-S(O)R$_a$,-S(O)$_2$R$^a$,-S(O)NR$^b$R$^c$, and -S(O)$_2$NR$^b$R$^c$, wherein each R$^a$ R$^b$, R$^c$, and R$^d$ is independently (i) hydrogen or deuterium; (ii) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl, each of which is optionally substituted with one or more substituents Q$^a$, or (iii) R$^b$ and R$^c$ together with the N atom to which they are attached form heterocyclyl, optionally substituted with one or more substituents $Q^a$;

wherein each $Q^a$ is independently selected from the group consisting of (a) deuterium, cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and (c)-C(O)$R^e$,-C(O)O$R^e$,-C(O)NR$^f$R$^g$, —C(O)S$R^e$,-C(NR$^e$)NR$^f$R$^g$,-C(S)$R^e$,-C(S)O$R^e$,-C(S)NR$^f$R$^g$,-O$R^e$,-OC(O)$R^e$,-OC(O)O$R^e$, —OC(O)NR$^f$R$^g$, —OC(O)S$R^e$, —OC(=NR$^e$)NR$^f$R$^g$, —OC(S)$R^e$, —OC(S)O$R^e$,-OC(S)NR$^f$R$^g$, —OS(O)$R^e$,-OS(O)$_2$R$^e$, -OS(O)NR$^f$R$^g$, -OS(O)$_2$NR$^f$R$^g$, -NR$^f$R$^g$, —NR$^e$C(O)R$^h$, -NR$^e$C(O)OR$^f$, -NR$^e$C(O)NR$^f$R$^g$,-NR$^e$C(O)SR$^f$, -NR$^a$C(=NR$^h$)NR$^f$R$^g$, -NR$^e$C(S)R$^h$,-NR$^e$C(S)OR$^f$, -NR$^e$C(S)NR$^f$R$^g$,-NR$^a$S(O)R$^h$,-NR$^a$S(O)$_2$R$^h$,-NR$^a$S(O)NR$^f$R$^g$,-NR$^a$S(O)$_2$NR$^f$R$^g$, -SR$^e$, -S(O)R$^e$, -S(O)$_2$R$^e$, —S(O)NR$^f$R$^g$, and -S(O)$_2$NR$^f$R$^g$; wherein each R$^e$, R$^f$, R$^g$, and R$^h$ is independently (i) hydrogen or deuterium; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) R$^f$ and R$^g$ together with the N atom to which they are attached form heterocyclyl; and wherein the composition is in single dosage form or an oral dosage form.

12. The method of claim 11, wherein the composition is in an oral dosage form.

13. The method of claim 12, wherein the oral dosage form is a tablet or capsule.

14. A method for treating, preventing, or ameliorating one or more symptoms of an immune-mediated disease in a subject, comprising administering to the subject a therapeutically effective amount of a pharmaceutical composition comprising a compound of Formula I:

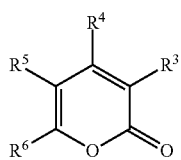

(I)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; and a pharmaceutically acceptable excipient;

wherein:
$R^3$ is hydrogen or deuterium; and $R^5$ is (a) hydrogen, deuterium, cyano, halo, or nitro; or (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or $R^3$ is (a) hydrogen, deuterium, cyano, halo, or nitro; or (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; and $R^5$ is hydrogen or deuterium;

$R^4$ is (a) hydrogen, deuterium, cyano, halo, or nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —C(O)R$^{1a}$, —C(O)OR$^{1a}$, —C(O)NR$^{1b}$R$^{1c}$,—C(O)SR$^{1a}$,—C(NR$^{1a}$)NR$^{1b}$R$^{1c}$, —C(S)R$^{1a}$, -C(S)OR$^{1a}$, —C(S)NR$^{1b}$R$^{1c}$, —OR$^{1a}$, -OC(O)R$^{1a}$, —OC(O)OR$^{1a}$, —OC(O)NR$^{1b}$R$^{1c}$, —OC(O)SR$^{1a}$, —OC(=NR$^{1a}$)NR$^{1b}$R$^{1c}$, —OC(S)R$^{1a}$, —OC(S)OR$^{1a}$, —OC(S)NR$^{1b}$R$^{1c}$, —OS(O)R$^{1a}$, -OS(O)$_2$R$^{1a}$, —OS(O)NR$^{1b}$R$^{1c}$, —OS(O)$_2$NR$^{1b}$R$^{1c}$,-NR$^{1b}$R$^{1c}$, -NR$^{1a}$C(O)R$^{1d}$, —NR$^{1a}$C(O)OR$^{1d}$, —NR$^{1a}$C(O)NR$^{1b}$R$^{1c}$,-NR$^{1a}$C(O)SR$^{1d}$,-NR$_{1a}$C(=NR$^{1d}$)NR$^{1b}$R$^{1c}$,-NR$^{1a}$C(S)R$^{1d}$, -NR$^{1a}$c(S)OR$^{1d}$,-NR$^{1a}$C(S)NR$^{1b}$R$^{1c}$, -NR$^{1a}$S(O)R$^{1d}$,-NR$^{1a}$S(O)$_2$R$^{1d}$, —NR$^{1a}$S(O)NR$^{1b}$R$^{1c}$,-NR$^{1a}$S(O)$_2$NR$^{1b}$R$^{1c}$, —SR$^{1a}$,-S(O)R$^{1a}$,-S(O)$_2$R$^{1a}$, -S(O)NR$^{1b}$R$^{1c}$, or -S(O)$_2$NR$^{1b}$R$^{1c}$;

$R^6$ is $C_{3-7}$ cycloalkyl or heterocyclyl;

each $R^{1a}$ is independently hydrogen, deuterium, $C_{1-6}$ alkyl, $C_{2-6}$ alkenyl, $C_{2-6}$ alkynyl, $C_{3-7}$ cycloalkyl, $C_{7-15}$ aralkyl, heteroaryl, or heterocyclyl; and each $R^{1b}$, $R^{1c}$, and $R^{1d}$ is independently hydrogen, deuterium, $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or $R^{1a}$ and $R^{1c}$ together with the C and N atoms to which they are attached form heterocyclyl; or $R^{1b}$ and $R^{1c}$ together with the N atom to which they are attached form heterocyclyl;

wherein each alkyl, alkenyl, alkynyl, cycloalkyl, aryl, aralkyl, heteroaryl, and heterocyclyl is optionally substituted with one or more substituents Q, where each Q is independently selected from (a) deuterium, cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each of which is further optionally substituted with one or more substituents $Q^a$; and (c)-C(O)R$^a$,-C(O)OR$^a$, —C(O)NR$^b$R$_c$, —C(O)SR$^a$, —C(NR$^a$)NR$^b$R$^c$, —C(S)R$^a$, -C(S)OR$^a$, -C(S)NR$^b$R$^c$, -OR$^a$, -OC(O)R$^a$, —OC(O)OR$^a$,-OC(O)NR$^b$R$^c$,-OC(O)SR$^a$,-OC(=NR$^a$)NR$^b$R$^c$,-OC(S)R$^a$,-OC(S)OR$^a$, —OC(S)NR$^b$R$^c$,-OS(O)R$^a$,-OS(O)$_2$R$^a$,-OS(O)NR$^b$R$^c$,-OS(O)$_2$NR$^b$R$^c$,-NR$^b$R$^c$, —NR$^a$C(O)R$^d$, —NR$^a$C(O)OR$^d$,-NR$^a$C(O)NR$^b$R$^c$,-NR$^a$C(O)SR$^d$,-NR$^a$C(=NR$^d$)NR$^b$R$^c$, -NR$^a$C(S)R$^d$, -NR$^a$C(S)OR$^d$,-NR$^a$C(S)NR$^b$R$^c$,-NR$^a$S(O)R$^d$,-NR$^a$S(O)$_2$R$^d$,-NR$^a$S(O)NR$^b$R$^c$, -NR$^a$S(O)$_2$NR$^b$R$^c$,-SR$^a$,-S(O)R$^a$,-S(O)$_2$R$^a$,-S(O)NR$^b$R$^c$, and -S(O)$_2$NR$^b$R$^c$, wherein each R$^a$ R$^b$, R$^c$, and R$^d$ is independently (i) hydrogen or deuterium; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each of which is optionally substituted with one or more substituents $Q^a$; or (iii) R$^b$ and R$^c$ together with the N atom to which they are attached form heterocyclyl, optionally substituted with one or more substituents $Q^a$;

wherein each $Q^a$ is independently selected from the group consisting of (a) deuterium, cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and (c)-C(O)R$^e$,-C(O)OR$^e$, —C(O)NR$^f$R$^g$, —C(O)SR$^e$,-C(NR$^e$)NR$^f$R$^g$,-C(S)R$^e$,-C(S)OR$^e$,-C(S)NR$^f$R$^g$,-OR$^e$,-OC(O)R$^e$,-OC(O)OR$^e$, —OC(O)NR$^f$R$^g$, -OC(O)SR$^e$, -OC(=NR$^e$)NR$^f$R$^g$, -OC(S)R$^e$,-OC(S)OR$^e$,-OC(S)NR$^f$R$^g$, —OS(O)R$^e$,-OS(O)$_2$R$^e$,-OS(O)NR$^f$R$^g$, -OS(O)$_2$NR$^f$R$^g$, -NR$^f$R$^g$,-NR$^e$C(O)R$^h$,-NR$^e$C(O)OR$^f$, -NR$^e$C(O)NR$^f$R$^g$,-NR$^e$C(O)SR$^f$, -NR$^e$C(=NR$^h$)NR$^f$R$^g$,-NR$^e$C(S)R$^h$,-NR$^e$C(S)OR$^f$, -NR$^e$C(S)NR$^f$R$^g$,-NR$^a$S(O)R$^h$,-NR$^a$S(O)$_2$R$^h$,-NR$^a$S(O)NR$^f$R$^g$,-NR$^a$S(O)$_2$NR$^f$R$^g$, -SR$^e$,-S(O)R$^e$,-S(O)$_2$R$^e$,-S(O)NR$^f$R$^g$, and -S(O)$_2$NR$^f$R$^g$; wherein each R$^e$, R$^f$, R$^g$, and R$^h$ is independently (i) hydrogen or deuterium; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) $R^f$ and $R^g$ together with the N atom to which they are attached form heterocyclyl.

15. The method of claim 14, wherein the immune-mediated disease is an autoimmune disease.

16. The method of claim 14, wherein the immune-mediated disease is multiple sclerosis.

17. The method of claim 16, wherein the disease is relapsing-remitting MS (RR-MS), primary progressive MS (PP-MS), progressive relapsing MS (PR-MS), or secondary progressive MS (SP-MS).

* * * * *